(12) United States Patent
Gudmundsson et al.

(10) Patent No.: US 7,030,134 B2
(45) Date of Patent: Apr. 18, 2006

(54) PYRAZOLOPYRIDINYL PYRIDINE AND PYRIMIDINE THERAPEUTIC COMPOUNDS

(75) Inventors: Kristjan Gudmundsson, Durham, NC (US); Brian A. Johns, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/095,212

(22) Filed: Mar. 31, 2005

(65) Prior Publication Data

US 2005/0192303 A1  Sep. 1, 2005

Related U.S. Application Data

(62) Division of application No. 10/473,751, filed as application No. PCT/US02/10687 on Apr. 5, 2002.

(60) Provisional application No. 60/286,948, filed on Apr. 27, 2001.

(51) Int. Cl.
C07D 401/04 (2006.01)
A61K 31/4439 (2006.01)

(52) U.S. Cl. .................... 514/300; 546/121
(58) Field of Classification Search ............ 546/121; 514/300
See application file for complete search history.

(56) References Cited

U.S. PATENT DOCUMENTS

| 4,576,952 A | 3/1986 | Hurst et al. |
| 4,621,089 A | 11/1986 | Ward et al. |
| 4,985,444 A | 1/1991 | Shiokawa et al. |
| 5,155,114 A | 10/1992 | Shiokawa et al. |
| 5,204,346 A | 4/1993 | Shiokawa et al. |
| 5,234,930 A | 8/1993 | Shiokawa et al. |
| 5,296,490 A | 3/1994 | Shiokawa et al. |
| 5,300,478 A | 4/1994 | Michaely et al. |
| 5,498,774 A | 3/1996 | Mitsudera et al. |
| 5,552,422 A | 9/1996 | Gauthier et al. |
| 5,670,432 A | 9/1997 | Tsai |
| 5,700,816 A | 12/1997 | Isakson et al. |
| 5,773,530 A | 6/1998 | Akahane et al. |
| 5,990,148 A | 11/1999 | Isakson et al. |
| 6,136,839 A | 10/2000 | Isakson et al. |
| 6,207,675 B1 | 3/2001 | Carry et al. |

FOREIGN PATENT DOCUMENTS

| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |
| WO | 0 364 204 A1 | 10/1989 |
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96 41625 | 12/1996 |
| WO | WO 96 41626 | 12/1996 |
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |
| WO | WO 99 64419 | 12/1999 |
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 02/16359 | 2/2002 |
| WO | WO 02 16359 | 2/2002 |
| WO | WO 02 18382 | 3/2002 |
| WO | WO 02/18382 | 3/2002 |
| WO | WO 02 48147 | 6/2002 |
| WO | WO 02/048148 | 6/2002 |

(Continued)

OTHER PUBLICATIONS

Vane, J. et al. "Towards a Better Aspirin," Nature, vol. 367, Jan. 20, 1994, pp. 215-216.

(Continued)

Primary Examiner—Deepak Rao
(74) Attorney, Agent, or Firm—Lorie Ann Morgan

(57) ABSTRACT

The present invention provides compounds of formula (I):

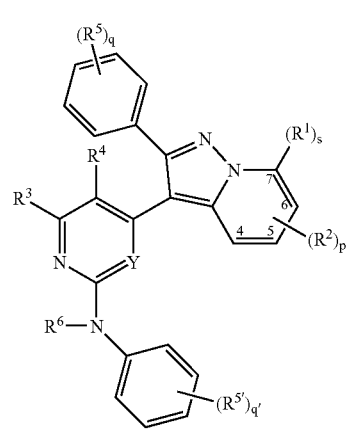

wherein all variables are as defined herein, pharmaceutical compositions containing the same, processes for preparing the same and their use as pharmaceutical agents.

22 Claims, No Drawings

FOREIGN PATENT DOCUMENTS

WO     WO 02 066481     8/2002
WO     WO 03/00682     1/2003

OTHER PUBLICATIONS

Carter, J. et al. "Recently Reported Inhibitors of Cyclooxygenase-2," Exp. Opin. Ther. Patents (1998), 8(1), pp. 21-29.

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz. & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR 838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency," J. Med. Chem. 1996, 39, pp. 3929-3937.

Hanson, G.J., et al. "Pulmonary-Allergy, Dermatological, Gastrointestinal & Arthritis, Inhibitors of p38 kinase." Expert Opinion Ther. Patents, 1997, 7(7):729-733.

Roizman, B., et al. "The Family Herpesviridae: A Brief Introduction," Fields Virology, vol. 2, 4th Edition, pp. 2381-2397.

Douglas, R.G., Jr. "Introduction to Viral Diseases." Cecil Textbook of Medicine, 20th Edition, vol. 2, pp. 1739-1747, 1996.

Razonable, R.R., et al. "Herpes Virus Infections in Transplant Recipients: Current Challenges in the Clinical Management of Cytomegalovirus and Epstein-Barr Virus Infections." PubMed Abstract, Herpes 10(3):60-5, Dec. 2003.

Bosseray; A., et al. "What's New in Vaccines Against Herpes Simplex Infections." PubMed Abstract, Pathol. Biol (Paris) 50 (*):483-92, Oct. 2002.

PYRAZOLOPYRIDINYL PYRIDINE AND PYRIMIDINE THERAPEUTIC COMPOUNDS

CROSS-REFERENCE TO RELATED APPLICATIONS

This application is divisional of U.S. patent application Ser. No. 10/473,751, filed 1 Oct. 2003, which is a 371 Application of PCT/US02/10687, filed 5 Apr. 2002, which claims priority to U.S. Application Ser. No. 60/286,948, filed 27 Apr. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the U.S. alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

Varicella zoster virus (VZV) (also known as herpes zoster virus) is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atherosclerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome, multiple sclerosis and Alzheimer's disease.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

BRIEF SUMMARY OF THE INVENTION

According to a first aspect of the invention there is provided a compound of formula (I):

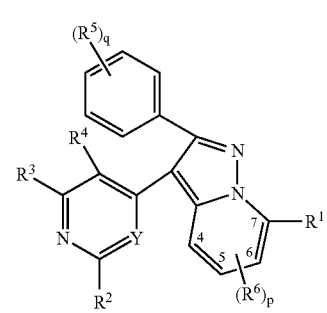

I wherein:
R¹ is selected from the group consisting of halo, Ay, Het, —NR⁷R⁸, —NR⁷Ay, —NHHet, —NHR¹⁰Ay and —NHR¹⁰Het;
  each R⁷ and R⁸ are the same or different and are independently selected from the group consisting of H, alkyl, alkenyl, cycloalkyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —CH(R¹⁰OR⁹)₂, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R¹⁰, —R¹⁰SO₂NR⁹R¹¹, —R¹⁰SO₂NHCOR⁹, —R¹⁰NR⁹R¹¹, —R¹⁰NHCOR⁹, —R¹⁰NHSO₂R⁹ and —R¹⁰NHC(NH)NR⁹R¹¹ and;
  each R⁹ and R¹¹ are the same or different and are independently selected from the group consisting of H, alkyl, cycloalkyl, —R¹⁰cycloalkyl, —R¹⁰OH, —R¹⁰(OR¹⁰)_w where w is 1–10, and —R¹⁰NR¹⁰R¹⁰;
  each R¹⁰ is the same or different and is independently selected from the group consisting of alkyl, alkenyl, alkynyl, cycloalkyl and cycloalkenyl;
  Ay is aryl;
  Het is a 5- or 6-membered heterocyclic or heteroaryl group;
  n is 0, 1 or 2;
R² is selected from the group consisting of halo, alkyl, alkenyl, cycloalkyl, cycloalkenyl, Ay, Het, —OR⁷, —OAy, —OHet, —OR¹⁰Het, —S(O)_nR⁹, —S(O)_nAy, —S(O)_nHet, —S(O)_nNR⁷R⁸, —NR⁷R⁸, —NHHet, —NHR¹⁰Ay, —NHR¹⁰Het, —R¹⁰NR⁷R⁸ and —R¹⁰NR⁷Ay;
Y is N or CH;
R³ and R⁴ are the same or different and are each independently selected from the group consisting of H, halo, alkyl, alkenyl, cycloalkyl, Ay, Het, —OR⁷, —OAy, —C(O)R⁷, C(O)Ay, —CO₂R⁷, —CO₂Ay, —SO₂NHR⁹, —NR⁷R⁸, —NR⁷Ay, —NHHet, —NHR¹⁰Het —R¹⁰OR⁷, —R¹⁰OAy, —R¹⁰NR⁷R⁸ and —R¹⁰NR⁷Ay;
q is 0, 1, 2, 3, 4 or 5;
each R⁵ is the same or different and is independently selected from the group consisting of halo, alkyl, alkenyl, alkynyl, cycloalkyl, cycloalkenyl, Ay, Het, —OR⁷, —OAy, —OHet, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)_nR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰OR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R⁹, —R¹⁰SO₂NR⁹R¹¹, —R₁₀SO₂NHCOR⁹, —R¹⁰NR⁷R⁸, —R¹⁰NR⁷Ay, —R¹⁰NHC(NH)NR⁹R¹¹, cyano, nitro and azido; or
  two adjacent R⁵ groups together with the atoms to which they are bonded form a C₅₋₆ cycloalkyl or aryl;
p is 1, 2 or 3; and
each R⁶ is the same or different and is independently selected from the group consisting of halo, alkyl, alkenyl, alkynyl, cycloalkyl, cycloalkenyl, Ay, Het, —OR⁷, —OAy, —OHet, —OR¹⁰Ay, —OR¹⁰Het, —C(O)R⁹, —C(O)Ay, —C(O)Het, —CO₂R⁹, —C(O)NR⁷R⁸, —C(O)N R⁷Ay, —C(O)NHR¹⁰Ay, —C(O)NHR¹⁰Het, —C(S)NR⁹R¹¹, —C(NH)NR⁷R⁸, —C(NH)NR⁷Ay, —S(O)_nR⁹, —S(O)_nAy, —S(O)_nHet, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Ay, —R¹⁰Het, —R¹⁰OR⁹, —R¹⁰—O—C(O)R⁹, —R¹⁰—O—C(O)Ay, —R¹⁰—O—C(O)Het, —R¹⁰—O—S(O)_nR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or
  two adjacent R⁶ groups together with the atoms to which they are bonded form a C₅₋₆ cycloalkyl or a 5- or 6-membered heterocyclic group containing 1 or 2 heteroatoms; or
  R⁶ is in the 6 position and R⁶ and R¹ together with the atoms to which they are bonded form a C₅₋₆ cycloalkyl or a 5- or 6-membered heterocyclic group containing 1 or 2 heteroatoms;
wherein when Y is CH, R³ is not —NR⁷Ay;

and pharmaceutically acceptable salts, solvates and physiologically functional derivatives thereof.

In another aspect of the invention there is provided a pharmaceutical composition comprising a compound of formula (I). In one embodiment, the pharmaceutical composition further comprises a pharmaceutically acceptable carrier or diluent. In one embodiment, the pharmaceutical composition further comprises an antiviral agent selected from the group consisting of aciclovir and valaciclovir.

In a third aspect of the invention, there is provided a method for the prophylaxis or treatment of a herpes viral infection in an animal. The method comprises administering to the animal a therapeutically effective amount of a compound of formula (I) or a pharmaceutically acceptable salt, solvate or physiologically functional derivative thereof. The herpes viral infection can be any of herpes simplex virus 1, herpes simplex virus 2, cytomegalovirus, Epstein Barr virus, varicella zoster virus, human herpes virus 6, human herpes virus 7, and human herpes virus 8.

In a fourth aspect, there is provided a method for the prophylaxis or treatment of conditions or diseases associated with a herpes viral infection in an animal. The method comprises administering to the animal a therapeutically effective amount of the compound of formula (I) or a pharmaceutically acceptable salt, solvate or physiologically functional derivative thereof.

In another aspect, there is provided a process for preparing the compound of formula (I), wherein Y is N, R² is selected from the group consisting of alkyl, alkenyl, cycloalkyl, cycloalkenyl, Ay, Het, —OR⁷, —OAy, —OHet, —OR¹⁰Het, —S(O)_nR⁹, —S(O)_nAy, —S(O)_nHet, —S(O)_nNR⁷R⁸, —NR⁷R⁸, —NHHet, —NHR¹⁰Ay, —NHR¹⁰Het, —R¹⁰NR⁷R⁸ and —R¹⁰NR⁷Ay; and R³ and R⁴ are H. The process comprises the steps of:
a) reacting a compound of formula (VIII):

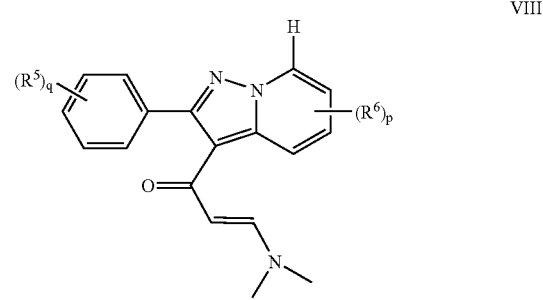

VIII wherein q, $R^5$, p and $R^6$ are as defined above in connection with compounds of formula (I);

with a compound of formula (X):

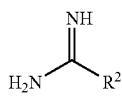

to prepare a compound of formula (IX):

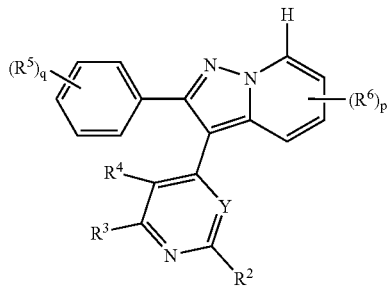

b) halogenating the compound of formula (IX) to prepare a compound of formula (I-A):

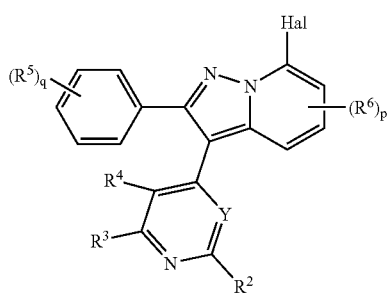

where Hal is halo; and c) optionally either:
  1) replacing the C-7 halogen of the compound of formula (I-A) with an amine nucleophile selected from the group consisting of —$NR^7R^8$, —$NR^7Ay$, —NHHet, —$NHR^{10}Ay$ and —$NHR^{10}Het$; or
  2) coupling the compound of formula (I-A) with a metal compound selected from the group consisting of Ay-$M^3$ and Het-$M^3$ wherein $M^3$ is —$B(OH)_2$, —$B(ORa)_2$, —$B(Ra)_2$, —$Sn(Ra)_3$, Zn-halide, Zn—Ra or Mg-halide where Ra is alkyl or cycloalkyl and halide is halo, to prepare a compound of formula (I-B):

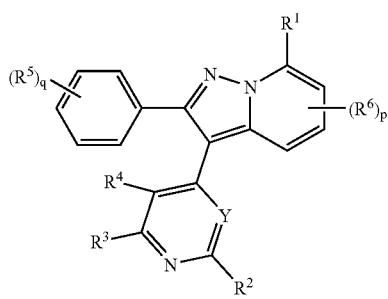

wherein $R^1$ is selected from the group consisting of Ay, Het, —$NR^7R^8$, —$NR^7Ay$, —NHHet, —$NHR^{10}Ay$, and —$NHR^{10}Het$.

In another aspect, the present invention provides a process for preparing a compound of formula (I) wherein Y is N; $R^2$ is selected from the group consisting of alkyl, alkenyl, cycloalkyl, cycloalkenyl, Ay, Het, —$OR^7$, —OAy, —OHet, —$OR^{10}Het$, —$S(O)_nR^9$, —$S(O)_nAy$, —$S(O)_nHet$, —$S(O)_n NR^7R^8$, —$NR^7R^8$, —NHHet, —$NHR^{10}Ay$, —$NHR^{10}Het$, —$R^{10}NR^7R^8$ and —$R^{10}NR^7Ay$; $R^3$ is selected from the group consisting of H, halo, alkyl, alkenyl, cycloalkyl, Het, —$C(O)R^7$, $C(O)Ay$, —$CO_2R^7$, —$CO_2Ay$, —$SO_2NHR^9$, —$NR^7R^8$ where neither $R^7$ nor $R^8$ is H, —$NR^7Ay$ where $R^7$ is not H, —$R^{10}OR^7$, —$R^{10}OAy$, —$R^{10}NR^7R^8$ and —$R^{10}NR^7Ay$; and $R^4$ is H. The process comprises the steps of:

a) reacting a compound of formula (XVI):

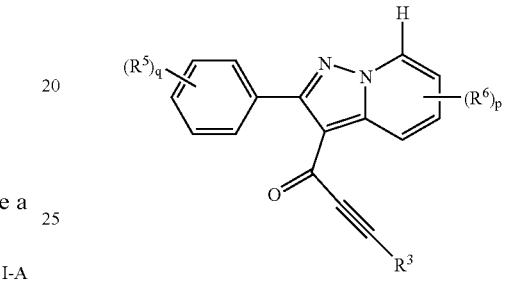

wherein q, $R^5$, p and $R^6$ are as defined above in connection with compounds of formula (I);

with a compound of formula (X):

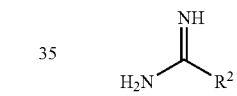

to prepare a compound of formula (IX):

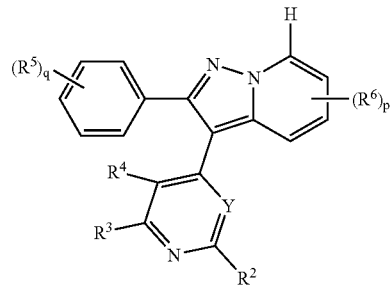

b) halogenating the compound of formula (IX) to prepare a compound of formula (I-A):

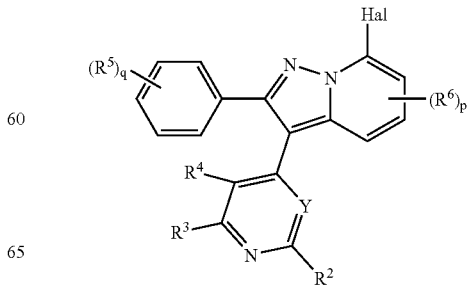

where Hal is halo; and
c) optionally either:
1) replacing the C-7 halogen of the compound of formula (I-A) with an amine nucleophile selected from the group consisting of —NR⁷R⁸, —NR⁷Ay, —NHHet, —NHR¹⁰Ay and —NHR¹⁰Het; or
2) coupling the compound of formula (I-A) with a metal compound selected from the group consisting of Ay-M³ and Het-M³ wherein M³ is —B(OH)₂, —B(ORa)₂, —B(Ra)₂, —Sn(Ra)₃, Zn-halide, Zn—Ra or Mg-halide where Ra is alkyl or cycloalkyl and halide is halo;

to prepare a compound of formula (I-B):

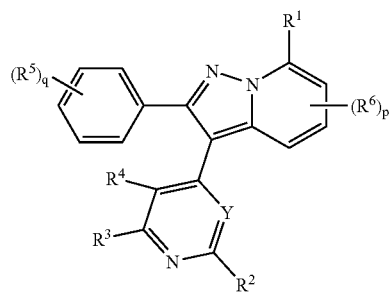

wherein R¹ is selected from the group consisting of Ay, Het, —NR⁷R⁸, —NR⁷Ay, —NHHet, —NHR¹⁰Ay and —NHR¹⁰Het.

In another aspect, the present invention provides another process for preparing compounds of formula (I) or a salt, solvate or physiologically functional derivative thereof, wherein Y is N and R² is selected from the group consisting of alkyl, alkenyl, cycloalkyl, cycloalkenyl, Ay, Het, —OR⁷, —OAy, —OHet, —OR¹⁰Het, —S(O)ₙR⁹, —S(O)ₙAy, —S(O)ₙHet, —S(O)ₙNR⁷R⁸, —NR⁷R⁸, —NHHet, —NHR¹⁰Ay, —NHR¹⁰Het, —R¹⁰NR⁷R⁸ and —R¹⁰NR⁷Ay. The process comprises the steps of:
a) reacting a compound of formula (XX):

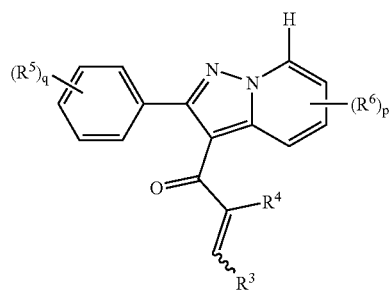

wherein q, R⁵, p and R⁶ are as defined above in connection with compounds of formula (I);

with a compound of formula (X):

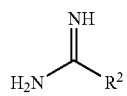

to prepare an intermediate compound;
b) oxidizing the intermediate compound to prepare a compound of formula (IX):

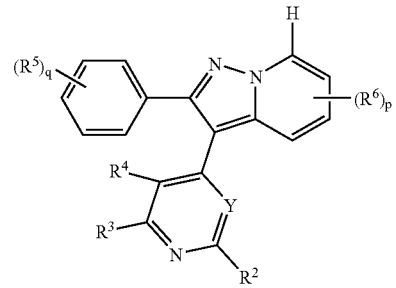

c) halogenating the compound of formula (IX) to prepare a compound of formula (I-A):

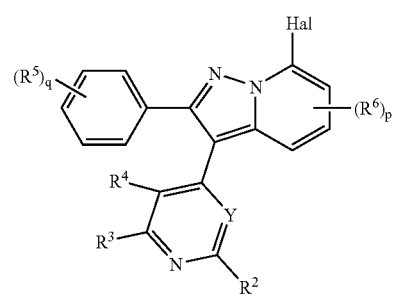

where Hal is halo; and
d) optionally either:
1) replacing the C-7 halogen of the compound of formula (I-A) with an amine nucleophile selected from the group consisting of —NR⁷R⁸, —NR⁷Ay, —NHHet, —NHR¹⁰Ay and —NHR¹⁰Het; or
2) coupling the compound of formula (I-A) with a metal compound selected from the group consisting of Ay-M³ and Het-M³ wherein M³ is —B(OH)₂, —B(ORa)₂, —B(Ra)₂, —Sn(Ra)₃, Zn-halide, Zn—Ra or Mg-halide where Ra is alkyl or cycloalkyl and halide is halo, to prepare a compound of formula (I-B):

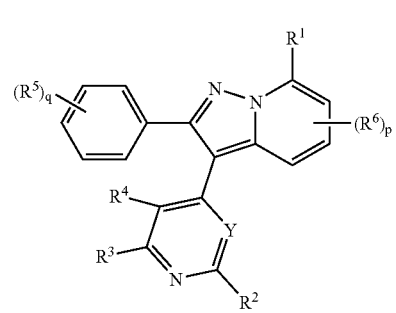

wherein R¹ is selected from the group consisting of Ay, Het, —NR⁷R⁸, —NR⁷Ay, —NHHet, —NHR¹⁰Ay and —NHR¹⁰Het.

In another aspect, the present invention provides another process for preparing compounds of formula (I). The process comprises the steps of:

a) reacting a compound of formula (XXII):

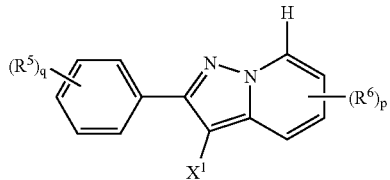

XXII wherein q, $R^5$, p and $R^6$ are as defined above in connection with compounds of formula (I), and $X^1$ is selected from the group consisting of chloro, bromo and iodo;

with a compound of formula (XXIV):

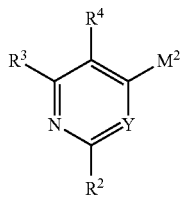

XXIV wherein Y, $R^2$, $R^3$ and $R^4$ are as defined above in connection with compounds of formula (I), and $M^2$ is selected from the group consisting of —B(OH)$_2$, —B(ORa)$_2$, —B(Ra)$_2$, —Sn(Ra)$_3$, Zn-halide, ZnRa, and Mg-halide where Ra is alkyl or cycloalkyl and halide is halo;

to prepare a compound of formula (IX):

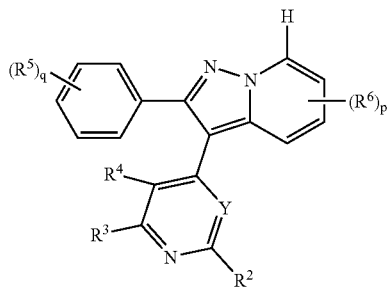

IX b) halogenating the compound of formula (IX) to prepare a compound of formula (I-A):

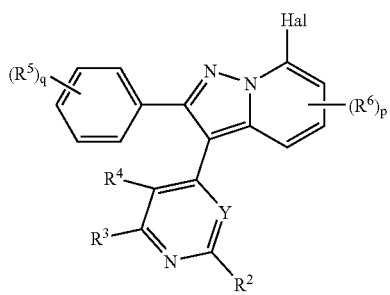

I-A where Hal is halo; and c) optionally either:
  1) replacing the C-7 halogen of the compound of formula (I-A) with an amine nucleophile selected from the group consisting of —NR$^7$R$^8$, —NR$^7$Ay, —NHHet, —NHR$^{10}$Ay and —NHR$^{10}$Het; or
  2) coupling the compound of formula (I-A) with a metal compound selected from the group consisting of Ay-M$^3$ and Het-M$^3$ wherein M$^3$ is —B(OH)$_2$, —B(ORa)$_2$, —B(Ra)$_2$, —Sn(Ra)$_3$, Zn-halide, Zn—Ra or Mg-halide where Ra is alkyl or cycloalkyl and halide is halo, to prepare a compound of formula (I-B):

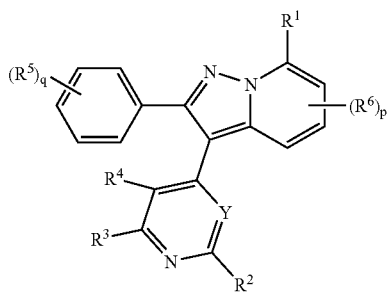

I-B wherein $R^1$ is selected from the group consisting of Ay, Het, —NR$^7$R$^8$, —NR$^7$Ay, —NHHet, —NHR$^{10}$Ay and —NHR$^{10}$Het In another aspect, the present invention provides a radio-labeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof. In another aspect, the present invention provides a biotinylated compound of formula (I) or a pharmaceutically acceptable salt, solvate or physiologically functional derivative thereof.

In another aspect, the present invention provides a compound of formula (I) for use in therapy.

In yet another aspect, the present invention provides a compound of formula (I) for use in the prophylaxis or treatment of a herpes viral infection.

In yet another aspect, the present invention provides a compound of formula (I) for use in the prophylaxis or treatment of conditions or diseases associated with a herpes viral infection in an animal.

In yet another aspect, the present invention provides the use of a compound of formula (I) for the preparation of a medicament for the prophylaxis or treatment of a herpes viral infection in animal, particularly humans.

In yet another aspect, the present invention provides the use of a compound of formula (I) for the preparation of a medicament for the treatment or prophylaxis of diseases or conditions associated with a herpes viral infection in animals, preferrably humans.

DETAILED DESCRIPTION OF THE INVENTION

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (VII), (IX), (XVI), (XX), and (XXII), the phrase "a compound of formula (number)" means a compound having that formula and pharmaceutically acceptable salts, solvates and physiologically functional derivatives thereof.

As used herein, the terms "alkyl" (and alkylene) refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. "Alkyl" also includes substituted alkyl. The alkyl groups may be optionally substituted with one or more substituents selected from the group consisting of mercapto, nitro, cyano and halo. Perhaloalkyl, such as trifluoromethyl is one particular alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may be optionally substituted on an available carbon with one or more substituents selected from the group consisting of mercapto, nitro, cyano, halo and alkyl.

As used herein, the term "alkenyl" (and alkenylene) refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may optionally be substituted on an available carbon with one or more substituents selected from the group consisting of mercapto, nitro, cyano, halo and alkyl.

As used herein, the term "cycloalkenyl" refers to refers to a non-aromatic carbocyclic ring having from 3 to 8 carbon atoms (unless otherwise specified) and up to 3 carbon-carbon double bonds. "Cycloalkenyl" includes by way of example cyclobutenyl, cyclopentenyl and cyclohexenyl. "Cycloalkenyl" also includes substituted cycloalkenyl. The cycloalkenyl may optionally be substituted on an available carbon with one or more substituents selected from the group consisting of mercapto, nitro, cyano, halo and alkyl.

As used herein, the term "alkynyl" (and alkynylene) refers to straight or branched hydrocarbon chains containing from 2 to 8 carbon atoms and at least one and up to three carbon—carbon triple bonds. Examples of "alkynyl" as used herein include, but are not limited to ethynyl and propynyl. "Alkynyl" also includes substituted alkynyl. The alkynyl groups may optionally be substituted on an available carbon with one or more substituents selected from the group consisting of mercapto, nitro, cyano, halo and alkyl.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl, and naphthyl. "Aryl" also includes substituted aryl. Aryl groups may optionally be substituted on an available carbon with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Particular aryl groups according to the invention include but are not limited to phenyl and substituted phenyl.

The term "heterocyclic" (or "heterocycle") refers to a monocyclic saturated or unsaturated non-aromatic groups and fused bicyclic non-aromatic groups, having the specified number of members and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocyclic" also includes substituted heterocyclic. The heterocyclic groups may optionally be substituted on an available carbon or heteroatom with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, cycloalkylamine, carboxy, carboxamide, sulfonamide, Het, amidine, cyano, nitro and azido. Particular heterocyclic groups according to the invention include but are not limited to pyrrolidine, piperidine, morpholine, thiomorpholine and piperazine and substituted variants thereof.

The term "heteroaryl" refers to aromatic monocyclic groups and aromatic fused bicyclic groups having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl. The heteroaryl groups may optionally be substituted on an available carbon or heteroatom with one or more substituents selected from the group consisting of halo, alkyl (including perhaloalkyl), alkenyl, cycloalkyl, cycloalkenyl, alkoxy, cycloalkoxy, amino, mercapto, hydroxy, alkylhydroxy, alkylamine, cycloalkylamine, carboxy, carboxamide, sulfonamide, Het, amidine, cyano, nitro and azido. Particular heteroaryl groups according to the invention include but are not limited to pyridine, furan, thiophene, pyrrole, imidazole, pyrazole and pyrimidine, and substituted variants thereof.

The term "members" (and variants thereof e.g., "membered") in the context of heterocyclic and heteroaryl groups refers to the total atoms, carbon and heteroatoms N, O and/or S, which form the ring. Thus, an example of a 6-membered heterocyclic ring is piperidine and an example of a 6-membered heteroaryl ring is pyridine.

As used herein, the term "optionally" means that the subsequently described event(s) may or may not occur, and includes both event(s) that occur and events that do not occur.

The present invention provides compounds of formula (I):

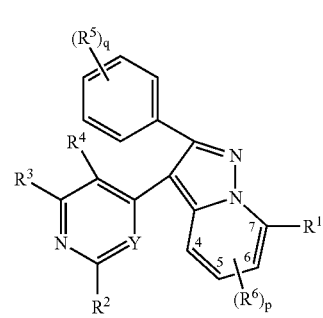

wherein:

$R^1$ is selected from the group consisting of halo, Ay, Het, —$NR^7R^8$, —$NR^7Ay$, —NHHet, —$NHR^{10}$ Ay and —$NHR^{10}$Het;

each $R^7$ and $R^8$ are the same or different and are independently selected from the group consisting of H, alkyl, alkenyl, cycloalkyl, cycloalkenyl, —$OR^9$, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}OR^9$, —$CH(R^{10}OR^9)_2$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$ and;

each $R^9$ and $R^{11}$ are the same or different and are independently selected from the group consisting of H, alkyl, cycloalkyl, —$R^{10}$cycloalkyl, —$R^{10}OH$, —$R^{10}(OR^{10})_w$ where w is 1–10, and —$R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

n is 0, 1 or 2;

$R^2$ is selected from the group consisting of halo, alkyl, alkenyl, cycloalkyl, cycloalkenyl, Ay, Het, —$OR^7$, —OAy, —OHet, —$OR^{10}$Het, —$S(O)_nR^9$, —$S(O)_nAy$, —$S(O)_n$Het, —$S(O)_nNR^7R^8$, —$NR^7R^8$, —NHHet, —$NHR^{10}Ay$, —$NHR^{10}$Het, —$R^{10}NR^7R^8$ and —$R^{10}NR^7Ay$;

Y is N or CH;

$R^3$ and $R^4$ are the same or different and are each independently selected from the group consisting of H, halo, alkyl, alkenyl, cycloalkyl, Ay, Het, —$OR^7$, —OAy, —$C(O)R^7$, $C(O)Ay$, —$CO_2R^7$, —$CO_2Ay$, —$SO_2NHR^9$, —$NR^7R^8$, —$NR^7Ay$, —NHHet, —$NHR^{10}$Het —$R^{10}OR^7$, —$R^{10}OAy$, —$R^{10}NR^7R^8$ and —$R^{10}NR^7Ay$;

q is 0, 1, 2, 3, 4 or 5;

each $R^5$ is the same or different and is independently selected from the group consisting of halo, alkyl, alkenyl, alkynyl, cycloalkyl, cycloalkenyl, Ay, Het, —$OR^7$, —OAy, —OHet, —$C(O)R^9$, —$C(O)Ay$, —$C(O)$Het, —$CO_2R^9$, —$C(O)NR^7R^8$, —$C(O)NR^7Ay$, —$C(O)NHR^{10}$Het, —$C(S)NR^9R^{11}$, —$C(NH)NR^7R^8$, —$C(NH)NR^7Ay$, —$S(O)_nR^9$, —$S(O)_2NR^7R^8$, —$S(O)_2NR^7Ay$, —$NR^7R^8$, —$NR^7Ay$, —NHHet, —$NHR^{10}$Ay, —$NHR^{10}$Het, —$R^{10}$cycloalkyl, —$R^{10}OR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7Ay$. —$R^{10}NHC(NH)NR^9R^{11}$, cyano, nitro and azido; or two adjacent $R^5$ groups together with the atoms to which they are bonded form a $C_{5-6}$ cycloalkyl or aryl;

p is 1, 2 or 3; and each $R^6$ is the same or different and is independently selected from the group consisting of halo, alkyl, alkenyl, alkynyl, cycloalkyl, cycloalkenyl, Ay, Het, —$OR^7$, —OAy, —OHet, —$OR^{10}$Ay, —$OR^{10}$Het, —$C(O)R^9$, —$C(O)Ay$, —$C(O)$Het, —$CO_2R^9$, —$C(O)NR^7R^8$, —$C(O)NR^7Ay$, —$C(O)NHR^{10}$Ay, —$C(O)NHR^{10}$Het, —$C(S)NR^9R^{11}$, —$C(NH)NR^7R^8$, —$C(NH)NR^7Ay$, —$S(O_nR^9$, —$S(O)_n$Ay, —$S(O)_n$Het, —$S(O)_2NR^7R^8$, —$S(O)_2NR^7Ay$, —$NR^7R^8$, —$NR^7Ay$, —NHHet, —$NHR^{10}$Ay, —$NHR^{10}$Het, —$R^{10}$cycloalkyl, —$R^{10}$Ay, —$R^{10}$Het, —$R^{10}OR^9$, —$R^{10}$—O—$C(O)R^9$, —$R^{10}$—O—$C(O)Ay$, —$R^{10}$—O—$C(O)$Het, —$R^{10}$—O—$S(O)_nR^9$, —$R^{10}C(O)R^9$, —$R^{10}CO_2R^9$, —$R^{10}C(O)NR^9R^{11}$, —$R^{10}C(S)NR^9R^{11}$, —$R^{10}C(NH)NR^9R^{11}$, —$R^{10}SO_2R^9$, —$R^{10}SO_2NR^9R^{11}$, —$R^{10}SO_2NHCOR^9$, —$R^{10}NR^7R^8$, —$R^{10}NR^7Ay$, —$R^{10}NHC(NH)NR^9R^{11}$, cyano, nitro and azido; or two adjacent $R^6$ groups together with the atoms to which they are bonded form a $C_{5-6}$ cycloalkyl or a 5- or 6-membered heterocyclic group containing 1 or 2 heteroatoms; or $R^6$ is in the 6 position and $R^6$ and $R^1$ together with the atoms to which they are bonded form a $C_{5-6}$ cycloalkyl or a 5- or 6-membered heterocyclic group containing 1 or 2 heteroatoms;

wherein when Y is CH, $R^3$ is not —$NR^7Ay$;

and pharmaceutically acceptable salts, solvates and physiologically functional derivatives thereof.

Compounds of formula (I) include those compounds defined wherein at least one of $R^1$ and $R^2$ contain an aryl, heterocyclic or heteroaryl moiety. The groups Ay, Het, —$NR^7Ay$, —NHHet, —$NHR^{10}$Ay, —$NHR^{10}$Het, —OAy, —OHet, —$OR^{10}$Het, —$S(O)_nAy$, —$S(O)_n$Het and —$R^{10}NR^7Ay$ are examples of groups containing an aryl, heterocyclic or heteroaryl moiety. In one embodiment, the compounds of the present invention include those compounds defined wherein at least one of $R^1$ and $R^2$ contain a heterocyclic or heteroaryl moiety such as Het, —NHHet, —$NHR^{10}$Het, —OHet, —$OR^{10}$Het and —$S(O)_n$Het.

Another class of compounds of formula (I) includes those compounds defined wherein $R^1$ does not contain an aryl, heterocyclic or heteroaryl moiety. In this embodiment $R^1$ is typically halo or —$NR^7R^8$. In another class of compounds of formula (I) $R^2$ does not contain an aryl, heterocyclic or heteroaryl moiety. In this embodiment, $R^2$ is typically selected from the group consisting of halo, alkyl, alkenyl, cycloalkyl, cycloalkenyl, —$OR^7$, —$S(O)_nR^9$, —$S(O)_nNR^7R^8$, —$NR^7R^8$ and —$R^{10}NR^7R^8$. In another class of compounds of formula (I), $R^1$ does not contain a heterocyclic or heteroaryl moiety but may contain an aryl moiety. In this embodiment, $R^1$ is typically selected from the group consisting of halo, Ay, —$NR^7R^8$, —$NR^7Ay$ and —$NHR^{10}Ay$. In yet another class of compounds of formula (I), $R^2$ does not contain a heterocyclic or heteroaryl moiety but may contain an aryl moiety. In this embodiment, $R^2$ is typically selected from the group consisting of halo, alkyl, alkenyl, cycloalkyl, cycloalkenyl, Ay, —$OR^7$, —OAy, —$S(O)_nR^9$, —$S(O)_nAy$, —$S(O)_nNR^7R^8$, —$NR^7R^8$, —$NHR^{10}$Ay, —$R^{10}NR^7R^8$ and —$R^{10}NR^7Ay$.

In one embodiment, $R^1$ is selected from the group consisting of halo, Ay, Het, —$NR^7R^8$, —NHHet, —$NHR^{10}Ay$ and —$NHR^{10}$Het, or any subset thereof. More particularly, $R^1$ is selected from the group consisting of Het, —$NR^7R^8$, —NHHet and —$NHR^{10}$Het, or any subset thereof. In one embodiment, compounds of formula (I) are defined wherein $R^1$ is —$NR^7R^8$ or Het.

More specifically, $R^1$ may be selected from the group consisting of Cl, Ay, halo-substitited Ay, —$NH_2$, —NH-alkyl, —NH-cycloalkyl, —N(alkyl)(alkyl), Het, —Nalkyl-O-alkyl, and NHAy, or any subset thereof. Specific examples of some particular $R^1$ groups are selected from the group consisting of Cl, 4-fluorophenyl, —$NH_2$, —NH-methyl, —$N(CH_3)_2$, —NH-cyclopentyl, —NH-cyclopropyl, —NH-isopropyl, —NH-phenyl, —$N(CH_2)OCH_3$, and pyrrolidine, or any subset thereof.

In one embodiment, $R^2$ is selected from the group consisting of Het, —$OR^7$, —OAy, —OHet, —$OR^{10}$Het, —S(O)$_n$R$^9$, —S(O)$_n$Ay, —NR$^7$R$^8$, —NHHet and —NHR$^{10}$Het, or any subset thereof. More particularly, R$^2$ is selected from the group consisting of Het, —NR$^7$R$^8$, —NH-Het and NHR$^{10}$Het, or any subset thereof. In one embodiment, R$^2$ is selected from the group consisting of Het, —NR$^7$R$^8$ and —NHHet, or any subset thereof. In one embodiment, R$^2$ is —NR$^7$R$^8$.

In one embodiment, R$^2$ is selected from the group consisting of —NH$_2$, —NH-alkyl, —NH-cycloalkyl, —N(alkyl)(alkyl), Het (e.g., pyrrolidine), —NHHet and —NH-alkyl-Het, or any subset thereof. More particularly, R$^2$ is selected from the group consisting of —NH-alkyl and —NH-cycloalkyl, or any subset thereof.

Specific examples of some particular R$^2$ groups are selected from the group consisting of —NH$_2$, —NH-methyl, —NH-ethyl, —NH-propyl, —NH-isopropyl, —NH-cyclopropyl, —NH-butyl, —NH-isobutyl, —NH-cyclobutyl, —NH-cyclopentyl, —NH-cyclohexyl, —NH(CH$_2$)$_2$OCH$_3$, and pyrrolidine (e.g., pyrrolidine bonded through N).

In one embodiment, R$^7$ and R$^8$ are each the same or different and are independently selected from the group consisting of H, alkyl, cycloalkyl, R$^{10}$-cycloalkyl, —R$^{10}$OR$^9$, —R$^{10}$NR$^9$R$^{11}$, —C(O)R$^9$, and R$^{10}$CO$_2$R$^9$, or any subset thereof. More particularly, R$^7$ and R$^8$ are each the same or different and are independently selected from the group consisting of H, alkyl, cycloalkyl and R$^{10}$-cycloalkyl, or any subset thereof. In one embodiment, R$^7$ and R$^8$ are each the same or different and are independently selected from the group consisting of H, alkyl and cycloalkyl or any subset thereof.

The group —R$^{10}$(OR$^{10}$)$_w$ in the definition of R$^9$ and R$^{11}$ refers to a linear PEG chain. In one embodiment, R$^9$ and R$^{11}$ are each the same or different and are independently selected from the group consisting of H, alkyl, cycloalkyl, and —R$^{10}$-cycloalkyl, or any subset thereof. More particularly, R$^9$ and R$^{11}$ are each the same or different and are each independently selected from the group consisting of H and alkyl, or any subset thereof.

In one embodiment, R$^{10}$ is alkyl or cycloalkyl; more particularly alkyl.

In one class of compounds of formula (I), Y is CH. In another class of compounds of formula (I), Y is N.

In another embodiment, the compounds of formula (I) include those compounds defined where at least one of R$^3$ and R$^4$ contains a heterocyclic or heteroaryl moiety. A further embodiment includes those compounds of formula (I) where neither R$^3$ nor R$^4$ contain a heterocyclic or heteroaryl moiety. From the embodiments described above with respect to R$^1$ and R$^2$, one skilled in the art can readily determine the groups defining R$^3$ and R$^4$ which contain or exclude aryl, heterocyclic and/or heteroaryl moieties.

In one embodiment, R$^3$ is selected from the group consisting of H, halo, alkyl, Ay, —OR$^7$, —CO$_2$R$^7$, —NR$^7$R$^8$, —R$^{10}$OR$^7$ and —R$^{10}$NR$^7$R$^8$, or any subset thereof. More particularly, R$^3$ is selected from the group consisting of H, halo, alkyl, —OR$^7$ and —NR$^7$R$^8$, or any subset thereof. In one particular embodiment R$^3$ is H or alkyl. In one embodiment R$^3$ is H.

In one embodiment, R$^4$ is selected from the group consisting of H, halo, alkyl, Ay, —OR$^7$, —CO$_2$R$^7$, —NR$^7$R$^8$, —R$^{10}$OR$^7$ and —R$^{10}$NR$^7$R$^8$, or any subset thereof. More particularly R$^4$ is selected from the group consisting of H, halo, alkyl, —OR$^7$ and —NR$^7$R$^8$, or any subset thereof. In one particular embodiment, R$^4$ is H or alkyl. In one embodiment R$^4$ is H.

In one embodiment q is 0, 1 or 2. In one particular embodiment, q is 0. In another particular embodiment, q is 1. In one embodiment, q is 2 and optionally two adjacent R$^5$ groups together with the atoms which they are bonded, they form a C$_{5-6}$ cycloalkyl or aryl. The phrase "two adjacent R$^5$ groups" refers to two R$^5$ groups, each bonded to adjacent carbon atoms on the phenyl ring. In the embodiment where two adjacent R$^5$ groups together with the atoms to which they are bonded form a cycloalkyl or aryl, q is typically 2, 3, 4 or 5; more typically 2.

R$^5$ may be in the ortho, meta and/or para position.

Another class of compounds of formula (I) includes those compounds defined wherein at least one R$^5$ group contains an aryl, heterocyclic or heteroaryl moiety (in one embodiment, a heterocyclic or heteroaryl moiety) and two adjacent R$^5$ groups together with the atoms to which they are bonded do not form a C$_{5-6}$ cycloalkyl or aryl. Another class of compounds of formula (I) includes those compounds defined wherein q is 3, 4 or 5, at least one R$^5$ group contains an aryl, heterocyclic or heteroaryl moiety (in one embodiment, a heterocyclic or heteroaryl moiety) and two adjacent R$^5$ groups together with the atoms to which they are bonded do form a C$_{5-6}$ cycloalkyl or aryl. Another class of compounds of formula (I) includes those compounds defined where no R$^5$ group contains an aryl, heterocyclic or heteroaryl moiety (or in one embodiment no R$^5$ group contains a heterocyclic or heteroaryl moeity) and two adjacent R$^5$ groups together with the atoms to which they are bonded do not form a C$_{5-6}$ cycloalkyl or aryl. Another class of compounds of formula (I) includes those compounds defined wherein q is 2, 3, 4 or 5, no R$^5$ group contains an aryl, heterocyclic or heteroaryl moiety (or in one embodiment no R$^5$ group contains a heterocyclic or heteroaryl moiety) and two adjacent R$^5$ groups together with the atoms to which they are bonded do form a C$_{5-6}$ cycloalkyl or aryl.

In the embodiments where two adjacent R$^5$ groups together with the atoms to which they are bonded do form a cycloalkyl or aryl, each R$^5$ group may be the same or different and is typically selected from the group consisting of alkyl and alkenyl. For example, in one embodiment, two adjacent R$^5$ groups are alkyl and together with the atoms to which they are bonded, they form a cycloalkyl group such as:

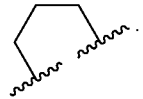

From this example, additional embodiments, including those where two adjacent R$^5$ groups together with the atoms to which they are bonded form an aryl group, can be readily ascertained by those skilled in the art. In one particular embodiment, the compounds of formula (I) are defined wherein two adjacent R$^5$ groups together with the atoms to which they are bonded do not form a C$_{5-6}$ cycloalkyl or aryl.

In one embodiment, each R$^5$ group is the same or different and is independently selected from the group consisting of halo, alkyl, alkenyl, Ay, Het, —OR$^7$, —OAy, —CO$_2$R$^9$, —C(O)NR$^7$R$^8$, —C(O)NR$^7$Ay, —S(O)$_2$NR$^7$R$^8$, —NR$^7$R$^8$, —NR$^7$Ay, —NHR$^{10}$Ay, cyano, nitro and azido, or any subset thereof. More particularly, each R$^5$ group is the same or different and is independently selected from the group consisting of halo, alkyl, alkenyl, Ay, Het, —OR⁷, —NR⁷R⁸, —NR⁷Ay, cyano, nitro and azido, or any subset thereof. In one particular embodiment, each R⁵ group is the same or different and is independently selected from the group consisting of halo, alkyl, —OR⁷, —NR⁷R⁸ and cyano, or any subset thereof.

More specifically, in one embodiment, the compounds of formula (I) are defined where R⁵ is H, halo (e.g., fluoro, chloro or bromo), alkyl (e.g., methyl), O-alkyl (e.g., O-methyl, O-isobutyl, and

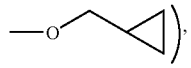

cyano, —NH—CH₃, and —N(CH₃)₂, or any subset thereof.

In particular, p is 1 or 2, more particularly 1.

R⁶ may be in the 4, 5 or 6 position. In one embodiment, p is 1 and R⁶ is in the C-5 position. In one embodiment, p is 1 and R⁶ is in the C-6 position. In one embodiment p is 2 and one R⁶ is in the C-5 position and one R⁶ is in the C-6 position (thus defining a class of compounds of formula (I) having two adjacent R⁶ groups).

Another class of compounds of formula (I) includes those compounds defined wherein at least one R⁶ group contains an aryl, heterocyclic or heteroaryl moiety (in one embodiment, a heterocyclic or heteroaryl moiety) and two adjacent R⁶ groups together with the atoms to which they are bonded do not form a C₅₋₆ cycloalkyl or a 5- or 6-membered heterocyclic group containing 1 or 2 heteroatoms. Another class of compounds of formula (I) includes those compounds defined wherein p is 3, at least one R⁶ group contains an aryl, heterocyclic or heteroaryl moiety (in one embodiment, a heterocyclic or heteroaryl moiety) and two adjacent R⁶ groups together with the atoms to which they are bonded do form a C₅₋₆ cycloalkyl or a 5- or 6-membered heterocyclic group containing 1 or 2 heteroatoms. A particular class of compounds of formula (I) includes those compounds defined where no R⁶ group contains an aryl, heterocyclic or heteroaryl moiety (or in one embodiment no R⁶ group contains a heterocyclic or heteroaryl moeity) and two adjacent R⁶ groups together with the atoms to which they are bonded do not form a C₅₋₆ cycloalkyl or a 5- or 6-membered heterocyclic group containing 1 or 2 heteroatoms. Another class of compounds of formula (I) includes those compounds defined wherein p is 2 or 3. no R⁶ group contains an aryl, heterocyclic or heteroaryl moiety (or in one embodiment no R⁶ group contains a heterocyclic or heteroaryl moiety) and two adjacent R⁶ groups together with the atoms to which they are bonded do form a C₅₋₆ cycloalkyl or a 5- or 6-membered heterocyclic group containing 1 or 2 heteroatoms.

In the embodiments where two adjacent R⁶ groups (or R⁶ and R¹) together with the atoms to which they are bonded form a C₅₋₆ cycloalkyl or a 5- or 6-membered heterocyclic group containing 1 or 2 heteroatoms, each R⁶ group may be the same or different and is typically selected from the group consisting of alkyl, alkenyl, —OR⁷, —NR⁷R⁸ and —S(O)ₙR⁹. For example, in one embodiment two adjacent R⁶ groups are —OR⁷ and together with the atoms to which they are bonded, they form a heterocyclic group such as:

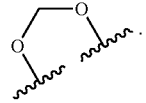

In another embodiment, two adjacent R⁶ groups are alkyl and together with the atoms to which they are bonded, they form a cycloalkyl group such as:

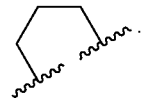

In another embodiment two adjacent R⁶ groups are defined as —OR⁷, —NR⁷R⁸ respectively and together with the atoms to which they are bonded, they form a heterocyclic group such as:

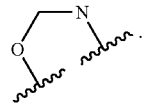

From these examples, additional embodiments can be readily ascertained by those skilled in the art, as can embodiments wherein R⁶ is in the 6 position and R⁶ and R¹ together with the atoms to which they are bonded they form a C₅₋₆cycloalkyl or a 5- or 6-membered heterocyclic group. In one particular embodiment, two R⁶ groups or R⁶ and R¹ together with the atoms to which they are bonded do not form a C₅₋₆ cycloalkyl or a 5- or 6-membered heterocyclic group.

In one embodiment, each R⁶ is the same or different and is independently selected from the group consisting of halo, alkyl, Ay, Het, —OR⁷, —OAy, —OHet, —C(O)Het, —CO₂R⁹, —C(O)NR⁷R⁸, —C(O)NR⁷Ay, —C(O)NHR¹⁰Het, —NR⁷R⁸, —NR⁷Ay, —NHHet, —NHR¹⁰Ay, —NHR¹⁰Het, —R¹⁰OR⁹ and cyano, or any subset thereof. More particularly, each R⁶ is the same or different and is independently selected from the group consisting of halo, alkyl, —OR⁷, —C(O)Het, —C(O)NR⁷R⁸, —C(O)NHR¹⁰et, —NR⁷R⁸, —NR⁷Ay, NHHet, —NHR¹⁰Ay, —NHR¹⁰Het, —R¹⁰OR⁹ and cyano, or any subset thereof. In one particular embodiment, each R⁶ is the same or different and is independently selected from the group consisting of halo, alkyl, —C(O)NR⁷R⁸, —NR⁷R⁸, —NR⁷Ay, —NHHet, —NHR¹⁰Ay, and —NHR¹⁰Het, or any subset thereof.

More specifically, in one embodiment, R⁶ is selected from the group consisting of Cl, Br, —O-alkyl, —O-alkyl-O-alkyl, —S-alkyl, —NH₂, —NH-alkyl, —NHR¹⁰OR⁹, —NH-cycloalkyl, and —NH—SO₂-alkyl, or any subset thereof. In one embodiment, R⁶ is selected from the group consisting of Cl, Br, —O—CH₃, —O—(CH₂)₂—O—CH₃, —S—CH₃, —NH₂, —NHCH(CH₃)₂, —NHcyclopropyl, —NHcyclopentyl, —NH(CH₂)₂—O—CH₃ and —NH—SO₂—CH₃, or any subset thereof. In one embodiment, R⁶ is halo, such as Cl or Br. In one embodiment R⁶ is trifluoromethyl.

It is to be understood that the present invention includes all combinations and subsets of the particular groups defined hereinabove.

Specific compounds of formula (I) include but are not limited to:

N-Cyclopentyl-2-(4-fluorophenyl)-3-[2-(1-pyrrolidinyl)-4-pyrimidinyl]-6-(trifluoromethyl)pyrazolo[1,5-a]pyridin-7-amine;

N-Cyclopentyl-3-[2-(cyclopentylamino)-4-pyrimidinyl]-2-(4-fluorophenyl)-6-(trifluoromethyl)pyrazolo[1,5-a]pyridin-7-amine;

Ethyl 7-(cyclopentylamino)-3-[2-(cyclopentylamino)-4-pyrimidinyl]-2-(4-fluorophenyl)pyrazolo[1,5-a]pyridine-6-carboxylate;

7-(Cyclopentylamino)-3-[2-(cyclopentylamino)-4-pyrimidinyl]-2-(4-fluorophenyl)pyrazolo[1,5-a]pyridine-6-carboxylic acid;

N-Cyclopentyl-3-[2-(cyclopentylamino)-4-pyrimidinyl]-2-(4-fluorophenyl)-6-(1-pyrrolidinylcarbonyl)pyrazolo[1,5-a]pyridin-7-amine;

7-(Cyclopentylamino)-3-[2-(cyclopentylamino)-4-pyrimidinyl]-2-(4-fluorophenyl)-N,N-dimethylpyrazolo[1,5-a]pyridine-6-carboxamide;

7-(Cyclopentylamino)-3-[2-(cyclopentylamino)-4-pyrimidinyl]-2-(4-fluorophenyl)-N-hydroxypyrazolo[1,5-a)pyridine-6-carboxamide;

7-(Cyclopentylamino)-3-[2-(cyclopentylamino)-4-pyrimidinyl]-2-(4-fluorophenyl)-N-[2-(4-morpholinyl)ethyl]pyrazolo[1,5-a]pyridine-6-carboxamide;

7-(Cyclopentylamino)-3-[2-(cyclopentylamino)-4-pyrimidinyl]-2-(4-fluorophenyl)-N-[3-(1H-imidazol-1-yl)propyl]pyrazolo[1,5-a]pyridine-6-carboxamide;

7-(Cyclopentylamino)-3-[2-(cyclopentylamino)-4-pyrimidinyl]-2-(4-fluorophenyl)-N-[2-hydroxy-1-(hydroxymethyl)ethyl]pyrazolo[1,5-a]pyridine-6-carboxamide;

[7-(Cyclopentylamino)-3-(2-(cyclopentylamino)-4-pyrimidinyl]-2-(4-fluorophenyl)pyrazolo[1,5-a]pyridin-6-yl]methanol;

N-Cyclopentyl-4-[5,7-dichloro-2-(4-fluorophenyl)pyrazolo[1,5-a]pyridin-3-yl]-2-pyrimidinamine;

N-{4-[5-Chloro-7-(cyclopentylamino)-2-(4-fluorophenyl)pyrazolo[1,5-a]pyridin-3-yl]-2-pyrimidinyl}-N-cyclopentylamine;

$N^6,N^7$-Dicyclopentyl-3-[2-(cyclopentylamino)-4-pyrimidinyl]-2-(4-fluorophenyl)-pyrazolo[1,5-a]pyridine-5,7-diamine;

5-Chloro-3-[2-(cyclopentylamino)-4-pyrimidinyl]-2-(4-fluorophenyl)-N-isopropylpyrazolo[1,5-a]pyridin-7-amine;

3-[2-(Cyclopentylamino)-4-pyrimidinyl]-2-(4-fluorophenyl)-$N^5,N^7$-diisopropyl-pyrazolo[1,5-a]pyridine-5,7-diamine;

N-Cyclopentyl-4-[5,7-dichloro-2-(4-methoxyphenyl)pyrazolo[1,5-a]pyridin-3-yl]-2-pyrimidinamine;

N-{4-[5-Chloro-7-(cyclopentylamino)-2-(4-methoxyphenyl)pyrazolo[1,5-a]pyridin-3-yl]-2-pyrimidinyl}-N-cyclopentylamine;

N-Cyclopentyl-4-[5,7-dichloro-2-(4-methoxyphenyl)pyrazolo[1,5-a]pyridin-3-yl]-2-pyrimidinamine;

N-{4-[5-Chloro-7-(cyclopentylamino)-2-(4-methoxyphenyl)pyrazolo[1,5-a]pyridin-3-yl]-2-pyrimidinyl}-N-cyclopentylamine;

5-Chloro-N-cyclopentyl-3-[2-(cyclopentylamino)pyrimidin-4-yl]-2-(3-methylphenyl)pyrazolo[1,5-a]pyridin-7-amine;

5-Chloro-3-[2-(cyclopentylamino)pyrimidin-4-yl]-N-cyclopropyl-2-(3-methylphenyl)pyrazolo[1,5-a]pyridin-7-amine;

5-Chloro-N-cyclopentyl-3-[2-(cyclopropylamino)pyrimidin-4-yl]-2-(3-methylphenyl)pyrazolo[1,5-a]pyridin-7-amine;

5-Chloro-3-[2-(cyclopentylamino)-4-pyrimidinyl]-N-cyclopropyl-2-(4-fluorophenyl)pyrazolo[1,5-a]pyridin-7-amine;

4-[5-Chloro-2-(4-fluorophenyl)-7-(4-methyl-1-piperazinyl)pyrazolo[1,5-a]pyridin-3-yl]-N-cyclopentyl-2-pyrimidinamine;

4-[5-Chloro-2-(4-fluorophenyl)-7-(1-piperidinyl)pyrazolo[1,5-a]pyridin-3-yl]-N-cyclopentyl-2-pyrimidinamine;

4-[5-Chloro-2-(4-fluorophenyl)-7-(4-morpholinyl)pyrazolo[1,5-a]pyridin-3-yl]-N-cyclopentyl-2-pyrimidinamine;

N-[5-Chloro-3-[2-(cyclopentylamino)pyrimidin-4-yl]-2-(4-fluorophenyl)pyrazolo[1,5-a]pyridin-7-yl]-N'-cyclopentylguanidine hydrochloride;

5-Chloro-N-cyclopropyl-3-[2-(cyclopropylamino)pyrimidin-4-yl]-2-(4-fluorophenyl)pyrazolo[1,5-a]pyridin-7-amine;

N-cyclopentyl-4-[5,7-dichloro-2-(3-chlorophenyl)pyrazolo[1,5-a]pyridin-3-yl]-2-pyrimidinamine;

N-{4-[5-chloro-2-(3-chlorophenyl)-7-(cyclopentylamino)pyrazolo[1,5-a]pyridin-3-yl]-2-pyrimidinyl}-N-cyclopentylamine;

N-{4-[5-Chloro-7-(cyclopropylamino)-2-(4-methoxyphenyl)pyrazolo[1,5-a]pyridin-3-yl]-2-pyrimidinyl}-N-cyclopentylamine;

4-[5-Chloro-3-[2-(cyclopentylamino)-4-pyrimidinyl]-7-(cyclopropylamino)pyrazolo[1,5-a]pyridin-2-yl]phenol;

5-Chloro-3-[2-(cyclopentylamino)-4-pyrimidinyl]-N-cyclopropyl-2-[4-(cyclopropylmethoxy)phenyl]pyrazolo[1,5-a]pyridin-7-amine;

4-[5-Chloro-3-[2-(cyclopentylamino)-4-pyrimidinyl]-7-(cyclopentylamino)pyrazolo[1,5-a]pyridin-2-yl]phenol;

5-Chloro-3-[2-(cyclopentylamino)-4-pyrimidinyl]-N-cyclopentyl-2-[4-(cyclopropylmethoxy)phenyl]pyrazolo[1,5-a]pyridin-7-amine;

5,7-dichloro-2-(4-methoxyphenyl)-3-[2-(methylthio)pyrimidin-4-yl]pyrazolo[1,5-a]pyridine;

N-{5-Chloro-2-(4-methoxyphenyl)-3-[2-(methylsulfanyl)-4-pyrimidinyl]pyrazolo(1,5-a]pyridin-7-yl}-N-cyclopentylamine;

N-{-Chloro-2-(4-methoxyphenyl)-3-[2-(methylsulfinyl)-4-pyrimidinyl]pyrazolo[1,5-a]pyridin-7-yl}-N-cyclopentylamine;

N-{4-[5-Chloro-7-(cyclopentylamino)-2-(4-methoxyphenyl)pyrazolo[1,5-a]pyridin-3-yl]-2-pyrimidinyl}-N-cyclopropylamine;

4-{5-Chloro-7-(cyclopentylamino)-3-[2-(cyclopropylamino)-4-pyrimidinyl]pyrazolo[1,5-a]pyridin-2-yl}phenol;

N-(4-{5-Chloro-7-(cyclopentylamino)-2-[4-(cyclopropylmethoxy)phenyl]pyrazolo[1,5-a]pyridin-3-yl}-2-pyrimidinyl)-N-cyclopropylamine;

7-Chloro-N-cyclopentyl-3-[2-(cyclopentylamino)pyrimidin-4-yl]-2-(4-fluorophenyl)pyrazolo[1,5-a]pyridin-5-amine;

4,6-Dibromo-N-cyclopentyl-3-[2-(cyclopentylamino)pyrimidin-4-yl]-2-(4-fluorophenyl)pyrazolo[1,5-a]pyridin-7-amine;

4,6-Dibromo-3-[5-bromo-2-(cyclopentylamino)pyrimidin-4-yl]-N-cyclopentyl-2-(4-fluorophenyl)pyrazolo[1,5-a]pyridin-7-amine;

6-Chloro-N-cyclopentyl-3-[2-(cyclopentylamino)pyrimidin-4-yl]-2-(4-fluorophenyl)pyrazolo[1,5-a]pyridin-7-amine;

N-Cyclopentyl-3-[2-(cyclopentylamino)-4-pyrimidinyl]-2-(4fluorophenyl)-5-methoxypyrazolo[1,5-a]pyridin-7-amine; and N-Cyclopentyl-3-[2-(cyclopentylamino)-4-pyrimidinyl]-2-(4-fluorophenyl)-5-(2-methoxyethoxy)pyrazolo[1,5-a]pyridin-7-amine, and pharmaceutically acceptable salts, solvates and physiologically functional derivatives thereof.

Particular compounds of formula (I) include but are not limited to:

N-{4-[5-Chloro-7-(cyclopentylamino)-2-(4-fluorophenyl)pyrazolo[1,5-a]pyridin-3-yl]-2-pyrimidinyl}-N-cyclopentylamine;

$N^5,N^7$-Dicyclopentyl-3-[2-(cyclopentylamino)-4-pyrimidinyl]-2-(4-fluorophenyl)pyrazolo[1,5-a]pyridine-5,7-diamine;

5-Chloro-3-[2-(cyclopentylamino)-4-pyrimidinyl]-2-(4-fluorophenyl)-N-isopropylpyrazolo[1,5-a]pyridin-7-amine;

3-[2-(Cyclopentylamino)-4-pyrimidinyl]-2-(4-fluorophenyl)-$N^5,N^7$-diisopropylpyrazolo[1,5-a]pyridine-5,7-diamine;

N-{4-[5-Chloro-7-(cyclopentylamino)-2-(4-methoxyphenyl)pyrazolo[1,5-a]pyridin-3-yl]-2-pyrimidinyl}-N-cyclopentylamine;

5-Chloro-N-cyclopentyl-3-[2-(cyclopentylamino)pyrimidin-4-yl]-2-(3-methylphenyl)pyrazolo[1,5-a]pyridin-7-amine;

5-Chloro-3-[2-(cyclopentylamino)pyrimidin-4-yl]-N-cyclopropyl-2-(3-methylphenyl)pyrazolo[1,5-a]pyridin-7-amine;

5-Chloro-N-cyclopentyl-3-[2-(cyclopropylamino)pyrimidin-4-yl]-2-(3-methylphenyl)pyrazolo[1,5-a]pyridin-7-amine;

5-Chloro-3-[2-(cyclopentylamino)-4-pyrimidinyl]-N-cyclopropyl-2-(4-fluorophenyl)pyrazolo[1,5-a]pyridin-7-amine;

4-[5-Chloro-2-(4-fluorophenyl)-7-(4-methyl-1-piperazinyl)pyrazolo[1,5-a]pyridin-3-yl]-N-cyclopentyl-2-pyrimidinamine;

4-[5-Chloro-2-(4-fluorophenyl)-7-(1-piperidinyl)pyrazolo[1,5-a]pyridin-3-yl]-N-cyclopentyl-2-pyrimidinamine;

4-[5-Chloro-2-(4-fluorophenyl)-7-(4-morpholinyl)pyrazolo[1,5-a]pyridin-3-yl]-N-cyclopentyl-2-pyrimidinamine;

N-[5-Chloro-3-[2-(cyclopentylamino)pyrimidin-4-yl]-2-(4-fluorophenyl)pyrazolo[1,5-a]pyridin-7-yl]-N'-cyclopentylguanidine hydrochloride;

N-{4-[5-chloro-2-(3-chlorophenyl)-7-(cyclopentylamino)pyrazolo[1,5-a]pyridin-3-yl]-2-pyrimidinyl}-N-cyclopentylamine;

N-{4-[5-Chloro-7-(cyclopropylamino)-2-(4-methoxyphenyl)pyrazolo[1,5-a]pyridin-3-yl]-2-pyrimidinyl}-N-cyclopentylamine;

5-Chloro-3-[2-(cyclopentylamino)-4-pyrimidinyl]-N-cyclopropyl-2-[4-(cyclopropylmethoxy)phenyl]pyrazolo[1,5-a]pyridin-7-amine;

4-[5-Chloro-3-[2-(cyclopentylamino)-4-pyrimidinyl]-7-(cyclopentylamino)pyrazolo[1,5-a]pyridin-2-yl]phenol;

5-Chloro-3-[2-(cyclopentylamino)-4-pyrimidinyl]-N-cyclopentyl-2-[4-(cyclopropylmethoxy)phenyl]pyrazolo[1,5-a]pyridin-7-amine;

N-{4-[5-Chloro-7-(cyclopentylamino)-2-(4-methoxyphenyl)pyrazolo[1,5-a]pyridin-3-yl]-2-pyrimidinyl}-N-cyclopropylamine;

6-Chloro-N-cyclopentyl-3-[2-(cyclopentylamino)pyrimidin-4-yl]-2-(4-fluorophenyl)pyrazolo[1,5-a]pyridin-7-amine;

N-Cyclopentyl-3-[2-(cyclopentylamino)-4-pyrimidinyl]-2-(4-fluorophenyl)-5-methoxypyrazolo[1,5-a]pyridin-7-amine; and N-Cyclopentyl-3-[2-(cyclopentylamino)-4-pyrimidinyl]-2-(4-fluorophenyl)-5-(2-methoxyethoxy)pyrazolo[1,5-a]pyridin-7-amine, and pharmaceutically accetpable salts, solvates and physiologically functional derivatives thereof.

It will be appreciated by those skilled in the art that the compounds of the present invention may also be utilized in the form of a pharmaceutically acceptable salt or solvate or physiologically functional derivative thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic (mesylate), naphthalene-2-sulfonic, benzenesulfonic hydroxynaphthoic, hydroiodic, malic, steroic, tannic and the like. In one embodiment, the compounds of formula (I) are in the form of the mesylate salt. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid.

The term "physiologically functional derivative" as used herein refers to any pharmaceutically acceptable derivative of a compound of the present invention, for example, an ester or an amide of a compound of formula (I), which upon administration to an animal, particularly a mammal, such as a human, is capable of providing (directly or indirectly) a compound of the present invention or an active metabolite thereof. See, for example, Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes described below for the preparation of compounds of formula (I), certain intermediates, may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), varicella zoster virus NWZV), human herpes virus 6 (HHV-6), human herpes virus 7 (HHV-7), and human herpes virus 8 (HHV-8). Thus, the compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from RFA, viral infection, particularly by CMV and/or HHV-6 of the patient plays a pivotal role in the proliferation of the smooth muscle cells in the coronary vessel treated. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of conditions or diseases associated with hepatitis B or hepatitis C viruses, human papilloma virus (HPV) and HIV.

The present invention provides a method for the treatment or prophylaxis of a viral infection in an animal such as a mammal (e.g., a human), particularly a herpes viral infection, which method comprises administering to the animal a therapeutically effective amount of the compound of formula (I).

As used herein, the term "prophylaxis" refers to the complete prevention of infection, the prevention of occurrence of symptoms in an infected subject, the prevention of recurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject.

As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes virus infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the comound of formula (I) in the preparation of a medicament for the treatment of conditions or disease associated with a herpes viral infection; and the use of the compound of formula (I). in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in conventional manner in admixture with one or more physiologically acceptable carriers or diluents.

While it is possible that compounds of the present invention may be therapeutically administered as the raw chemical, it is common to present the active ingredient as a pharmaceutical formulation or composition. The pharmaceutical composition may comprise a pharmaceutically acceptable carrier or diluent. The carrier(s) or diluent(s) must be "acceptable" in the sense of being compatible with the other ingredients of the formulation and not deleterious to the recipient thereof.

Accordingly, the present invention further provides for a pharmaceutical formulation or composition comprising a compound of formula (I). In one embodiment, the pharmaceutical composition further comprises one or more pharmaceutically acceptable carriers or diluents and optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation. Formulations suitable for oral administration may be presented as discrete units such as capsules (including soft-gel capsules), cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Liquid preparations may also be formulated as soft-gel capsules for oral administration, e.g., containing conventional soft-gel excipients such as polyethylene glycol.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described. Formulations for rectal administration may be presented as a suppository with the usual carriers such as cocoa butter, hard fat or polyethylene glycol.

Formulations suitable for topical (e.g., dermal) or intranasal application include ointments, creams, lotions, pastes, gels, sprays, aerosols and oils. Suitable carriers for such formulations include petroleum jelly, lanolin, polyethyleneglycols, alcohols, and combinations thereof.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, particularly 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, famcyclovir, gancyclovir, docosanol, miribavir, amprenavir, lamivudine, zidovudine, and abacavir. Particular antiviral agents for combining with the compounds of the present invention include aciclovir and valaciclovir. Thus the present invention provides in a further aspect, a combination comprising a compound of formula (I) and an antiviral agent selected from the group consisting of aciclovir and valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein Y is N, $R^2$ is selected from the group consisting of alkyl, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n$Het, —$S(O)_nNR^7R^8$, —$NR^7R^8$, —NHHet, —$NHR^{10}$Ay, —$NHR^{10}$Het, —$R^{10}NR^7R^8$ and —$R^{10}NR^7$Ay; and $R^3$ and $R^4$ are H, may be conveniently prepared by the process outlined in Scheme 1 below.

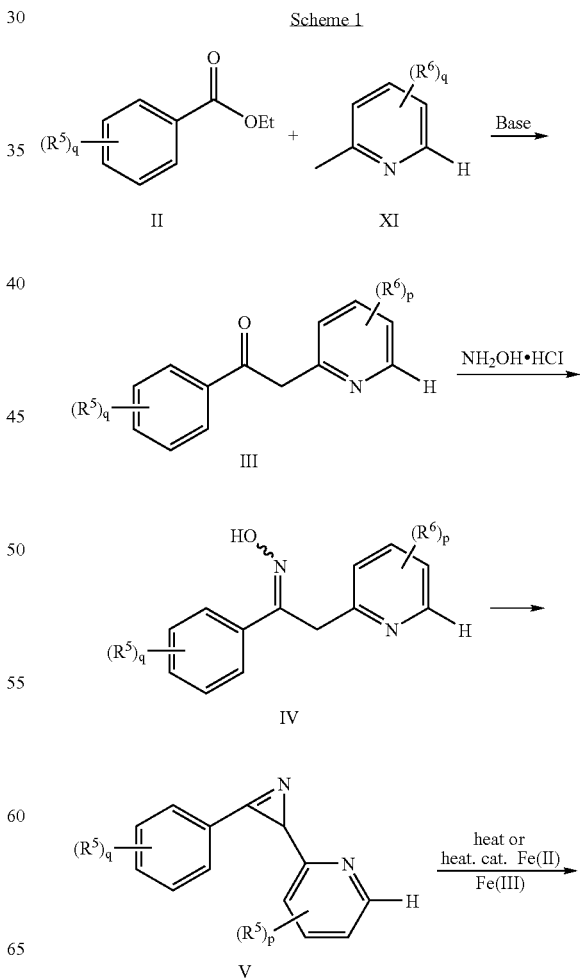

Scheme 1

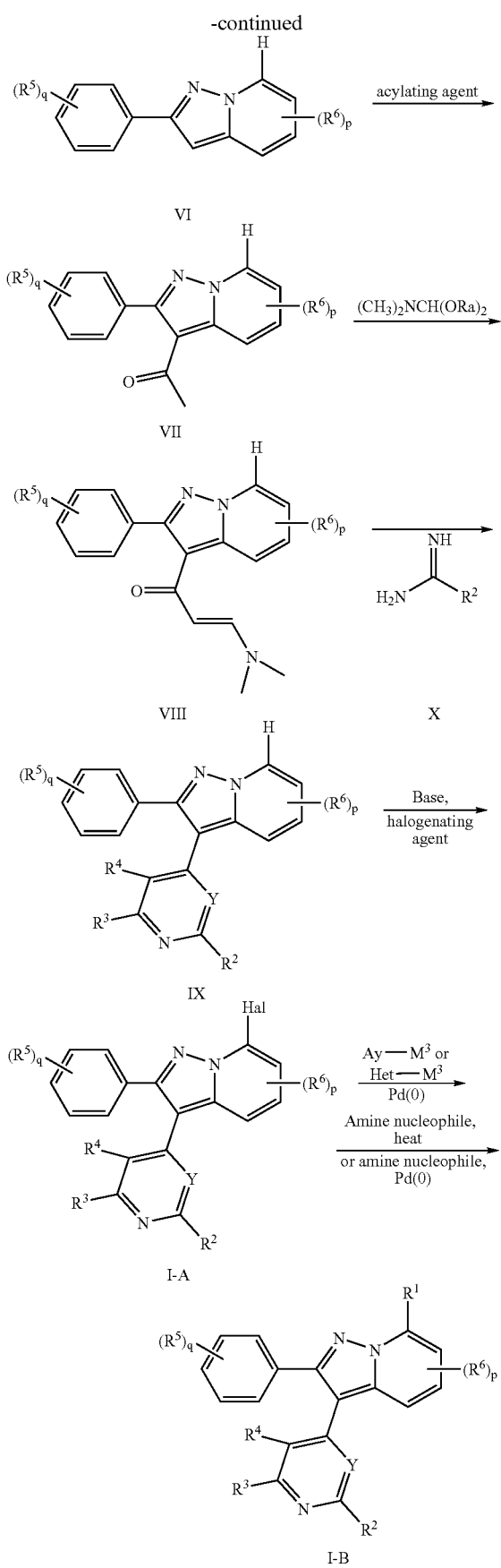

wherein:
R[1] is selected from the group consisting of Ay, Het, —NR[7]R[8], —NR[7]Ay, —NHHet, —NHR[10]Ay and —NHR[10]Het;
each R[7] and R[8] are the same or different and are independently selected from the group consisting of H, alkyl, alkenyl, cycloalkyl, cycloalkenyl, —OR[9], —C(O)R[9], —CO$_2$R[9], —C(O)NR[9]R[11], —C(S)NR[9]R[11], —C(NH)NR[9]R[11], —SO$_2$R[10], —SO$_2$NR[9]R[11], —R[10]cycloalkyl, —R[10]OR[9], —CH(R[10]OR[9])$_2$, —R[10]C(O)R[9], —R[10]CO$_2$R[9], —R[10]C(O)NR[9]R[11], —R[10]C(S)NR[9]R[11], —R[10]C(NH)NR[9]R[11], —R[10]SO$_2$R[10], —R[10]SO$_2$NR[9]R[11], —R[10]SO$_2$NHCOR[9], —R[10]NR[9]R[11], —R[10]NHCOR[9], —R[10]NHSO$_2$R[9] and —R[10]NHC(NH)NR[9]R[11] and;
each R[9] and R[11] are the same or different and are independently selected from the group consisting of H, alkyl, cycloalkyl, —R[10]cycloalkyl, —R[10]OH, —R[10](OR[10])$_w$ where w is 1–10, and —R[10]NR[10]R[10];
each R[10] is the same or different and is independently selected from the group consisting of alkyl, alkenyl, alkynyl, cycloalkyl and cycloalkenyl;
Ay is aryl;
Het is a 5- or 6-membered heterocyclic or heteroaryl group;
n is 0, 1 or 2;
R[2] is selected from the group consisting of alkyl, alkenyl, cycloalkyl, cycloalkenyl, Ay, Het, —OR[7], —OAy, —OHet, —OR[10]Het, —S(O)$_n$R[9], —S(O)$_n$Ay, —S(O)$_n$Het, —S(O)$_n$NR[7]R[8], —NR[7]R[8], —NHHet, —NHR[10]Ay, —NHR[10]Het, —R[10]NR[7]R[8] and —R[10]NR[7]Ay;
Y is N;
R[3] and R[4] are both H;
q is 0, 1, 2, 3, 4 or 5;
each R[5] is the same or different and is independently selected from the group consisting of halo, alkyl, alkenyl, alkynyl, cycloalkyl, cycloalkenyl, Ay, Het, —OR[7], —OAy, —OHet, —C(O)R[9], —C(O)Ay, —C(O)Het, —CO$_2$R[9], —C(O)NR[7]R[8], —C(O)NR[7]Ay, —C(O)NHR[10]Het, —C(S)NR[9]R[11], —C(NH)NR[7]R[8]—C(NH)NR[7]Ay, —S(O)$_n$R[9], —S(O)$_2$NR[7]R[8], —S(O)$_2$NR[7]Ay, —NR[7]R[8], —NR[7]Ay, —NHHet, —NHR[10]Ay, —NHR[10]Het, —R[10]cycloalkyl, —R[10]OR[9], —R[10]C(O)R[9], —R[10]CO$_2$R[9], —R[10]C(O)NR[9]R[11], —R[10]C(S)NR[9]R[11], —R[10]C(NH)NR[9]R[11], —R[10]SO$_2$R[9], —R[10]SO$_2$NR[9]R[11], —R[10]SO$_2$NHCOR[9], —R[10]NR[7]R[8], —R[10]NR[7]Ay, —R[10]NHC(NH)NR[9]R[11], cyano, nitro and azido; or
two adjacent R[5] groups together with the atoms to which they are bonded form a C$_{5-6}$ cycloalkyl or aryl;
p is 1, 2 or 3;
each R[6] is the same or different and is independently selected from the group consisting of halo, alkyl, alkenyl, alkynyl, cycloalkyl, cycloalkenyl, Ay, Het, —OR[7], —OAy, —OHet, —OR[10]Ay, —OR[10]Het, —C(O)R[9], —C(O)Ay, —C(O)Het, —CO$_2$R[9], —C(O)NR[7]R[8], —C(O)NR[7]Ay, —C(O)NHR[10]Ay, —C(O)NHR[10]Het, —C(S)NR[9]R[11], —C(NH)NR[7]R[8], —C(NH)NR[7]Ay, —S(O)$_n$R[9], —S(O)$_n$Ay, —S(O)$_n$Het, —S(O)$_2$NR[7]R[8], —S(O)$_2$NR[7]Ay, —NR[7]R[8], —NR[7]Ay, —NHHet, —NHR[10]Ay, —NHR[10]Het, —R[10]cycloalkyl, —R[10]Ay, —R[10]Het, —R[10]OR[9], —R[10]—O—C(O)R[9], —R[10]—O—C(O)Ay, —R[10]—O—C(O)Het, —R[10]—O—S(O)$_n$R[9], —R[10]C(O)R[9], —R[10]CO$_2$R[9], —R[10]C(O)NR[9]R[11], —R[10]C(S)NR[9]R[11], —R[10]C(NH)NR[9]R[11], —R[10]SO$_2$R[9], —R[10]SO$_2$NR[9]R[11], —R[10]SO$_2$NHCOR[9], —R$_{10}$NR[7]R[8], —R[10]NR[7]Ay, —R[10]NHC(NH)NR[9]R[11], cyano, nitro and azido; or two adjacent $R^6$ groups together with the atoms to which they are bonded form a $C_{5-6}$ cycloalkyl or a 5- or 6-membered heterocyclic group containing 1 or 2 heteroatoms; or $R^6$ is in the 6 position and $R^6$ and $R^1$ together with the atoms to which they are bonded form a $C_{5-6}$ cycloalkyl or a 5- or 6-membered heterocyclic group containing 1 or 2 heteroatoms;

Ra is alkyl or cycloalkyl;

Hal is halo; and $M^3$ is —B(OH)$_2$, —B(ORa)$_2$, —B(Ra)$_2$, —Sn(Ra)$_3$, Zn-halide, Zn—Ra or Mg-halide where halide is halo.

Generally, the process for preparing the compounds of formula (I) wherein Y is N, $R^2$ is selected from the group consisting of alkyl, alkenyl, cycloalkyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Ay, —NHR$^{10}$Het, —R$^{10}$NR$^7$R$^8$ and —R$^{10}$NR$^7$Ay; and $R^3$ and $R^4$ are H, (all formulas and all other variables having been defined above in connection with Scheme 1) comprises the steps of:

(a) reacting a picoline of formula (XI) with a benzoylating agent of formula (II) to prepare a compound of formula (III);

(b) reacting the compound of formula (III) with a hydroxylamine source to prepare a compound of formula (IV);

(c) reacting the compound of formula (IV) with an acylating or sulfonylating agent to prepare a compound of formula (V);

(d) rearranging the compound of formula (V) to prepare a compound of formula (VI);

(e) acylating the compound of formula (VI) to prepare a compound of formula (VII);

(f) reacting the compound of formula (ill) with a dimethylformamide dialkyl acetal of formula (CH$_3$)$_2$NCH(ORa)$_2$ to prepare a compound of formula (VIII);

(g) reacting the compound of formula (VIII) with a compound of formula (X) to prepare a compound of formula (IX);

(h) halogenating the compound of formula (IX) to prepare a compound of formula (I-A); and (i) optionally either:
 (1) replacing the C-7 halogen (Hal) of the compound of formula (I-A) with an amine nucleophile selected from the group consisting —NR$^7$R$^8$,—NR$^7$Ay, —NHHet, —NHR$^{10}$Ay and —NHR$^{10}$Het; or
 (2) coupling the compound of formula (I-A) with a metal compound selected from the group consisting of Ay-M$^3$ and Het-M$^3$ to prepare a compound of formula (I-B).

More specifically, compounds of formula (I) wherein Y is N, $R^2$ is selected from the group consisting of alkyl, alkenyl, cycloalkyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$ NR$^7$R$^8$, —NR$^7$R$^8$, —NHHet, —NHR$^{10}$Ay, —NHR$^{10}$Het, —R$^{10}$NR$^7$R$^8$ and —R$^{10}$NR$^7$Ay; and $R^3$ and $R^4$ are H can be prepared halogenating the compound of formula (IX) to prepare a compound of formula (I-A):

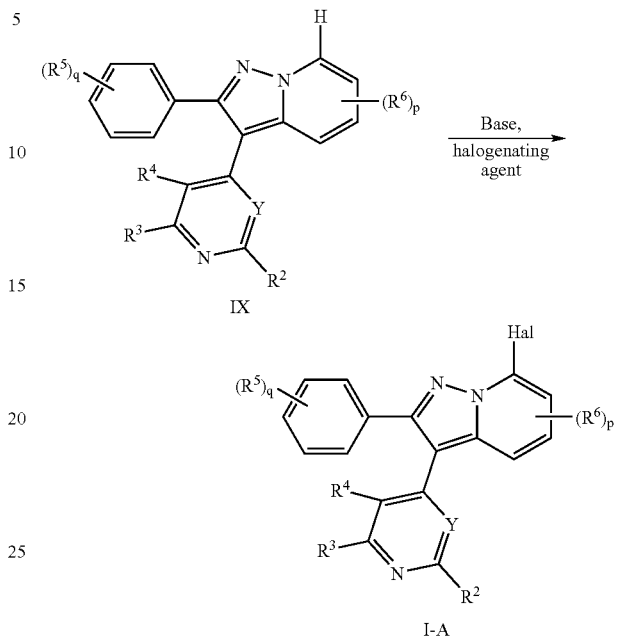

where all variables are as defined above in connection with Scheme 1.

A compound of the formula (IX) can be converted to a compound of formula (I-A) (i.e., a compound of formula (I) wherein $R^1$ is halo) by a halogenation protocol. Typically the halogenation is carried out by treatment of a compound of formula (IX) with a base in a suitable solvent, followed by treatment of the resulting anion with an appropriate halogen source. Suitable bases include but are not limited to n-butyllithium, and amide bases such as lithium diisopropylamide and the like. Inert solvents include tetrahydrofuran, diethyl ether and the like. Appropriate halogenating reagents include but are not limited to carbon tetrachloride, toluenesulfonyl chloride, N-bromosuccinimide, N-chlorosuccinimide, iodine (I$_2$) and the like.

Alternatively, the compounds of formula (I) may be prepared according to this and all following Schemes using an analogous procedure wherein the C-7 halogen is added on a preceding intermediate in the synthesis scheme or is present on the starting material. The methods for halogenating one of the preceding intermediates is the same as the method described above for halogenating the compounds of formula (IX). If the halogen is present on the starting material or added to one of the preceding intermediates the halogenation step depicted toward the end of the synthesis in the Scheme is unnecessary. In this embodiment, the halogen will already be present at the C-7 position and thus the compound of formula (I) will result directly from the reaction of the compound of formula (VIII) with the compound of formula (X). Such embodiments are contemplated by and included within the scope of the present invention.

The compound of formula (I-A) may optionally be converted to other compounds of formula (I), in particular compounds of formula (I-B) (i.e., compounds of formula (I) wherein $R^1$ is selected from the group consisting of Ay, Het, —NR$^7$R$^8$,—NR$^7$Ay, —NHHet, —NHR$^{10}$Ay and —NHR$^{10}$Het) by either of two methods.

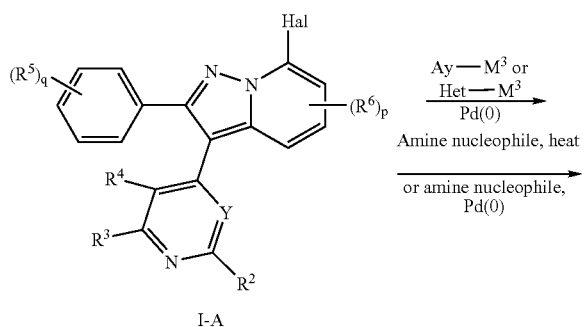

I-A

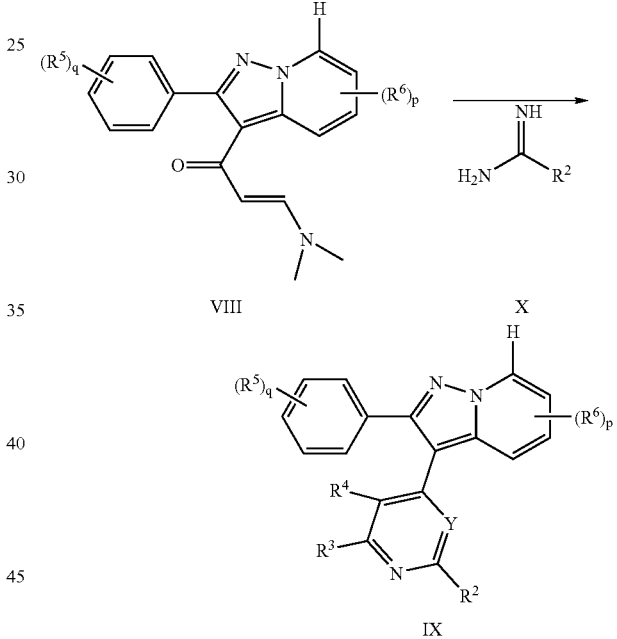

wherein all variables are as defined above in connection with Scheme 1.

According to the first method, compounds of formula (I-A) are converted to compounds of formula (I-B) by replacement of the C-7 halogen with an amine nucleophile. Typically the replacement is carried out by mixing the compound of formula (I-A) with an amine nucleophile selected from the group consisting of —$NR^7R^8$, —$NR^7Ay$, —NHHet, —$NHR^{10}Ay$ and —$NHR^{10}Het$; and optionally heating the reaction.

The reaction can also be carried out via an adaptation of procedures found in the literature (Wolfe, J. P.; Buchwald, S. L. J. Org. Chem. 2000, 65, 1144) wherein a compound of formula (I-A) is treated with an amine nucloephile, a palladium (0) or nickel (0) source and a base in a suitable solvent. Suitable sources of palladium (0) include but are not limited to palladium(II) acetate and tris(dibenzylideneacetone) dipalladium (0). Typical bases for use in the reaction include, for example sodium tert-butoxide and cesium carbonate. Toluene is an example of a suitable solvent.

According to the second method, compounds of formula (I-B) are prepared from compounds of formula (I-A) by coupling with metal compounds selected from the group consisting of Ay-$M^3$ and Het-$M^3$, wherein $M^3$ is —$B(OH)_2$, —$B(ORa)_2$, —$B(Ra)_2$, —$Sn(Ra)_3$, Zn-halide; Zn—Ra or Mg-halide, wherein Ra is alkyl or cycloalkyl and halide is halo. This method can be conveniently performed in an inert solvent, in the presence of a palladium (0) catalyst, optionally with heating. In one embodiment, the reaction is performed by reacting equimolar amounts of a compound of formula (I-A) with the metal compound selected from the group consisting of Ay-$M^3$ and Het-$M^3$ or optionally adding an excess of the metal compound. The palladium catalyst is typically present in 1–10 mol % compared to the compound of formula (I-A). Palladium catalysts that may be used may include, but are not limited to, tetrakistriphenylphosphine palladium (0) dichlorobis(triphenylphosphine)palladium (II), and bis(diphenylphosphinoferrocene)-palladium (II)

dichloride. Inert solvents for use in the reaction include but are not limited to, N,N-dimethylformamide, toluene, tetrahydrofuran, dioxane, and 1-methyl-2-pyrrolidinone.

When the metal compound of formula Ay-$M^3$ or Het-$M^3$ is an arylboronic acid or ester or an arylborinate, the reaction is more conveniently carried out by adding a base in a proportion equivalent to, or greater than, that of the metal compound.

Metal compounds of the formula Ay-$M^3$ and Het-$M^3$ can be purchased from commercial sources or prepared either as discreet isolated compounds or generated in situ by using methods known to one skilled in the art. (Suzuki, A. J. Organomet Chem. 1999, 576,147; Stille, J. Angew. Chem. Int Ed. Engl. 1986, 25, 508; Snieckus, V. J. Org. Chem. 1995, 60, 292.)

The compounds of formula (IX) from which the compounds of formula (I-A) are synthesized, may be prepared by reacting a compound of formula (VIII) with a compound of formula (X).

wherein all variables are as defined above in connection with Scheme 1.

This method can be readily carried out by mixing a compound of formula (VIII) with a compound of formula (X) in a suitable solvent, optionally in the presence of a base (typically when the amidine is in a salt form), and heating the reaction to 50–150° C. Typical solvents include lower alcohols such as methanol, ethanol, isopropanol, dimethylformamide and the like. The base is typically a sodium alkoxide, potassium carbonate, or an amine base such as triethylamine. In one embodiment, the solvent is dimethylformamide and the base is potassium carbonate, or an amine base such as triethylamine.

Compounds of the formula (VIII) may be conveniently prepared by reacting a compound of formula (VII) with a dimethylformamide dialkyl acetal of formula $(CH_3)_2NCH(ORa)_2$.

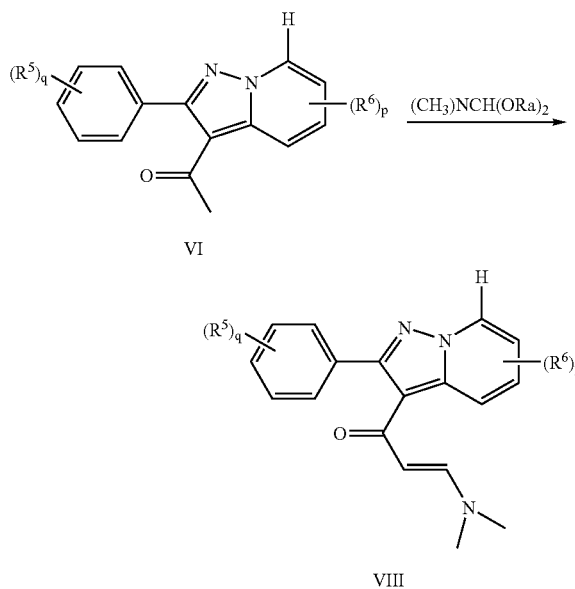

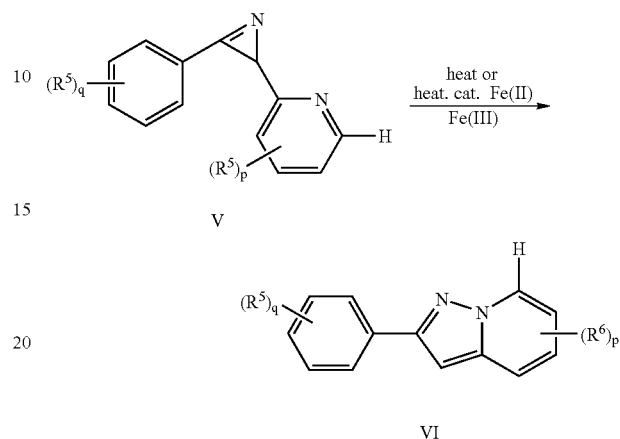

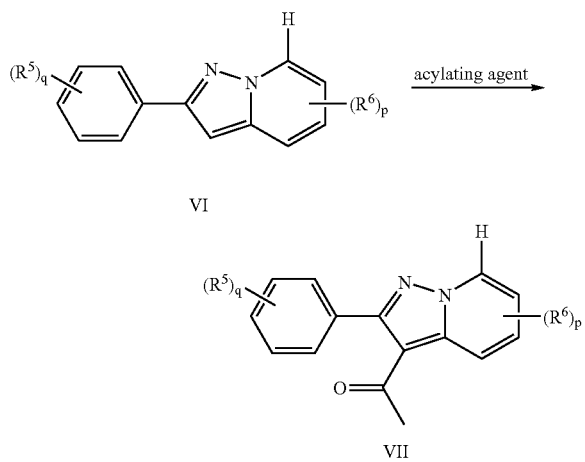

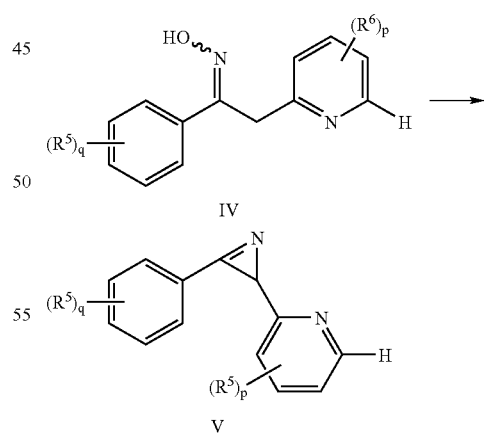

wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (VII) with the dimethylformamide dialkyl acetal, optionally with heating.

Compounds of formula (VII) may be prepared from compounds of the formula (VI) using an acylation procedure.

wherein all variables are as defined above in connection with Scheme 1.

Typically the acylation is carried out by treating the compounds of formula (VI) with an acylating agent, optionally in the presence of an acid or Lewis acid catalyst in an inert solvent with optional heating. Typical acylating agents will be readily determined by those skilled in the art. One acylating agent is acetic anhydride. Lewis acid catalysts are also known to those skilled in the art One Lewis acid catalyst for use in this reaction is boron trifluoride diethyl etherate. A suitable solvent is toluene.

Compounds of formula (VI) are conveniently prepared by rearranging an azirine compound of formula (V).

wherein all variables are as defined above in connection with Scheme 1.

The rearrangement of the azirines of formula (V) can be accomplished by heating a solution of the azirine of formula (V) in a suitable solvent at a temperature of about 160–200° C. Suitable inert solvents include, but are not limited to, 1-methyl-2-pyrrolidinone, and 1,2,4-trichlorobenzene. Another method for rearrangement of the azirine of formula (V) to compounds of formula (VI) involves reacting the compound of formula M with ferrous chloride ($FeCl_2$) or ferric chloride ($FeCl_3$). This reaction is typically done in an inert solvent with heating. A solvent for this reaction is 1,2-dimethoxyethane and the like.

Typically the azirines of formula (V) are prepared from oxime compounds of formula (IV) by treatment with acylating or sulfonylating agents in the presence of a base.

wherein all variables are as defined above in connection with Scheme 1.

Typical acylating or sulfonylating agents include but are not limited to, acetic anhydride, trifluoroacetic anhydride, methanesulfonyl chloride, toluenesulfonyl chloride and the like. Typical bases include, but are not limited to, triethylamine, diisopropylethylamine, pyridine, and the like. The reaction may be carried out in an inert solvent such as for example, chloroform, dichloromethane, toluene or the like.

The oxime compounds of formula (IV) are readily prepared by treating ketone compounds of formula (III) with a hydroxylamine source, in a suitable solvent, and optionally with a base.

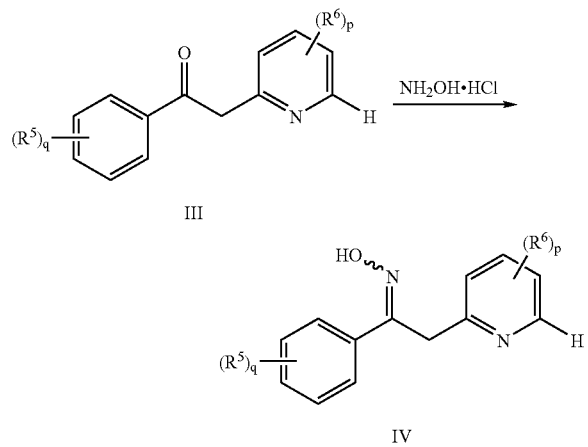

wherein all variables are as defined above in connection with Scheme 1.

Typically the hydroxylamine is hydroxylamine hydrochloride and the base is an aqueous solution of sodium hydroxide. Suitable solvents include lower alcohols such as methanol, ethanol, or isopropanol.

The ketone compounds of formula (III) can be prepared by treatment of a picoline of formula (XI) with a benzoylating agent of formula (II) in the presence of a base.

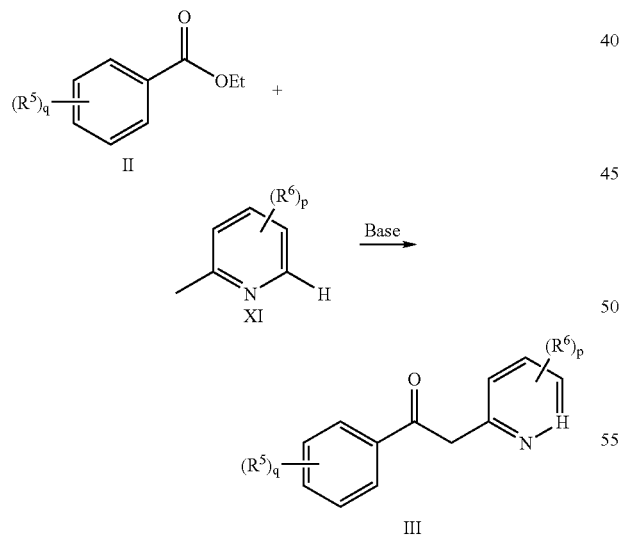

wherein all variables are as defined above in connection with Scheme 1.

Suitable benzoylating agents of formula (II) include, but are not limited to, benzoyl esters. An example of a suitable picoline is a chloropicoline. An example of a suitable base is lithium bis(trimethylsilyl)amide in an inert solvent such as tetrahydrofuran. Ketones such as those of formula (III) can be readily prepared using procedures known to one skilled in the art and/or described in the literature (Cassity, R. P.; Taylor, L. T.; Wolfe, J. F. *J.Org. Chem.* 1978, 2286).

In a further embodiment of the present invention, compounds of formula (I) wherein Y is N; $R^2$ is selected from the group consisting of alkyl, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n$Het, —$S(O)_nNR^7R^8$, —$NR^7R^8$, —NHHet, —$NHR^{10}$Ay, —$NHR^{10}$Het, —$R^{10}NR^7R^8$ and —$R^{10}NR^7$Ay; $R^3$ is selected from the group consisting of H, halo, alkyl, alkenyl, cycloalkyl, Het, —$C(O)R^7$, $C(O)$Ay, —$CO_2R^7$, —$CO_2$Ay, —$SO_2NHR^9$, —$NR^7R^8$ where neither $R^7$ nor $R^8$ is H, —$NR^7$Ay where $R^7$ is not H, —$R^{10}OR^7$, —$R^{10}O$Ay, —$R^{10}NR^7R^8$ and —$R^{10}NR^7$Ay;

and $R^4$ is H, may be conveniently prepared by a general process outlined in Scheme 2 below.

Scheme 2

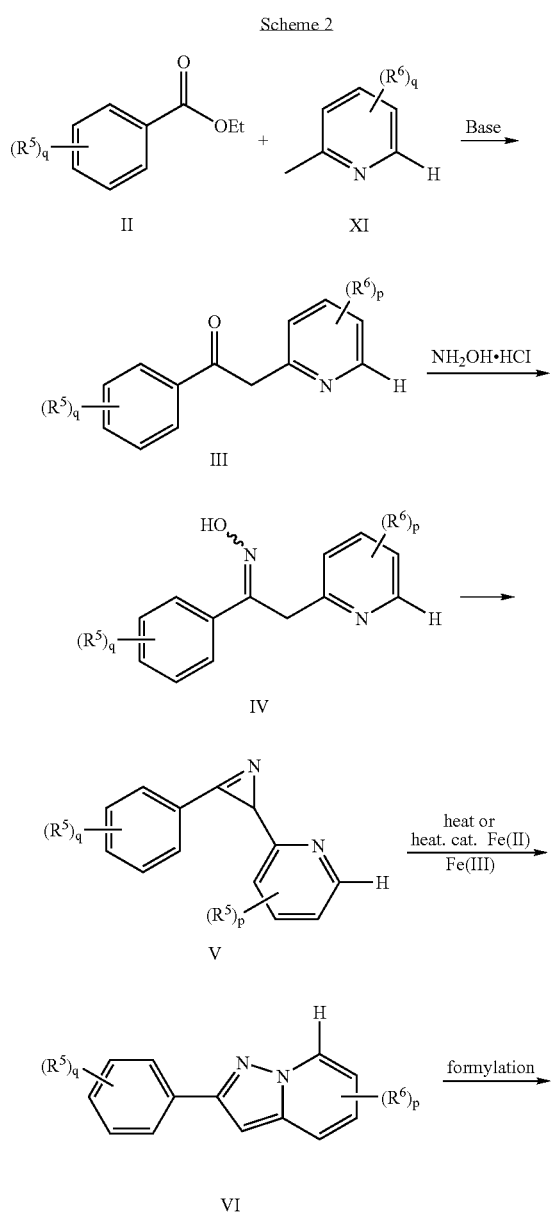

-continued

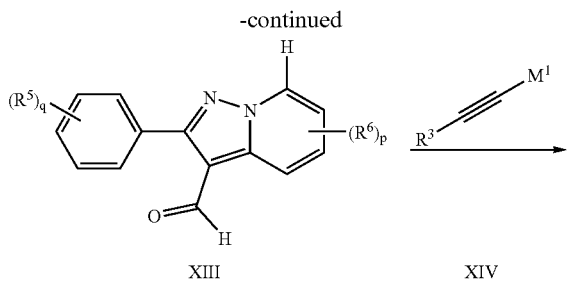

XIII    XIV

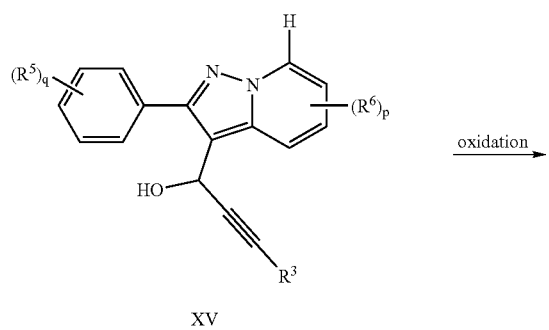

XV

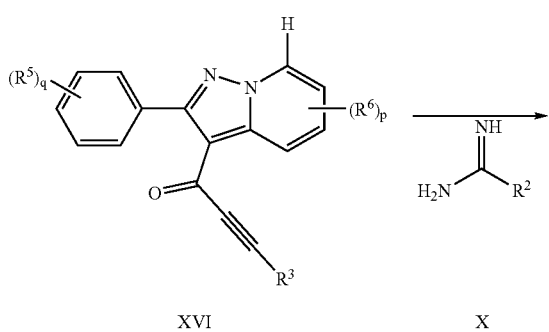

XVI    X

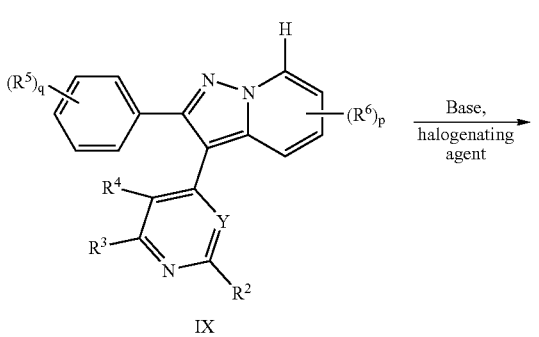

IX

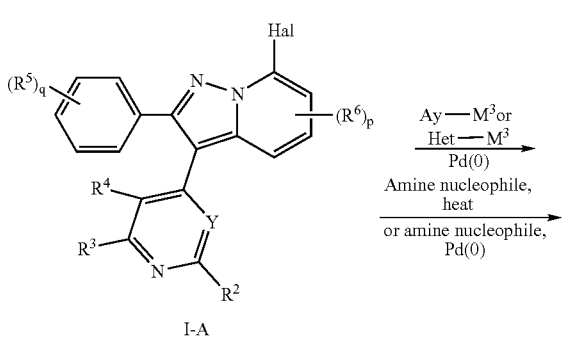

I-A

-continued

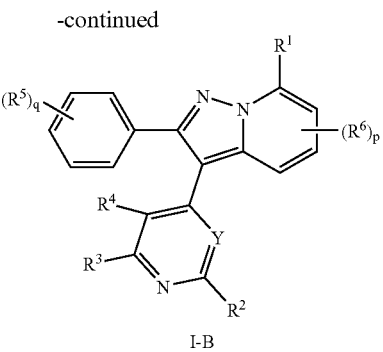

I-B wherein:

R¹ is selected from the group consisting of halo, Ay, Het, —NR⁷R⁸, —NR⁷Ay, —NHHet, —NHR¹⁰Ay and —NHR¹⁰NHet;

each R⁷ and R⁸ are the same or different and are independently selected from the group consisting of H, alkyl, alkenyl, cycloalkyl, cycloalkenyl, —OR⁹, —C(O)R⁹, —CO₂R⁹, —C(O)NR⁹R¹¹, —C(S)NR⁹R¹¹, —C(NH)NR⁹R¹¹, —SO₂R¹⁰, —SO₂NR⁹R¹¹, —R¹⁰cycloalkyl, —R¹⁰OR⁹, —CH(R¹⁰OR⁹)₂, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R¹⁰, —R¹⁰SO₂NR⁹R¹¹, —R¹⁰SO₂NHCOR⁹, —R¹⁰NR⁹R¹¹, —R¹⁰NHCOR⁹, —R¹⁰NHSO₂R⁹ and —R¹⁰NHC(NH)NR⁹R¹¹ and;

each R⁹ and R¹¹ are the same or different and are independently selected from the group consisting of H, alkyl, cycloalkyl, —R¹⁰cycloalkyl, —R¹⁰OH, —R¹⁰(OR¹⁰)ᵥᵥ where w is 1–10, and —R¹⁰NR¹⁰R¹⁰;

each R¹⁰ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

n is 0, 1 or 2;

R² is selected from the group consisting of alkyl, alkenyl, cycloalkyl, cycloalkenyl, Ay, Het, —OR⁷, —OAy, —OHet, —OR¹⁰Het, —S(O)ₙR⁹, —S(O)ₙAy, —S(O)ₙHet, —S(O)ₙNR⁷R⁸, —NR⁷R⁸, —NHHet, —NHR¹⁰Ay, —NHR¹⁰Het, —R¹⁰NR⁷R⁸ and —R¹⁰NR⁷Ay;

Y is N;

R³ is selected from the group consisting of H, halo, alkyl, alkenyl, cycloalkyl, Het, —C(O)R⁷, C(O)Ay, —CO₂R⁷, —CO₂Ay, —SO₂NHR⁹, —NR⁷R⁸ where neither R⁷ nor R⁸ is H, —NR⁷Ay where R⁷ is not H, —R¹⁰OR⁷, —R¹⁰OAy, —R¹⁰NR⁷R⁸ and —R¹⁰NR⁷Ay;

R⁴ is H;

q is 0, 1, 2, 3, 4 or 5;

each R⁵ is the same or different and is independently selected from the group consisting of halo, alkyl, alkenyl, alkynyl, cycloalkyl, cycloalkenyl, Ay, Het, —OR⁷, —OAy, —OHet, —C(O)R⁹, —C(O)Ay, —C(O)Het, —CO₂R⁹, —C(O)NR⁷R⁸, —C(O)NR⁷Ay, —C(O)NHR¹⁰Het, —C(S)NR⁹R¹¹, —C(NH)NR⁷R⁸, —C(NH)NR⁷Ay, —S(O)ₙR⁹, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰OR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R⁵ groups together with the atoms to which they are bonded form a C₅₋₆ cycloalkyl or aryl;

p is 1, 2 or 3; and each R⁶ is the same or different and is independently selected from the group consisting of halo, alkyl, alkenyl, alkynyl, cycloalkyl, cycloalkenyl, Ay, Het, —OR⁷, —OAy, —OHet, —OR¹⁰Ay, —OR¹⁰Het, —C(O)R⁹, —C(O)Ay, —C(O)Het, —CO₂R⁹, —C(O)NR⁷R⁸, —C(O)NR⁷Ay, —C(O)NHR¹⁰Ay, —C(O)NHR¹⁰Het, —C(S)NR⁹R¹¹, —C(NH)NR⁷R⁸, —C(NH)NR⁷Ay, —S(O)ₙR⁹, —S(O)ₙAy, —S(O)ₙHet, —S(O)₂NR⁷R⁸, —S(O)₂NR⁷Ay, —NR⁷R⁸, —NR⁷Ay, —NHHet, —NHR¹⁰Ay, —NHR¹⁰Het, —R¹⁰cycloalkyl, —R¹⁰Ay, —R¹⁰Het, —R¹⁰OR⁹, —R¹⁰—O—C(O)R⁹, —R¹⁰—O—C(O)Ay, —R¹⁰—O—C(O)Het, —R¹⁰—O—S(O)ₙR⁹, —R¹⁰C(O)R⁹, —R¹⁰CO₂R⁹, —R¹⁰C(O)NR⁹R¹¹, —R¹⁰C(S)NR⁹R¹¹, —R¹⁰C(NH)NR⁹R¹¹, —R¹⁰SO₂R⁹, —R¹⁰SO₂NR⁹R¹¹, —R¹⁰SO₂NHCOR⁹, —R¹⁰NR⁷R⁸, —R¹⁰NR⁷Ay, —R¹⁰NHC(NH)NR⁹R¹¹, cyano, nitro and azido; or two adjacent R⁶ groups together with the atoms to which they are bonded form a C₅₋₆ cycloalkyl or a 5- or 6-membered heterocyclic group containing 1 or 2 heteroatoms; or R⁶ is in the 6 position and R⁵ and R¹ together with the atoms to which they are bonded form a C₅₋₆ cycloalkyl or a 5- or 6-membered heterocyclic group containing 1 or 2 heteroatoms;

M¹ is Li, Mg-halide or cerium-halide, wherein halide is halo;

Hal is halo; and

M³ is —B(OH)₂, —B(ORa)₂, —B(Ra)₂, —Sn(Ra)₃, Zn-halide, Zn—Ra or Mg-halide where halide is halo.

Generally, the process for preparing compounds of formula (I) wherein Y is N; R² is selected from the group consisting of alkyl, alkenyl, cycloalkyl, cycloalkenyl, Ay, Het, —OR⁷, —OAy, —OHet, —OR¹⁰Het, —S(O)ₙR⁹, —S(O)ₙAy, —S(O)ₙHet, —S(O)ₙNR⁷R⁸, —NR⁷R⁸, —NHHet, —NHR¹⁰Ay, —NHR¹⁰Het, —R¹⁰NR⁷R⁸ and —R¹⁰NR⁷Ay; R³ is selected from the group consisting of H, halo, alkyl, alkenyl, cycloalkyl, Het, —C(O)R⁷, C(O)Ay, —CO₂R⁷, —CO₂Ay, —SO₂NHR⁹, —NR⁷R⁸ where neither R⁷ nor R⁸ is H, —NR⁷Ay where R⁷ is not H, —R¹⁰OR⁷, —R¹⁰OAy, —R¹⁰NR⁷R⁸ and —R¹⁰NR⁷Ay; and R⁴ is H (all other variables having been defined above in connection with Scheme 2), comprises the following steps:

(a) reacting a picoline of formula (XI) with a benzoylating agent of formula (II) to prepare a compound of formula (III);

(b) reacting the compound of formula (III) with a hydroxylamine source to prepare a compound of formula (IV);

(c) reacting the compound of formula (IV) with an acylating or sulfonylating agent to prepare a compound of formula (V);

(d) rearranging the compound of formula (V) to prepare a compound of formula (VI);

(e) formylating the compound of formula (VI) to prepare a compound of formula (XIII);

(f) reacting the compound of formula (XIII) with a compound of formula (XIV) to prepare a compound of formula (XV);

(g) oxidizing the compound of formula (XV) to prepare a compound of formula (XVI);

(h) reacting the compound of formula (XVI) with a compound of formula (X) to prepare a compound of formula (IX);

(i) halogenating the compound of formula (IX) to prepare a compound of formula (I-A); and (j) optionally either:

(1) replacing the C-7 halogen (Hal) of the compound of formula (I-A) with an amine nucleophile selected from the group consisting —NR⁷R⁸,—NR⁷Ay, —NHHet, —NHR¹⁰Ay and —NHR¹⁰Het; or (2) coupling the compound of formula (I-A) with a metal compound selected from the group consisting of Ay-M³ and Het-M³ to prepare a compound of formula (I-B).

More specifically, compounds of formula (I) wherein Y is N; R² is selected from the group consisting of alkyl, alkenyl, cycloalkyl, cycloalkenyl, Ay, Het, —OR⁷, —OAy, —OHet, —OR¹⁰Het, —S(O)ₙR⁹, —S(O)ₙAy, —S(O)ₙHet, —S(O)ₙNR⁷R⁸, —NR⁷R⁸, —NHHet, —NHR¹⁰Ay, —NHR¹⁰Het, —R¹⁰NR⁷R⁸ and —R¹⁰NR⁷Ay; R³ is selected from the group consisting of H, halo, alkyl, alkenyl, cycloalkyl, Het, —C(O)R⁷, C(O)Ay, —CO₂R⁷, —CO₂Ay, —SO₂NHR⁹, —NR⁷R⁸ where neither R⁷ nor R⁸ is H, —NR⁷Ay where R⁷ is not H, —R¹⁰OR⁷, —R¹⁰OAy, —R¹⁰NR⁷R⁸ and —R¹⁰NR⁷Ay; and R⁴ is H, may be prepared by halogenating the compound of formula (IX) to prepare a compound of formula (I-A). Suitable methods for halogenating the compound of formula (IX) and for converting compounds of formula (I-A) to compounds of formula (I-B) are described above in connection with Scheme 1.

The compounds of formula (IX) may be prepared by reacting the compound of formula (XVI) with a compound of formula (X).

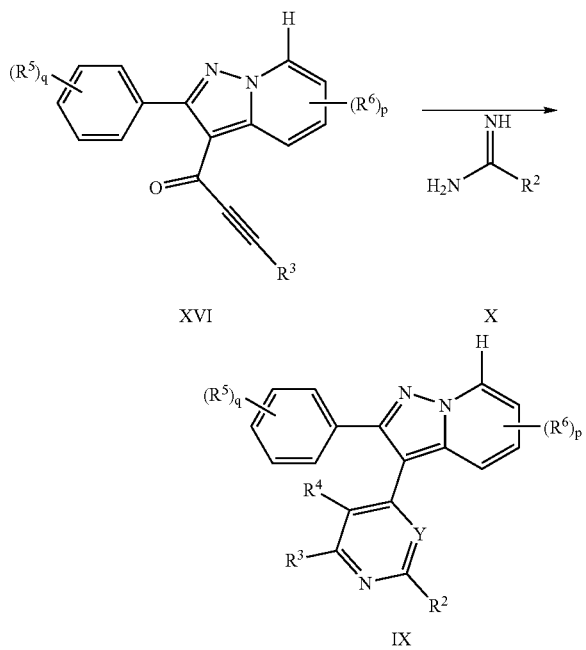

wherein all variables are as defined above in connection with Scheme 2.

This method can be readily carried out by mixing a compound of formula (XVI) with a compound of formula (X) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide and the base is potassium carbonate, or an amine base such as triethylamine.

Compounds of formula (XVI) may be conveniently prepared by oxidation of a compound of formula (XV).

XV → oxidation → XVI wherein all variables are as defined above in connection with Scheme 2. Suitable oxidizing agents include but are not limited to, manganese dioxide, and the like, in an inert solvent. Suitable inert solvents include but are not limited to, dichloromethane, chloroform, N,N-dimethylformamide, ether, and the like.

Compounds of formula (XV) may be conveniently prepared by reacting a compound of formula (XIII) with a compound of formula (XIV).

XIII + XIV → XV wherein all variables are as defined above in connection with Scheme 2.

Particular metals ($M^1$) in the compounds of formula (XIV) include but are not limited to, lithium, magnesium(II) halides, cerium(III) halides, and the like. Compounds of formula (XIV) may be purchased from commercial sources or prepared by methods known to one skilled in the art.

Compounds of formula (XIII) may be conveniently prepared from compounds of formula (VI) by a formylation procedure.

VI → formylation → XIII wherein all variables are as defined above in connection with Scheme 2.

Typically the formylation is carried out via the Vilsmeier-Haack reaction. The Vilsmeier-Haack reagents can be purchased from commercial sources or prepared in situ. Particular conditions include, but are not limited to treating compounds of formula (VI) with a premixed solution of phosphorous oxychloride in N,N-dimethylformamide optionally with heating the reaction to 50–150° C.

The compounds of formula (VI) are prepared by the process described above in connection with Scheme 1.

In addition to the foregoing process for preparing certain compounds of formula (I), the present invention also provides certain intermediate compounds for use in the preparation of such compounds of formula (I) according to the foregoing process. Such intermediates are described in Schemes 1 and 2 above.

Further, compounds of formula (I) wherein Y is N and $R^2$ is selected from the group consisting of alkyl, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n$Het, —$S(O)_n$$NR^7R^8$, —$NR^7R^8$, —NHHet, —$NHR^{10}$Ay, —$NHR^{10}$Het, —$R^{10}NR^7R^8$ and —$R^{10}NR^7$Ay, may be conveniently prepared by the process outlined in Scheme 3 below.

Scheme 3

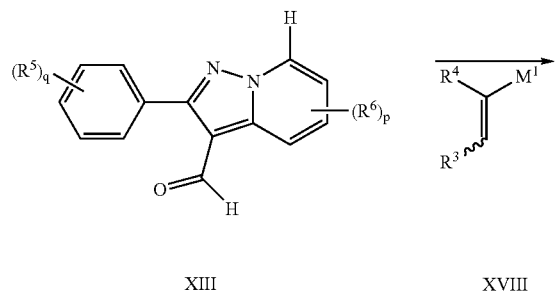

XIII      XVIII

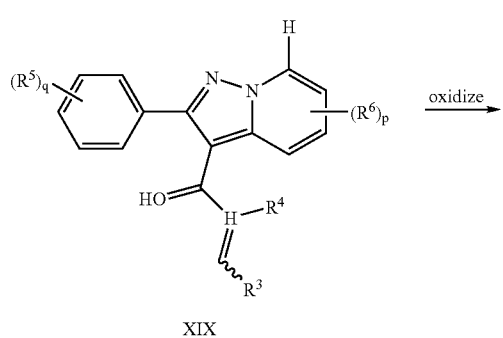

XIX

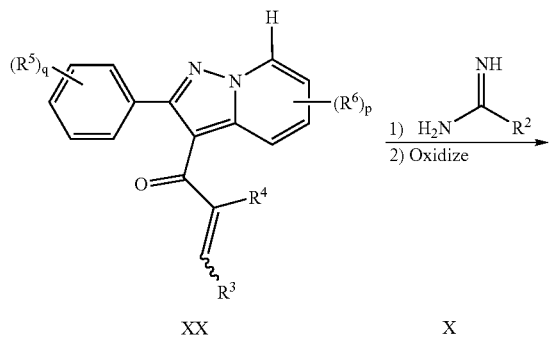

XX      X

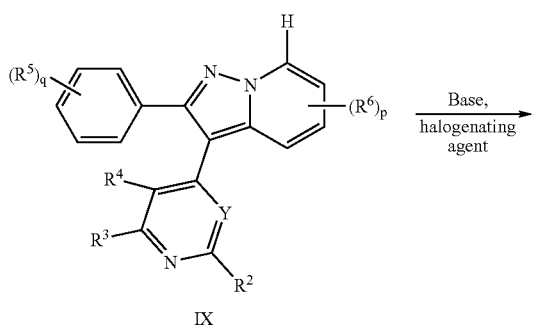

IX

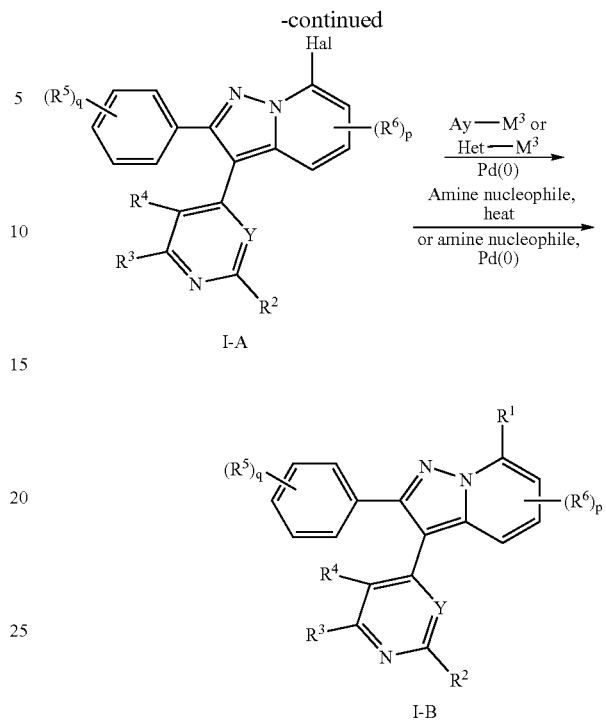

I-A

I-B wherein:

$R^1$ is selected from the group consisting of halo, Ay, Het, —$NR^7R^8$, —$NR^7$Ay, —NHHet, —$NHR^{10}$Ay and —$NHR^{10}$Het;

each $R^7$ and $R^8$ are the same or different and are independently selected from the group consisting of H, alkyl, alkenyl, cycloalkyl, cycloalkenyl, —$OR^9$, —$C(O)R^9$, —$CO_2R^9$, —$C(O)NR^9R^{11}$, —$C(S)NR^9R^{11}$, —$C(NH)NR^9R^{11}$, —$SO_2R^{10}$, —$SO_2NR^9R^{11}$, —$R^{10}$cycloalkyl, —$R^{10}OR^9$, —$CH(R^{10}OR^9)_2$, —$R^{10}C(O)R^9$, —$R^{10}C(O)NR^9R^{11}$, —$R^{10}C(S)NR^9R^{11}$, —$R^{10}C(NH)NR^9R^{11}$, —$R^{10}S_2R^{10}$, —$R^{10}SO_2NR^9R^{11}$, —$R^{10}SO_2NHCOR^9$, —$R^{10}NR^9R^{11}$, —$R^{10}NHCOR^9$, —$R^{10}NHSO_2R^9$ and —$R^{10}NHC(NH)NR^9R^{11}$ and;

each $R^9$ and $R^{11}$ are the same or different and are independently selected from the group consisting of H, alkyl, cycloalkyl, —$R^{10}$cycloalkyl, —$R^{10}$OH, —$R_{10}(OR^{10})_w$ where w is 1–10, and —$R^{10}NR^{10}R^{10}$;

each $R^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

n is 0, 1 or 2;

$R^2$ is selected from the group consisting of alkyl, alkenyl, cycloalkyl, cycloalkenyl, Ay, Het, —$OR^7$, —OAy, —OHet, —$OR^{10}$Het, —$S(O)_nR^9$, —$S(O)_n$Ay, —$S(O)_n$Het, —$S(O)_nNR^7R^8$, —$NR^7R^8$, —NHHet, —$NHR^{10}$Ay, —$NHR^{10}$Het, —$R^{10}NR^7R^8$ and —$R^{10}NR^7$Ay;

Y is N;

$R^3$ and $R^4$ are the same or different and are each independently selected from the group consisting of H, halo, alkyl, alkenyl, cycloalkyl, Ay, Het, —OR$^7$, —OAy, —C(O)R$^7$, C(O)Ay, —CO$_2$R$^7$, —CO$_2$Ay, —SO$_2$NHR$^9$, —NR$^7$R$^8$, —NR$^7$Ay, —NHHet, —NHR$^{10}$Het —R$^{10}$OR$^7$, —R$^{10}$OAy, —R$^{10}$NR$^7$R$^8$ and —R$^{10}$NR$^7$Ay;

q is 0, 1, 2, 3, 4 or 5;

each R$^5$ is the same or different and is independently selected from the group consisting of halo, alkyl, alkenyl, alkynyl, cycloalkyl, cycloalkenyl, Ay, Het, —OR$^7$, —OAy, —OHet, —C(O)R$^9$, —C(O)Ay, —C(O)Het, —CO$_2$R$^9$, —C(O)NR$^7$R$^8$, —C(O)NR$^7$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent R$^5$ groups together with the atoms to which they are bonded form a $C_{5-6}$ cycloalkyl or aryl;

p is 1, 2 or 3;

each R$^6$ is the same or different and is independently selected from the group consisting of halo, alkyl, alkenyl, alkynyl, cycloalkyl, cycloalkenyl, Ay, Het, —OR$^7$, —OAy, —OHet, —OR$^{10}$Ay, —OR$^{10}$Het, —C(O)R$^9$, —C(O)Ay, —C(O)Het, —CO$_2$R$^9$, —C(O)NR$^7$R$^8$, —C(O)NR$^7$Ay, —C(O)NHR$^{10}$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$C(O)R$^9$, —R$^{10}$CO$_2$R$^9$, —R$^{10}$C(O)NR$^9$R$^{11}$, —R$^{11}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent R$^6$ groups together with the atoms to which they are bonded form a $C_{5-6}$ cycloalkyl or a 5- or 6-membered heterocyclic group containing 1 or 2 heteroatoms; or R$^6$ is in the 6 position and R$^6$ and R$^1$ together with the atoms to which they are bonded form a $C_{5-6}$ cycloalkyl or a 5- or 6-membered heterocyclic group containing 1 or 2 heteroatoms;

M$^1$ is Li, Mg-halide or cerium-halide, wherein halide is halo;

Hal is halo; and

M$^3$ is —B(OH)$_2$, —B(ORa)$_2$, —B(Ra)$_2$, —Sn(Ra)$_3$, Zn-halide, Zn—Ra or Mg-halide where halide is halo.

Generally, the process for preparing compounds of formula (I) wherein Y is N and R$^2$ is selected from the group consisting of alkyl, alkenyl, cycloalkyl, cycloalkenyl, Ay, Het, —OR$^7$, —OAy, —OHet, —OR$^{10}$Het, —S(O)$_n$R$^9$, —S(O)Ay, —S(O)$_n$Het, —S(O)$_n$NR$^7$R$^8$, —NR$^7$R$^8$, —NHHet, —NHR$^{10}$Ay, —NHR$^{10}$Het, —R$^{10}$NR$^7$R$^8$ and —R$^{10}$NR$^7$Ay, (all formulas and all other variables having been defined above in connection with Scheme 3), comprises the following steps:

(a) reacting a picoline of formula (XI) with a benzoylating agent of formula (II) to prepare a compound of formula (III);

(b) reacting the compound of formula (III) with a hydroxylamine source to prepare a compound of formula (IV);

(c) reacting the compound of formula (IV) with an acylating or sulfonylating agent to prepare a compound of formula (V);

(d) rearranging the compound of formula (V) to prepare a compound of formula (VI);

(e) formylating the compound of formula (VI) to prepare a compound of formula (XIII);

(f) reacting the compound of formula (XIII) with a compound of formula (XVIII) to prepare a compound of formula (XIX);

(g) oxidizing the compound of formula (XIX) to prepare a compound of formula (XX);

(h) reacting the compound of formula (XX) with a compound of formula (X) followed by oxidative aromatization to prepare a compound of formula (IX);

(i) halogenating the compound of formula (IX) to prepare a compound of formula (I-A); and (j) optionally either:

(1) replacing the C-7 halogen (Hal) of the compound of formula (I-A) with an amine nucleophile selected from the group consisting of —NR$^7$R$^8$,—NR$^7$Ay, —NHHet, —NHR$^{10}$Ay and —NHR$^{10}$Het; or (2) coupling the compound of formula (I-A) with a metal compound selected from the group consisting of Ay-M$^3$ and Het-M$^3$ to prepare a compound of formula (I-B).

More specifically, compounds of formula (I) wherein Y is N and R$^2$ is selected from the group consisting of alkyl, alkenyl, cycloalkyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Ay, —NHR$^{10}$Het, —R$^{10}$NR$^7$R$^8$ and —R$^{10}$NR$^7$Ay, can be prepared by halogenating the compound of formula (IX) to prepare a compound of formula (I-A). Suitable methods for halogenating the compound of formula (IX) and for converting compounds of formula (I-A) to compounds of formula (I-B) are described above in connection with Scheme 1.

The compounds of formula (IX) may be prepared by reacting the compound of formula (XX) with a compound of formula (X) followed by oxidative aromatization.

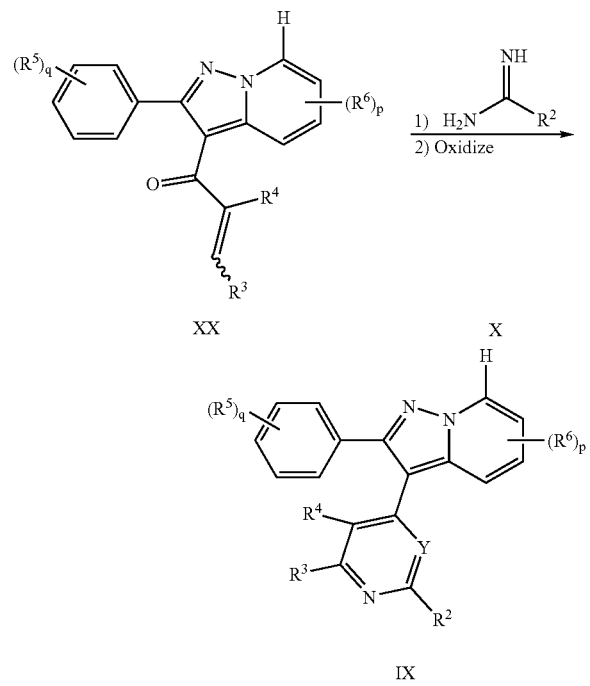

wherein all variables are as defined above in connection with Scheme 3.

The condensation is conveniently carried out by treating a compound of formula (XX) with a compound of formula (X) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or an amine base such as triethylamine. The reaction produces a dihydropyrimidine intermediate.

Suitably in the same reaction vessel, the dihydropyrimidine intermediate may be oxidized to a compound of formula (IX) by the addition of an oxidizing agent. The reaction may be heated to 50–150° C. or performed at ambient temperature. Suitable oxidizing agents are oxygen (O$_2$), palladium on carbon, 2,3-dichloro-5,6-dicyano-1,4-benzoquinone, or the like.

Compounds of formula (XX) may be conveniently prepared by oxidation of compounds of formula (XIX).

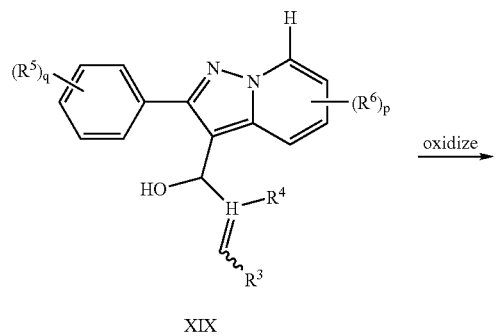

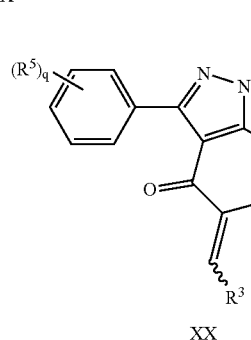

wherein all variables are as defined above in connection with Scheme 3.

Particular oxidizing agents for the oxidation of compounds of formula (XIX) include but are not limited to manganese dioxide, and the like. The oxidation is typically carried out in an inert solvent such as for example, dichloromethane, chloroform, N,N-dimethylformamide, ether, and the like.

Compounds of formula (XIX) may be conveniently prepared by reacting a compound of formula (XIII) with a compound of formula (XVIII).

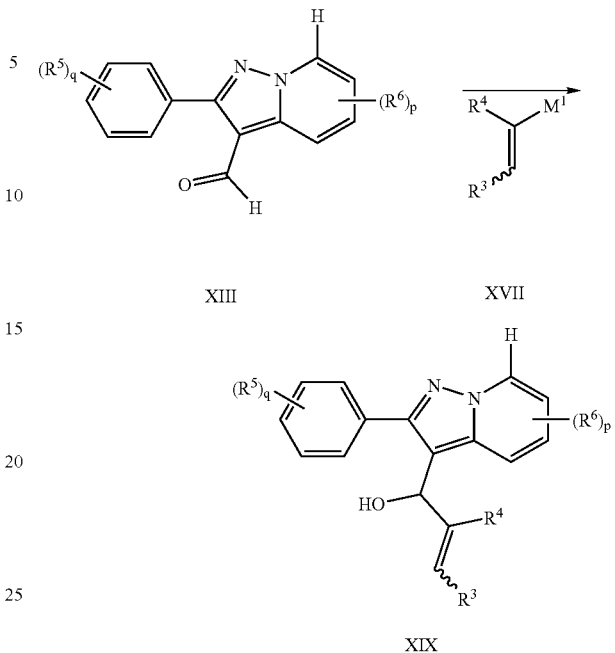

wherein all variables are as defined above in connection with Scheme 3.

Compounds of formula (XVIII) may be purchased from commercial sources or prepared by methods known to one skilled in the art. The compounds of formula (XIII) may be prepared using the methods described above in connection with Scheme 2.

In addition to the foregoing process for preparing certain compounds of formula (I), the present invention also provides certain intermediate compounds for use in the preparation of such compounds of formula (I) according to the foregoing process. Such intermediates are described above in Scheme 3.

Compounds of formula (I) wherein Y is CH or N, may be conveniently prepared by the process outlined in Scheme 4 below.

Scheme 4

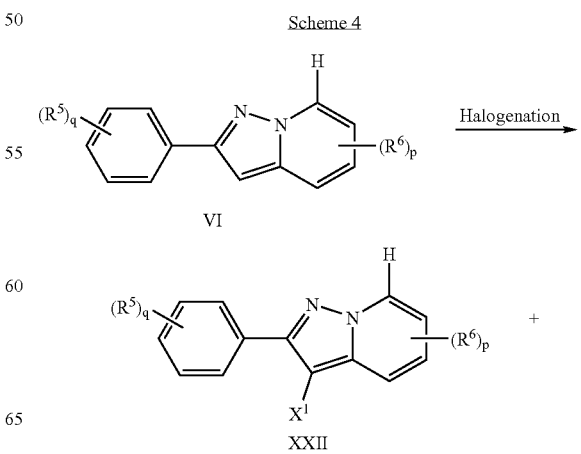

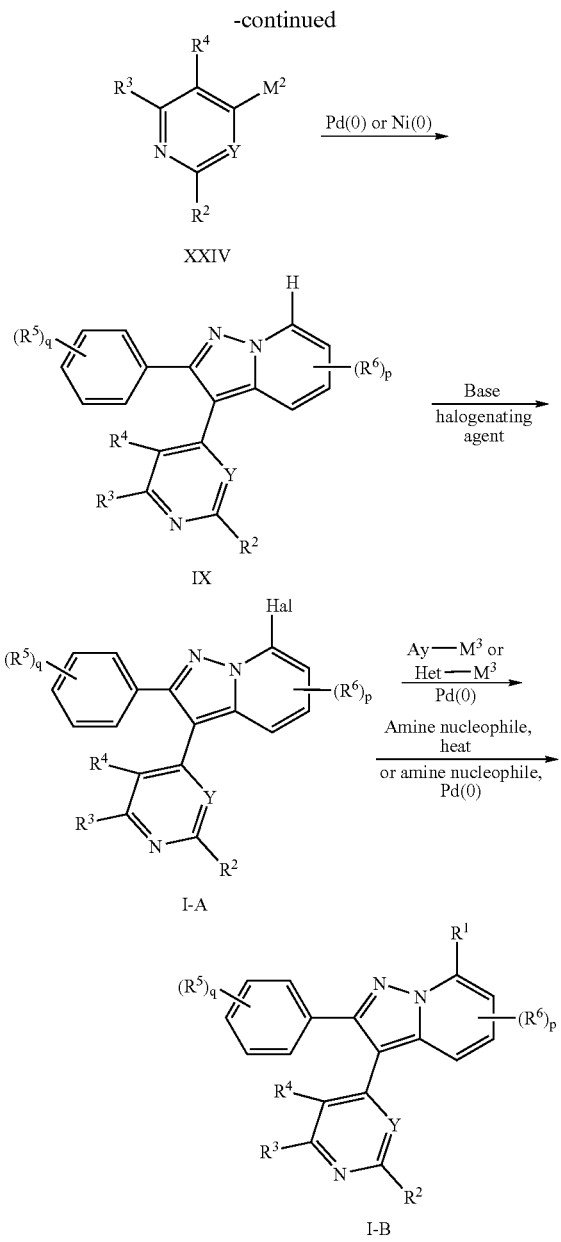

alkyl, cycloalkyl, —R$^{10}$cycloalkyl, —R$^{10}$OH, —R$_{10}$(OR$^{10}$)$_w$ where w is 1–10, and —R$^{10}$NR$^{10}$R$^{10}$;

each R$^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

n is 0, 1 or 2;

R$^2$ is selected from the group consisting of halo, alkyl, alkenyl, cycloalkyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Ay, —NHR$^{10}$Het, —R$^{10}$NR$^7$R$^8$ and —R$^{10}$NR$^7$Ay;

Y is N or CH;

R$^3$ and R$^4$ are the same or different and are each independently selected from the group consisting of H, halo, alkyl, alkenyl, cycloalkyl, Ay, Het, —OR$^7$, —OAy, —C(O)R$^7$, C(O)Ay, —CO$_2$R$^7$, —CO$_2$Ay, —SO$_2$NHR$^9$, —NR$^7$R$^8$, —NR$^7$Ay, —NHHet, —NHR$^{10}$Het —R$^{10}$OR$^7$, —R$^{10}$OAy, —R$^{10}$NR$^7$R$^8$ and —R$^{10}$NR$^7$Ay;

q is 0, 1, 2, 3, 4 or 5;

each R$^5$ is the same or different and is independently selected from the group consisting of halo, alkyl, alkenyl, alkynyl, cycloalkyl, cycloalkenyl, Ay, Het, —OR$^7$, —OAy, —OHet, —C(O)R$^9$, —C(O)Ay, —C(O)Het, —CO$_2$R$^9$, —C(O)NR$^7$R$^8$, —C(O)NR$^7$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent R$^5$ groups together with the atoms to which they are bonded form a C$_{5-6}$ cycloalkyl or aryl;

p is 1, 2 or 3;

each R$^6$ is the same or different and is independently selected from the group consisting of halo, alkyl, alkenyl, alkynyl, cycloalkyl, cycloalkenyl, Ay, Het, —OR$^7$, —OAy, —OHet, —OR$^{10}$Ay, —OR$^{10}$Het, —C(O)R$^9$, —C(O)Ay, —C(O)Het, —CO$_2$R$^9$, —C(O)NR$^7$R$^8$, —C(O)NR$^7$Ay, —C(O)NHR$^{10}$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent R$^6$ groups together with the atoms to which they are bonded form a C$_{5-6}$ cycloalkyl or a 5- or 6-membered heterocyclic group containing 1 or 2 heteroatoms; or R$^6$ is in the 6 position and R$^6$ and R$^1$ together with the atoms to which they are bonded form a C$_{5-6}$ cycloalkyl or a 5- or 6-membered heterocyclic group containing 1 or 2 heteroatoms;

X$^1$ is selected from the group consisting of chloro, bromo and iodo;

wherein:

R$^1$ is selected from the group consisting of halo, Ay, Het, —NR$^7$R$^8$, —NR$^7$Ay, —NHHet, —NHR$^{10}$Ay and —NHR$^{10}$Het;

each R$^7$ and R$^8$ are the same or different and are independently selected from the group consisting of H, alkyl, alkenyl, cycloalkyl, cycloalkenyl, —OR$^9$, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, SO$_2$NR$^9$R$^{11}$, —R$^{10}$cycloalkyl, —R$^{10}$OR$^9$, —CH(R$^{10}$OR$^9$)$_2$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^{10}$, —R$^{10}$SO$_2$NR$^9$R$^{11}$, —R$^{10}$SO$_2$NHCOR$^9$, —R$^{10}$NR$^9$R$^{11}$, —R$^{10}$NHCOR$^9$, —R$^{10}$NHSO$_2$R$^9$ and —R$^{10}$NHC(NH)NR$^9$R$^{11}$ and;

each R$^9$ and R$^{11}$ are the same or different and are independently selected from the group consisting of H, $M^2$ is —B(OH)$_2$, —B(ORa)$_2$, —B(Ra)$_2$, —Sn(Ra)$_3$, Zn-halide, ZnRa, or Mg-halide where Ra is alkyl or cycloalkyl and halide is halo;

Hal is halo; and $M^3$ is —B(OH)$_2$, —B(ORa)$_2$, —B(Ra)$_2$, —Sn(Ra)$_3$, Zn-halide, Zn—Ra or Mg-halide where halide is halo.

Generally, the process for preparing compounds of formula (I) (all formulas and variables having been defined above in connection with Scheme 4), comprises the following steps:

a) reacting a picoline of formula (XI) with a benzoylating agent of formula (II) to prepare a compound of formula (III);

b) reacting the compound of formula (III) with a hydroxylamine source to prepare a compound of formula (IV);

c) reacting the compound of formula (IV) with an acylating or sulfonylating agent to prepare a compound of formula (V);

d) rearranging the compound of formula (M) to prepare a compound of formula (VI);

e) halogenating a compound of formula (VI) to prepare a compound of formula (XXII);

f) reacting the compound of formula (XXII) with a compound of formula (XXIV) to prepare a compound of formula (IX);

(g) halogenating the compound of formula (IX) to prepare a compound of formula (I-A); and (h) optionally either:

(1) replacing the C-7 halogen (Hal) of the compound of formula (I-A) with an amine nucleophile selected from the group consisting —NR$^7$R$^8$, —NR$^7$Ay, —NHHet, —NHR$^{10}$Ay and —NHR$^{10}$Het; or (2) coupling the compound of formula (I-A) with a metal compound selected from the group consisting of Ay-M$^3$ and Het-M$^3$ to prepare a compound of formula (I-B).

More specifically, compounds of formula (I) wherein Y is N or CH can be prepared by by halogenating the compound of formula (IX) to prepare a compound of formula (I-A). Suitable methods for halogenating the compound of formula (IX) and for converting compounds of formula (I-A) to compounds of formula (I-B) are described above in connection with Scheme 1.

The compounds of formula (IX) may be prepared by reacting a compound of formula (XXII) with a compound of formula (XXIV).

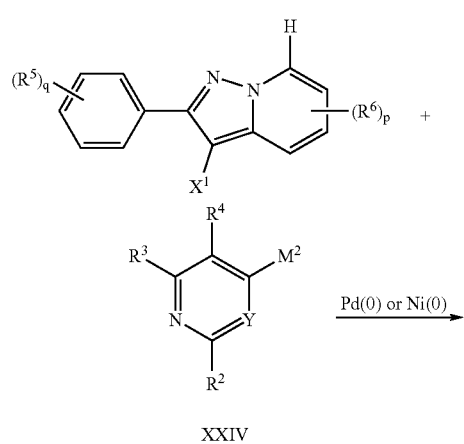

XXIV

-continued

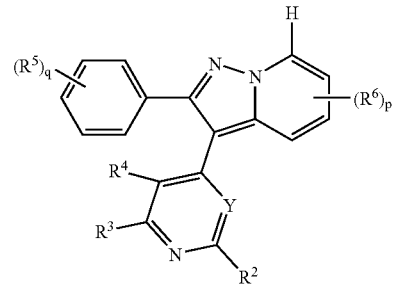

IX wherein all variables are as defined above in connection with Scheme 4.

The reaction may be carried out in an inert solvent, in the presence of a palladium (0) or nickel (0) catalyst. The reaction may optionally be heated to about 50–150° C. Typically, the reaction is performed by reacting equimolar amounts of a compound of formula (XXII) with a Het-metal compound of formula (XXIV), but the reaction may also be performed in the presence of an excess of compound of the formula (XXIV). The palladium or nickel catalyst is typically present in 1–10 mol % compared to the compound of formula (XXII). Examples of suitable palladium catalysts include but are not limited to, tetrakis(triphenylphosphine)palladium (0), dichlorobis(triphenylphosphine)palladium (II), tris(dibenzylideneacetone)dipalladium (0), and bis (diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the Het-metal compound of formula (XXIV) is an arylboronic acid or ester or an arylborinate the reaction is more conveniently carried out by adding a base in a proportion equivalent to, or greater than, that of the compound of formula (XXIV). Het-metal compounds of formula (XXIV) may be obtained from commercial sources or prepared either as discreet isolated compounds or generated in situ using methods known to one skilled in the art. (Suzuki, A. *J. Organomet. Chem.* 1999, 576, 147; Stille, J. *Angew. Chem. Int. Ed. Engl.* 1986, 25, 508; Snieckus, V. *J. Org. Chem.* 1995, 60, 292.)

Compounds of formula (XXII) can be prepared from compounds of formula (VI) by a halogenation procedure.

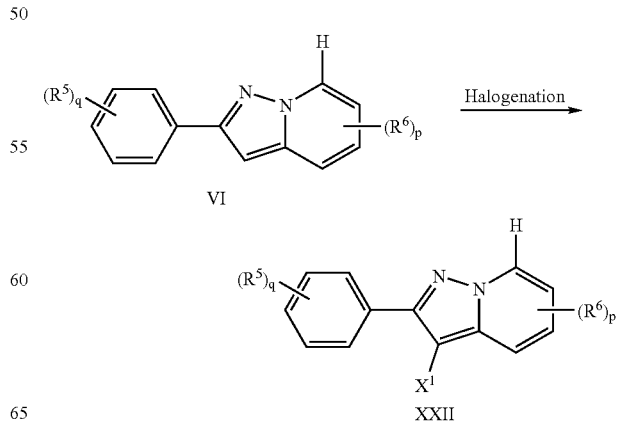

wherein all variables are as defined above in connection with Scheme 4.

Typically, the halogenation reaction is carried out by subjecting the compounds of formula (VI) to a halogenating agent in a suitable solvent. Suitable halogenating agents include but are not limited to, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, and the like.

The compounds of formula (VI) can be prepared according to the methods described above in connection with Scheme 1.

In addition to the foregoing methods of synthesis, the compounds of formula (I) and pharmaceutically acceptable salts, solvates and physiologically functional derivatives thereof may also be prepared using the procedures described in PCT Publication WO02/16359, published to GlaxoSmithkline Inc., the disclosure of which is incorporated herein by reference in its entirety.

As will be apparent to those skilled in the art, the compounds of formula (I) may be converted to other compounds of formula (I) using techniques well known in the art. For example, one method of converting compounds of formula (I) to other compounds of formula (I) comprises a) oxidizing the compound of formula (I-C) to prepare a compound of formula (I-D) and then b) optionally reacting a compound of formula (I-D) with an oxygen or amine nucleophile selected from the group consiting of Het bonded through N, —OR$^7$, —OAy, —OHet, —OR$^{10}$Het, —NR$^7$R$^8$, —NHHet, —NHR$^{10}$Ay and —NHR$^{10}$Het to produce a compound of formula I wherein R$^2$ is selected from the group consisting of Het bonded through N, —OR$^7$, —OAy, —OHet, —OR$^{10}$Het, —NR$^7$R$^8$, —NHHet, —NHR$^{10}$Ay and —NHR$^{10}$Het.

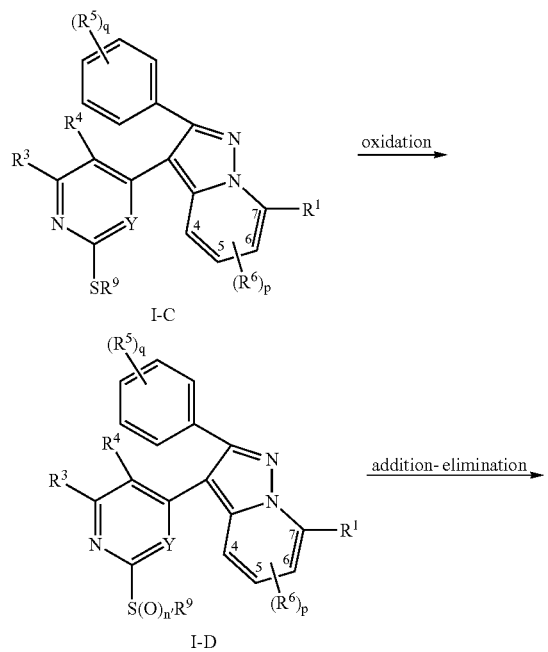

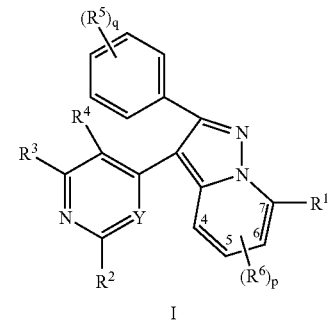

wherein R$^2$ is selected from the group consisting of Het bonded through N, —OR$^7$, —OAy, —OHet, —OR$^{10}$Het, —NR$^7$R$^8$, —NHHet, —NHR$^{10}$Ay and —NHR$^{10}$Het and n' is 1 or 2 and all other variables are as defined in connection with any of the processs described above.

More specifically, compounds of formula (I) can be prepared by reacting a compound of formula (I-D) (i.e., compounds of formula I wherein R$^2$ is S(O)$_{n'}$R$^9$ where n' is 1 or 2) with an oxygen or amine nucleophile selected from the group consisting of Het bonded through N, —OR$^7$, —OAy, —OHet, —OR$^{10}$Het, —NR$^7$R$^8$, —NHHet, —NHR$^{10}$Ay and —NHR$^{10}$Het. The reaction may be carried out neat or in a suitable solvent and may be heated to 50–150° C. Typically the solvent is a lower alcohol such as methanol, ethanol, isopropanol and the like or solvent such as N,N-dimethylformamide or tetrahydrofuran, and the like. Optionally a base may be used to facilitate the reaction. Typically the base can be potassium carbonate, or an amine base such as triethylamine.

Compounds of formula (I-D) may be conveniently prepared by reacting a compound of formula (I-C) (i.e., compounds of formula I wherein R$^2$ is S(O)$_n$R$^9$ where n is 0) with an oxidizing agent in an inert solvent, optionally in the presence of a base. Typically the oxidizing agent is a peracid such as m-chloroperbenzoic acid or the like optionally with a base such as sodium bicarbonate. Careful monitoring of the stoichiometry between the oxidizing agent and the substrate allows the product distribution between sulfoxide (n=1), and sulfone (n=2) to be controlled. Suitable solvents include but are not limited to, dichloromethane, chloroform and the like.

Compounds of formula (I-C) are prepared by methods described above wherein R$^2$ is SR$^9$ from from the reaction of compounds selected from the group consisting of compounds of formula (VIII), compounds of formula (XVI) and compounds of formula (XX) with a compound of formula (X-A) (i.e., the compound of formula (X) wherein R$^2$ is SR$^9$). The requisite compound of formula (X-A) can be obtained from commercial sources or prepared by methods known to one skilled in the art.

Another particularly useful method for converting compounds of formula (I) to other compounds of formula (I) comprises reacting a compound of formula (I-E) (i.e., a compound of formula (I) wherein R$^2$ is fluoro) with an amine nucleophile (including substituted amines, heterocycles and heteroaryls, particularly those linked through N), and optionally heating the mixture to 50–150° C. to prepare a compound of formula (I-F) (i.e., a compound of formula (I) wherein R$^2$ is selected from the group consisting of Het, —NR$^7$R$^8$, —NHHet, —NHR$^{10}$Ay and —NHR$^{10}$Het).

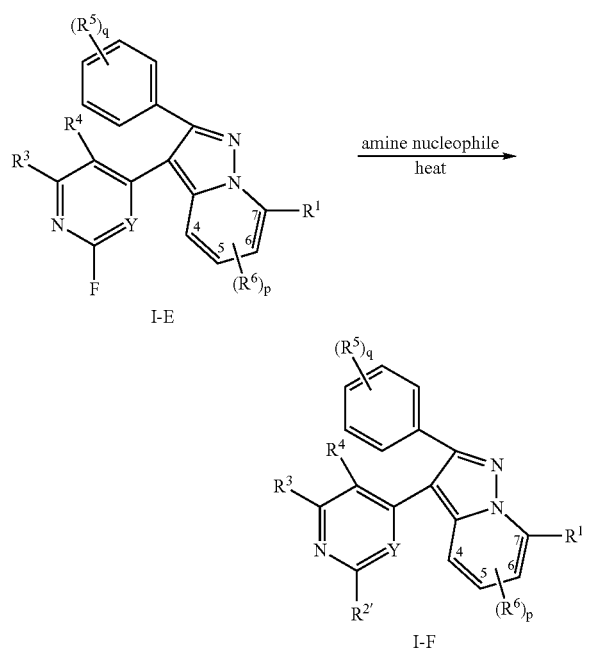

I-E

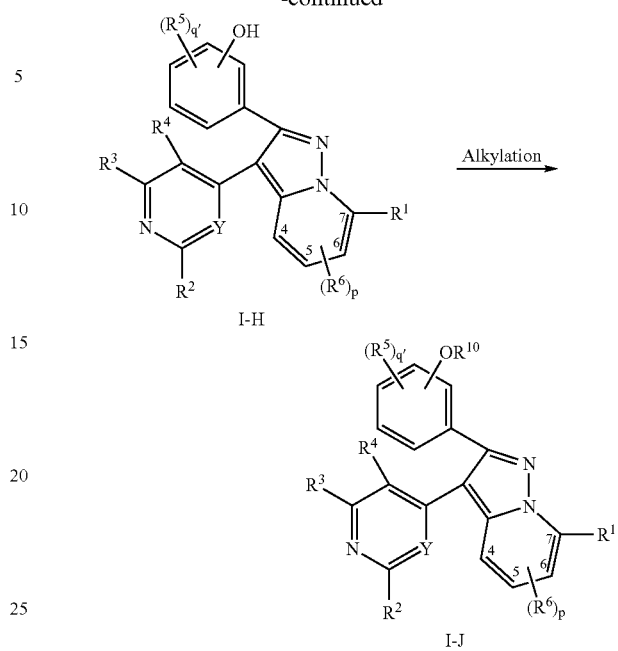

I-H

I-F

I-J wherein R$^{2'}$ is selected from the group consisting of Het, —NR$^7$R$^8$, —NHHet, —NHR$^{10}$Ay, and —NHR$^{10}$Het all other variables are as defined in connection with any of the processes described above.

This procedure may be carried out by mixing a compound of formula (I-E) in an amine nucleophile neat, or in a suitable solvent with an excess of amine nucleophile to produce a compound of formula (I-F). Typically the solvent is a lower alcohol such as methanol, ethanol, isopropanol and the like. Other suitable solvents may include N,N-dimethylformamide, 1-methyl-2-pyrrolidine and the like.

As a further example, compounds of formula (I-G) (i.e., compounds of formula (I) wherein q is 1 or more and at least one R$^5$ is O-methyl) may be converted to compounds of formula (I-H) (i.e., compounds of formula (I) wherein q is 1 or more and at least one R$^5$ is OH) using conventional demethylation techniques. Additionally, compounds of formula (I-H) may optionally be converted to compounds of formula (I-J) (i.e., compounds of formula (I) wherein q is 1 or more and at least one R$^5$ is OR$^{10}$). For example, the foregoing conversions are represented schematically as follows:

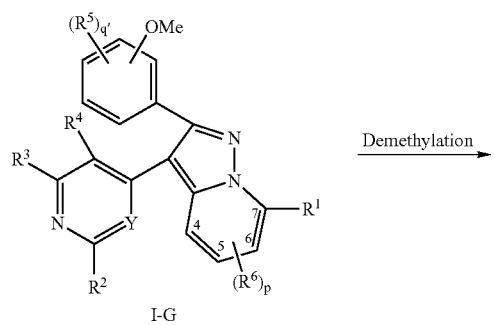

I-G wherein q' is 1, 2, 3 or 4; Me is methyl, and all other variables are as defined in connection with any of the processes described above.

The demethylation reaction may be carried out by treating a compound of formula (I-G) in a suitable solvent with a Lewis acid at a temperature of –78° C. to room temperature, to produce a compound of formula (I-H). Typically the solvent is an inert solvent such as dichloromethane, chloroform, acetonitrile, toluene and the like. The Lewis acid may be boron tribromide, trimethylsilyl iodide or the like.

Optionally, the compounds of formula (I-H) may be further converted to compounds of formula (I-J) by an alkylation reaction. The alkylation reaction may be carried out by treating a compound of formula (I-H) in suitable solvent with an alkyl halide of formula R$^{10}$-Halo where R$^{10}$ is as defined above, to form a compound of formula (I-J). The reaction is typically carried out in the presence of a base and with optionally heating to 50–200° C. The reaction may be carried out in solvents such as N,N-dimethylformamide, dimethylsulfoxide and the like. Typically the base is potassium carbonate, cesium carbonate, sodium hydride or the like. Additionally, as will be apparent to those skilled in the art, the alkylation reaction can be carried out under Mitsunobu conditions.

The foregoing reaction methods can also be used to convert compounds of formula (I) wherein at least one R$^6$ is —OMe to compounds of formula (I) wherein at least one R$^6$ is OH and compounds of formula (I) wherein at least one R$^6$ is —OR$^{10}$. In another embodiment, the foregoing methods are employed to make the same conversion when R$^3$ or R$^4$ is —OMe, to prepare compounds of formula (I) wherein R$^3$ or R$^4$ is —OH or compounds of formula (I) wherein R$^3$ or R$^4$ is —OR$^{10}$.

As a further example of methods for converting compounds of formula (I) to other compounds of formula (I), compounds of formula (I-K) (i.e., compounds of formula (I) wherein q is 1 or more and at least one R$^5$ is halo) may be converted to compounds of formula (I-L) (i.e., compounds of formula (I) wherein q is 1 or more and at least one $R^5$ is Het) or compounds of formula (I-M) (i.e., compounds of formula (I) wherein q is 1 or more and at least one $R^5$ is Ay). For example, the conversion of compounds of formula (I-K) to compounds of formula (I-L) or compounds of formula (I-M) is shown schematically below.

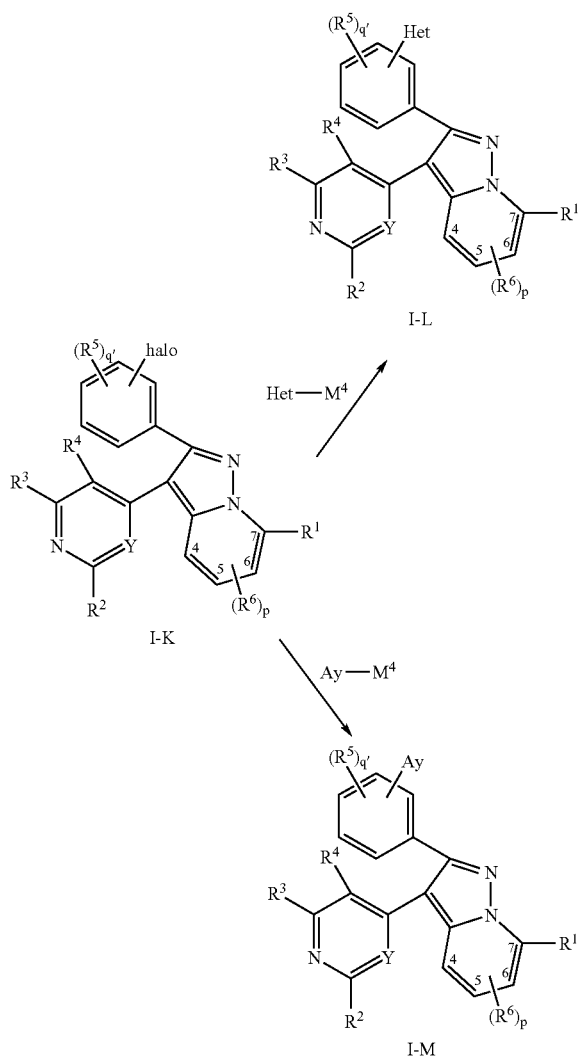

wherein q' is 1, 2, 3 or 4; $M^4$ is selected from the group consisting of —B(OH)$_2$, —B(ORa)$_2$, —B(Ra)$_2$, and —Sn(Ra)$_2$ wherein Ra is alkyl or cycloalkyl; and all other variables are as defined in connection with any of the processes described above.

The conversion of compounds of formula (I-K) to compounds of formula (I-L) or (I-M) is carried out by coupling the compound of formula (I-K) with a compound of formula Het-$M^4$ to make compounds of formula (I-L) or a compound of formula Ay-$M^4$ to make compounds of formula (I-M), where $M^4$ is —B(OH)$_2$, —B(ORa)$_2$, —B(Ra)$_2$, —Sn(Ra)$_2$ wherein Ra is alkyl or cycloalkyl. The reaction may be carried out in an inert solvent, in the presence of a palladium (0) source. The reaction may optionally be heated to 50–150° C. Typically the reaction is performed by reacting equimolar amounts of a compound of formula (I-K) with a compound of formula Het-$M^4$ or Ay-$M^4$ (depending upon whether compounds of formula (I-L) or compounds of formula (I-M) are desired). The reaction may also be performed in the presence of an excess Het-$M^4$ or Ay-$M^4$. The palladium (0) catalyst is typically present in 1–25 mol % compared to the compound of formula (I-K). Examples of suitable palladium catalysts include but are not limited to, tetrakis(triphenylphosphine)palladium (0), dichlorobis(triphenylphosphine)palladium(II), and bis(diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the compound of formula Het-$M^4$ or Ay-$M^4$ is a boronic acid or ester or a borinate the reaction is more conveniently carried out by adding a base in a proportion equivalent to, or greater than, that of the compound of formula Het-$M^4$ or Ay-$M^4$. Compounds of formula Het-$M^4$ and Ay-$M^4$ may be obtained from commercial sources or prepared either as discreet isolated compounds or generated in situ using methods known to one skilled in the art. (Suzuki, A. *J. Organomet. Chem.* 1999, 576,147; Stille, J. *Angew. Chem. Int. Ed. Engl.* 1986, 25, 508; Snieckus, V. *J. Org. Chem.* 1995, 60, 292.)

The foregoing reaction methods can also be used to convert compounds of formula (I) wherein at least one $R^6$ is halo to compounds of formula (I) wherein at least one $R^6$ is Ay or Het. In another embodiment, the foregoing methods are employed to make the same conversion when $R^3$ or $R^4$ is halo, to prepare compounds of formula (I) wherein $R^3$ or $R^4$ is Ay or Het.

In yet another example, compounds of formula (I-K) (i.e., compounds of formula (I) wherein q is 1 or more and at least one $R^5$ is halo) are converted to compounds of formula (I-N) (i.e., compounds of formula (I) wherein q is 1 or more and at least one $R^5$ is —NH$_2$). Optionally, compounds of formula (I-N) may then be converted to compounds of formula (I-O) (i.e., compounds of formula (I) wherein q is 1 or more and at least one $R^5$ is —NR$^7$R$^8$ (where $R^7$ and $R^8$ are not both H). For example, the foregoing conversions are represented schematically as follows:

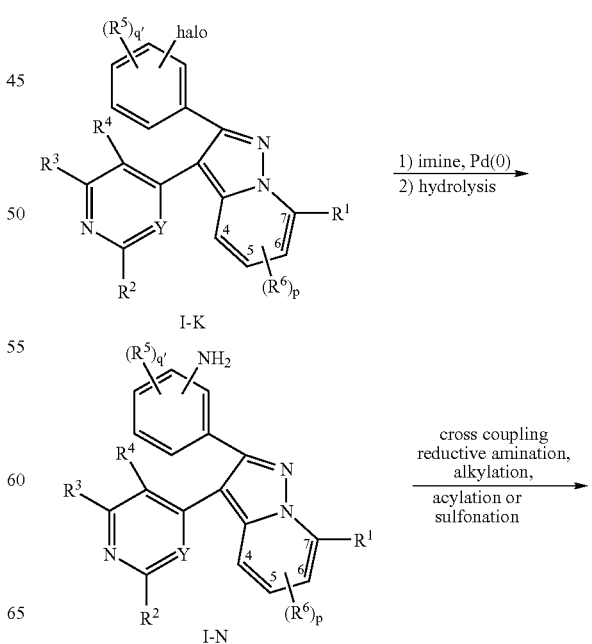

-continued

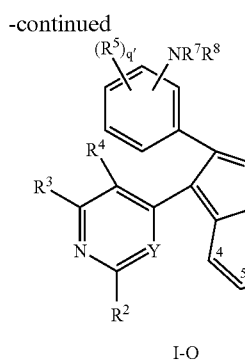

I-O wherein q' is 1, 2, 3 or 4, and all other variables are as defined in connection with any of the processes described above.

The process of converting compounds of formula (I-K) to compounds of formula (I-N) is carried out by reacting a compound of formula (I-K) with an imine in the presence of a palladium (0) source, a base and a suitable ligand, followed by hydrolysis to give a compound of formula (I-N). See J. Wolfe, et al., *Tetrahedron Letters* 38:6367–6370 (1997). Typically the imine is benzophenoneimine, the palladium (0) source is tris(dibenzylideneacetone)dipalladium(0), the base is sodium tert-butoxide and the ligand is racemic-2,2'-bis(diphenylphosphino)-1,1'-binaphthyl. Suitable solvents include N,N-dimethylformamide and the like.

Reaction of a compound of formula (I-N) with compound of formula $R^7$-halogen in a suitable solvent in the presence of base, optionally with heating may be used to prepare compounds of formula (I-O). Typically the base is triethylamine or pyridine and the solvent is N,N-dimethylformamide and the like. Other transformations well known to those skilled in the art for use with anilines may be used to convert compounds of formula (I-N) to compounds of formula (I-O).

Additional compounds of formula (I-O) can be obtained by reductive amination of compounds of formula (I-N) with ketones or aldehydes. See, A. Abdel-Magid, et al., *J. Org. Chem.* 61:3849–3862 (1996). Typically a compound of formula (I-N) is treated with an aldehyde or a ketone in the presence of an acid, such as acetic acid, and a reducing agent, such as sodium triacetoxyborohydride and the like, in an inert solvent such as dichloroethane and the like.

The foregoing reaction methods can also be used to convert compounds of formula (I) wherein at least one $R^6$ is halo to compounds of formula (I) wherein at least one $R^6$ is —$NH_2$ and compounds of formula (I) wherein at least one $R^6$ is —$NR^7R^8$ (where $R^7$ and $R^8$ are not both H). In another embodiment, the foregoing methods are employed to make the same conversion when $R^3$ or $R^4$ is halo, to prepare compounds of formula (I) wherein $R^3$ or $R^4$ is —$NH_2$ or compounds of formula (I) wherein $R^3$ or $R^4$ is —$NR^7R^8$ (where $R^7$ and $R^8$ are not both H).

As a further example, compounds of formula (I-P) (i.e., compounds of formula (I) wherein $R^1$ is Cl, p is 1 and $R^6$ is Cl) may be converted to compounds of formula (I-O) (i.e., compounds of formula (I) wherein $R^1$ is selected from the group consisting of Het, —$NR^7R^8$, —$NR^7Ay$, —NHHet, —$NHR^{10}Ay$ and —$NHR^{10}Het$, p is 1 and $R^6$ is Cl) which may optionally be converted to compounds of formula (I-R) (i.e., compounds of formula (I) wherein $R^1$ is selected from the group consisting of Het, —$NR^7R^8$, —$NR^7Ay$, —NHHet, —$NHR^{10}Ay$ and —$NHR^{10}Het$, p is 1 and $R^6$ is selected from the group consisting of Het, —$NR^7R^8$, —$NR^7Ay$, —NHHet, —$NHR^{10}Ay$ and —$NHR^{10}Het$).

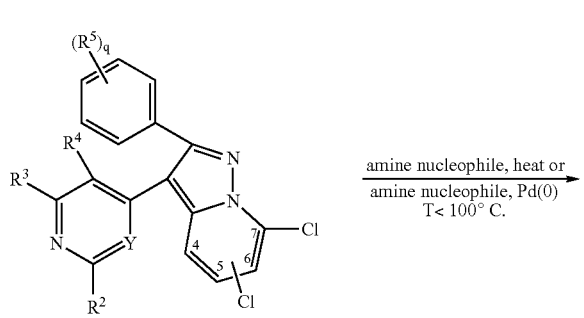

I-P

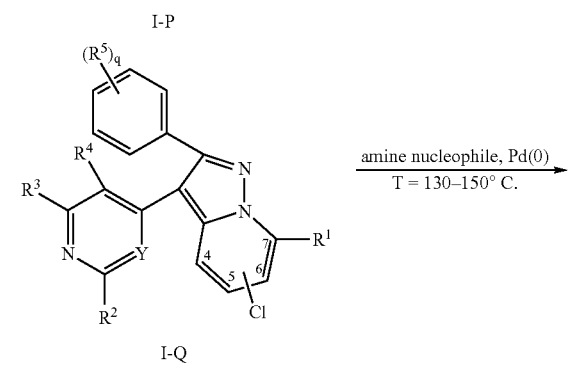

I-Q

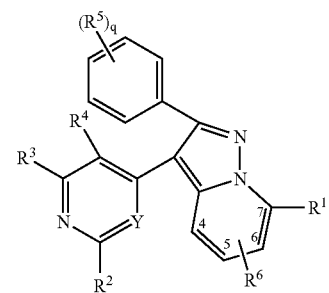

I-R wherein all other variables are as defined in connection with any of the processes described above.

Compounds of formula (I-P) may be converted to compounds of formula (I-Q) by reacting a compound of formula (I-P) with an amine nucleophile selected from the group consisting of Het, —$NR^7R^8$, —$NR^7Ay$, —NHHet, —$NHR^{10}Ay$ and —$NHR^{10}Het$ at elevated temperature or in the presence of a palladium (0) source at an appropriate temperature. The reaction occurs at a temperature of about 80° C. to give a compound of formula (I-Q). Additionally, a compound of formula (I-Q) can be converted into a compound of formula (I-R) by exposure to similar conditions at a temperature of above 100° C. The reagents are similar to those described in connection with Scheme 1. A suitable solvent may include toluene and the like or the reaction may be performed in neat amine.

As another example, compounds of formula (I-S) may be converted to compounds of formula (I-T), which may in turn be converted to compounds of formula (I-U), which may in turn be converted to compounds of formula (I-V), which may in turn be converted to compounds of formula (I-W).

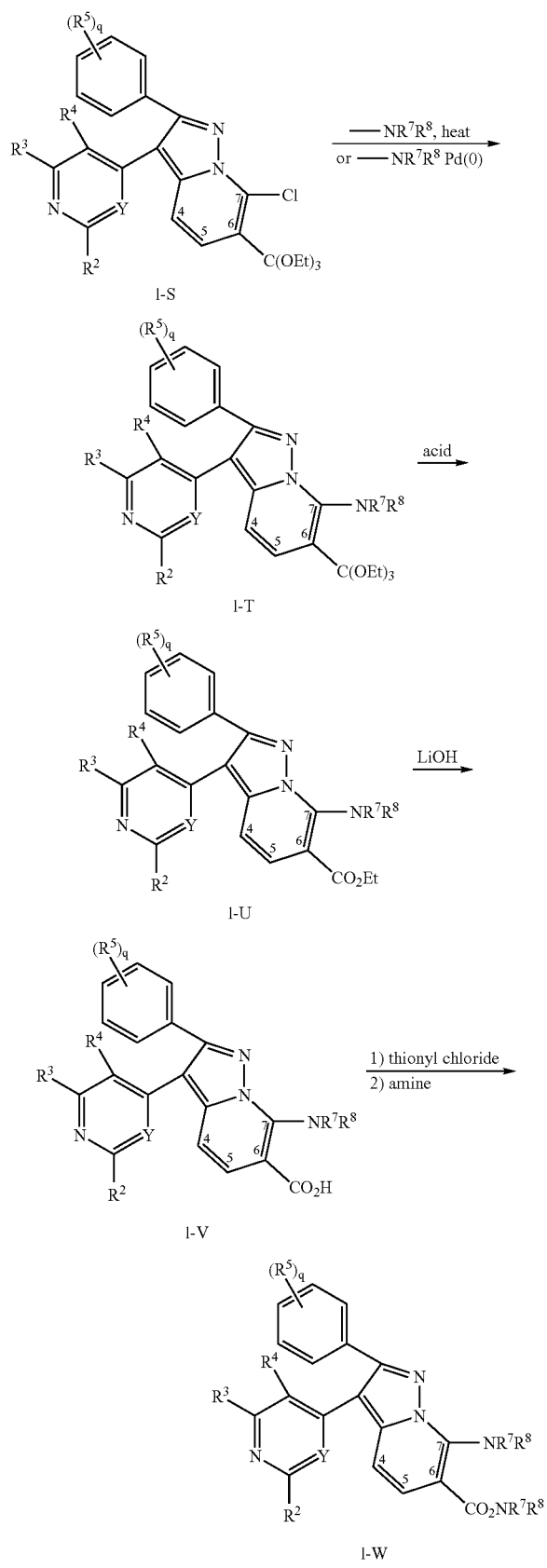

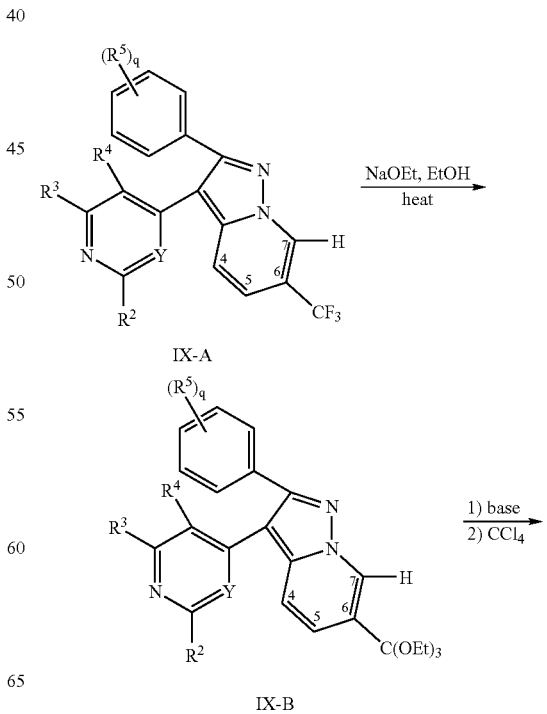

wherein all variables are as defined in connection with any of the processes described above.

A compound of formula (I-T) may be synthesized from a compound of formula (I-S) in a similar manner to that described above in connection with Scheme 1, by exposure of the compound of formula (I-S) to an amine nucleophile of formula —NR$^7$R$^8$ and heat optionally in the presence of a palladium (O) source.

A compound of formula (I-T) can be converted to a compound of formula (I-U) by treatment with an acid in an appropriate solvent. Suitable acids may include but are not limited to p-toluenesulfonic acid, camphorsulfonic acid, pyridinium p-toluenesulfonic acid and the like. An example of an appropriate solvent is acetone.

A compound of formula (I-U) may be converted to a compound of formula (I-V) by a hydrolysis reaction in an appropriate solvent. The hydrolysis can be performed using lithium hydroxide and the like in a pure or mixed solvent system including but not limited to such as solvents as tetrahydrofuran, methanol, and water.

A compound of formula (I-V) can be converted to a compound of formula (I-W) by activation of the acid moiety with an appropriate reagent, followed by exposure to an amine in a suitable solvent. Several acid activating protocols are well known to one skilled in the art, these include but are not limited to thionyl chloride, oxalyl chloride, carbodiimide reagents, carbonyl di-imidazole, pivaloic anhydride and the like. Solvents may include dichloromethane, tetrahydrofuran and the like.

The compounds of formula (I-S) can be prepared using the techniques described above in Schemes 1, 2 and 3. According to one particularly useful method, compounds of formula (I-S) are prepared from compounds of formula (IX-A) as shown below.

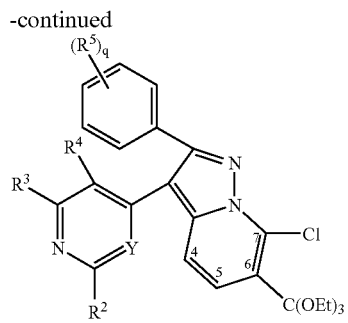

I-S wherein all variables are as defined in connection with any of the processes described above.

A compound of the formula (IX-A) can be converted to a compound of formula (IX-B) by treatment with a metal alkoxide in an alcohol solvent. Suitable conditions include the use of sodium ethoxide as the alkoxide, and ethanol as a choice solvent. The reaction may be heated to 60° C.

As was described in connection with Scheme 1, a halogenation procedure can be performed facilitated by treatment of a compound of formula (IX-B) with a base followed by reaction with a halogenating agent to provide a compound of formula (I-S).

The compounds of formula (IX-A) can be obtained using the procedures described above in Schemes 1, 2 and 3. In one particularly useful embodiment, the compounds of formula (IX-A) are prepared using the procedures described in connection with any of Schemes 1, 2 or 3, with the exception that the first step, i.e., the preparation of compounds of formula (III), involves the condensation of 2-chloro-5-trifluoromethylpyridine with the acetophenone of formula (XXVII):

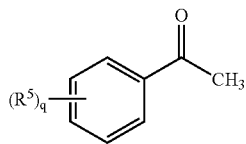

XXVII under basic conditions, in place of the reaction of the picoline of formula (XI) with the benzoylating agent of formula (II) as is employed in the synthesis of the compound of formula (III), as described in Schemes 1, 2 and 3.

In addition, compounds of formula (I-U) may be converted to compounds of formula (I-X) via a reduction reaction.

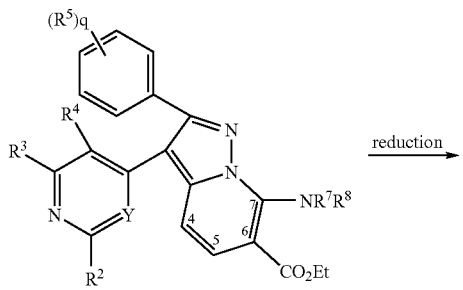

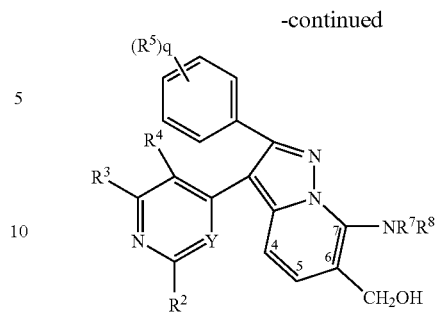

wherein all variables are as defined in connection with any of the processes described above.

Suitable reduction reactions for converting compounds of formula (I-U) to compounds of formula (I-X) are well known to those skilled in the art.

Based upon this disclosure and the examples contained herein one skilled in the art can readily convert compounds of formula (I) (including compounds of formula (I-A) and (I-B)) or a pharmaceutically acceptable salt, solvate or physiologically functional derivativer thereof into other compounds of formula (I) (including (I-A) and (I-B)) or a pharmaceutically acceptable salt, solvate or physiologically functional derivative thereof.

The present invention also provides radiolabeled compounds of formula (I) and biotinylated compounds of formula (I). Radiolabeled compounds of formula (I) and biotinylated compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one embodiment, the compounds of formula (I) are tritiated.

The radiolabeled compounds of formula (I) and biotinylated compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) or the biotinylated compounds of formula (I) to the target protein. More specifically, suitable assay methods will include competition binding assays. The radiolabeled compounds of formula (I) and biotinylated compounds of formula (I) can be employed in assays according to the methods conventional in the art.

The following examples are intended for illustration only and are not intended to limit the scope of the invention in any way, the invention being defined by the claims which follow.

Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

N-Cyclopentyl-2-(4-fluorophenyl)-3-[2-(1-pyrrolidinyl)-4-pyrimidinyl]-6-(trifluoromethyl)pyrazolo[1,5-a]pyridin-7-amine

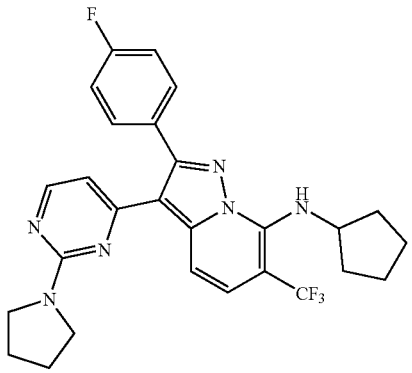

a) 1-(4-Fluorophenyl)-2-(2-(5-trifluoromethyl)pyridyl)ethanone.

To a solution of 4-fluoroacetophenone (13.8 g, 0.100 mol) and 2-chloro-5-trifluoromethylpyridine (20.0 g, 0.110 mol) in tetrahydrofuran (400 mL) was added sodium hydride (95%, 5.56 g, 0.220 mol) in several portions. The reaction was stirred at room temperature for 72 hours then carefully quenched by the addition of water (300 mL) and diethyl ether (200 mL). The organic layer was separated and extracted with 6N HCl (2×300 mL). The aqueous extracts were cooled to 0° C. and 6N NaOH was used to adjust the solution to pH12. The mixture was then extracted with diethyl ether and the combined organic extracts were dried over magnesium sulfate. The drying agent was removed by filtration and the filtrate was evaporated to dryness to afford the title compound as a tautomeric mixture, 20.9 g (73%). $^1$H NMR (CDCl$_3$): δ 8.87(s), 8.63(s), 8.14(dd, J=5.1, 8.4 Hz), 8.00–7.83(m), 7.51(d, J=8.4 Hz), 7.22–7.12(m), 6.13(s), 4.60(s). MS (ES): 284 (M+1).

b) 1-(4-Fluorophenyl)-2-(2-(5-trifluoromethyl)pyridyl)ethanone oxime.

To a solution of 1-(4-fluorophenyl)-2-(2-(5-trifluoromethyl)pyridyl)ethanone (80.0 g, 0.282 mol) in methanol (1 L) at room temperature was added 10% aqueous sodium hydroxide (436 mL, 1.09 mol). The resulting solution was stirred vigorously as solid hydroxylamine hydrochloride (98.0 g, 1.40 mol) was added. The mixture was heated to reflux for 2 hours, treated with decolorizing charcoal while hot, then filtered through Celite while hot. The filtrate was concentrated to one-half its original volume and then cooled to 0° C. with stirring for one hour. The resulting solids were collected by filtration, washed with water, and dried under vacuum at 50° C. overnight to provide the title compound as a light yellow powder, 73.9 g (88%). $^1$H NMR (DMSO-d$_6$): δ 11.60(s, 1H), 8.86(s, 1H), 8.14(dd, 1H, J=2.1. 8.1 Hz), 7.78(dd, 2H, J=5.7, 9.0 Hz), 7.53(d, 1H, J=8.4 Hz), 7.23(t, 2H, J=9.0 Hz), 4.40(s, 2H). MS (ES): 299 (M+1).

c) 3-(4-Fluorophenyl)-2-(2-(5-trifluoromethyl)pyridyl)-2H-azirine.

To a solution of 1-(4-fluorophenyl)-2-(2-(5-trifluoromethyl)pyridyl)ethanone oxime (25.0 g, 0.084 mol) in methylene chloride (400 mL) was added triethylamine (46.7 mL, 0.335 mol). The solution was cooled to 0° C. under a nitrogen atmosphere, and trifluoroacetic anhydride (14.1 mL, 0.100 mol) was added dropwise. The reaction was stirred for 0.5 hours then quenched with water. The organic layer was separated and dried over anhydrous magnesium sulfate. The drying agent was removed by filtration and the solvent was evaporated from the filtrate to leave an oil. The residue was loaded onto a silica gel column and eluted with 15% ethyl acetate in hexanes to give the title compound as an oil which solidified on standing, 19.4 g (82%). $^1$H NMR (CDCl$_3$): δ 8.76(s, 1H), 7.93(dd, 2H, J=5.4, 8.7 Hz), 7.83 (dd, 1H, J=2.1, 8.4 Hz), 7.27(t, 2H, J=8.7 Hz), 7.21(d, 1H, J=8.1 Hz), 3.54 (s, 1H). MS (ES): 281 (M+1).

d) 2-(4-Fluorophenyl)-6-(trifluoromethyl)pyrazolo[1,5-a]pyridine.

3-(4-Fluorophenyl)-2-(2-(5-trifluoromethyl)pyridyl)-2H-azirine (40.0 g, 0.143 mol) was dissolved in 1,2,4-trichlorobenzene (400 mL) and the mixture was heated to 200° C. for 10 hours. The reaction mixture was then cooled to room temperature and poured onto a silica gel column. The column was eluted with hexanes to remove the 1,2,4-trichlorobenzene, and then with 20% diethyl ether in hexanes to elute the product The desired fractions were combined and the solvent was evaporated under reduced pressure to leave the title compound, 28.7 g (71%). $^1$H NMR (CDCl$_3$): δ 8.84(s, 1H), 7.98(dd, 2H, J=5.4, 8.7 Hz), 7.65(d, 1H, J=9.3 Hz), 7.28(d, 1H, J=9.3 Hz), 7.20(t, 2H, J=8.7 Hz), 6.88(s, 1H). MS (ES): 281 (M+1).

e) 1-[2-(4-Fluorophenyl)-6-(trifluoromethyl)pyrazolo[1,5-a]pyridin-3-yl]ethanone.

To a mixture of 2-(4-fluorophenyl)-6-(trifluoromethyl) pyrazolo[1,5-a]pyridine (10.30 g, 36.76 mmol) and acetic anhydride (100 mL) was added conc. sulfuric acid (10 drops) and the mixture was stirred and heated at reflux for 1 hour. The reaction mixture was cooled to room temperature and poured into ice water (300 mL). 2N Aqueous sodium hydroxide solution was added to raise the pH of the solution to about 10 and the resulting orange precipitate was collected by filtration. The solid was washed with water, air-dried, and then dried under vacuum to afford the title compound as an orange solid, 11.87 g (quant.). $^1$H NMR (DMSO-d$_6$): δ 9.58 (s, 1H), 8.41 (d, 1H, J=9.3 Hz), 7.89 (d, 1H, J=9.5 Hz), 7.74 (m, 2H), 7.39 (m, 2H), 2.22 (s, 3H). MS (ES) 323 (M+1).

f) (2E)-3-(Dimethylamino)-1-[2-(4-fluorophenyl)-6-(trifluoromethyl)pyrazolo-[1,5-a]pyridin-3-yl]-2-propen-1-one.

A mixture of 1-[2-(4-Fluorophenyl)-6-(trifluoromethyl) pyrazolo[1,5-a]pyridin-3-yl]ethanone (11.85 g), 36.77 mmol) and N,N-dimethylformamide dimethyl acetal (100 mL) was stirred at reflux for 17 hours. The mixture was cooled to room temperature and then to 0° C. The resulting orange precipitate was collected by filtration, washed with cold hexanes, and dried under vacuum to afford the title compound as an orange solid, 10.17 g (73%). $^1$H NMR (DMSO-d$_6$): δ 9.44 (s, 1H), 8.22 (d, 1H, J=9.4 Hz), 7.75 (m, 2H), 7.65 (d, 1H, J=9.5 Hz), 7.56 (d, 1H, J=12.4 Hz), 7.35 (m, 2H), 5.05 (d, 1H, J=12.3 Hz), 3.04 (s, 3H), 2.56 (s, 3H). MS (+ve ion electrospray) 377 (80), (M+).

g) 2-(4-Fluorophenyl)-3-[2-(1-pyrrolidinyl)-4-pyrimidinyl]-6-(trifluoromethyl)-pyrazolo[1,5-a]pyridine.

To a solution of (2E)-3-(dimethylamino)-1-[2-(4-fluorophenyl)-6-(trifluoromethyl)-pyrazolo[1,5-a]pyridin-3-yl]-2-propen-1-one (100 mg, 0.27 mmol) in 1-methyl-2-pyrrolidinone (3 mL) was added 1-pyrrolidinecarboximidamide sulfate (111 mg, 0.53 mmol), and potassium carbonate (73 mg, 0.53 mmol). The mixture was heated at reflux for 8 hours. Upon cooling to room temperature, ether was added followed by water. The organics were washed with brine, and the aqueous layer was extracted with ether. The combined organics were dried over magnesium sulfate, filtered and concentrated in vacuo. The residue was purified by flash chromatography on silica (6:1 hexanes-ethyl acetate) to give 2-(4-fluorophenyl)-3-[2-(1-pyrrolidinyl)-4-pyrimidinyl]-6-(trifluoromethyl)pyrazolo[1,5-a]pyridine (80 mg, 71%) as a foam. $^1$H NMR (CDCl$_3$): δ 8.86 (s, 1 H), 8.61 (d, 1 H), 8.19 (m, 1 H), 7.67 (m, 2 H), 7.46 (d, 1 H), 7.19 (m, 2 H), 6.31 (m, 1 H), 3.70 (m, 4 H), 2.08 (m, 4 H); $^{19}$F NMR (CDCl$_3$) δ −62.68, −112.27.

h) 7-Chloro-2-(4-fluorophenyl)-3-[2-(1-pyrrolidinyl)-4-pyrimidinyl]-6-(trifluoromethyl)pyrazolo[1,5-a]pyridine.

To a cold (−78° C.) solution of 2-(4-fluorophenyl)-3-[2-(1-pyrrolidinyl)-4-pyrimidinyl]-6-(trifluoromethyl)pyrazolo[1,5-a]pyridine (86 mg, 0.20 mmol) in tetrahydrofuran (5 mL) was added n-butyllithium (0.30 mL, 1.6 M in hexane, 0.48 mmol) dropwise. The dark solution was stirred for 3 minutes, and then carbon tetrachloride (1 mL) was added. After 15 minutes, the bath was removed and the solution allowed to warm to room temperature and stirred an additional 15 minutes. Water was added then ether. The organics were washed with brine, and the aqueous layer was extracted with ether. The combined organics were dried over magnesium sulfate, filtered and concentrated in vacuo. The residue was purified by flash chromatography on silica (4:1 hexanes-ethyl acetate) to give 7-chloro-2-(4-fluorophenyl)-3-[2-(1-pyrrolidinyl)-4-pyrimidinyl]-6-(trifluoromethyl)pyrazolo[1,5-a]pyridine (55 mg, 59%) as a solid. $^1$H NMR (CDCl$_3$): δ 8.50 (d, 1 H), 8.11 (d, 1 H), 7.62 (dd, 2 H), 7.50 (d, 1 H), 7.11 (t, 2 H), 6.22 (d, 1 H), 3.62 (m, 4 H), 2.01 (m, 4 H); MS m/z 462 (M+1).

i) N-Cyclopentyl-2-(4-fluorophenyl)-3-[2-(1-pyrrolidinyl)-4-pyrimidinyl]-6-(trifluoromethyl)pyrazolo[1,5-a]pyridin-7-amine.

To a solution of 7-chloro-2-(4-fluorophenyl)-3-[2-(1-pyrrolidinyl)-4-pyrimidinyl]-6-(trifluoromethyl)pyrazolo[1,5-a]pyridine (54 mg, 0.12 mmol) in toluene (3 mL) was added successively racemic-2,2'-bis(diphenylphosphino)-1,1'-binaphthyl (9.2 mg, 0.013 mmol), cesium carbonate (57 mg, 0.17 mmol), cyclopentylamine (0.5 mL, 5.0 mmol), and palladium (II) acetate (2 mg, 0.009 mmol). The resultant mixture was heated at 85° C. for 6 hours at which time the reaction was judged complete by thin layer chromatography. The solution was cooled to room temperature and ether was added. The organic layer was washed with water and brine. The aqueous layer was extracted with ether and the combined organics dried over magnesium sulfate. Filtration and concentration followed by flash chromatography (12:1 to 8:1 hexanes-ethyl acetate) provided N-cyclopentyl-2-(4-fluorophenyl)-3-[2-(1-pyrrolidinyl)-4-pyrimidinyl]-6-(trifluoromethyl)pyrazolo[1,5-a]pyridin-7-amine (37 mg, 63%) as an oil. $^1$H NMR (CDCl$_3$): δ 8.16 (d, 1 H), 7.84 (d, 1 H), 7.68 (dd, 2 H), 7.49 (d, 1 H), 7.18 (t, 2 H), 6.55 (d, 1 H), 6.29 (d, 1 H), 4.57 (m, 1 H), 3.68 (m, 4 H), 2.13–2.05 (m, 6 H), 1.84–1.65 (m, 6 H); $^{19}$F NMR (CDCl$_3$) δ −55.33, −112.78; MS m/z 511 (M+1). This material was taken up in ether and treated with hydrochloric acid in ether to yield a bright yellow powder which was isolated by filtration as a hydrochloride salt.

EXAMPLE 2

N-Cyclopentyl-3-[2-(cyclopentylamino)-4-pyrimidinyl]-2-(4-fluorophenyl)-6-(trifluoromethyl)pyrazolo[1,5-a]pyridin-7-amine

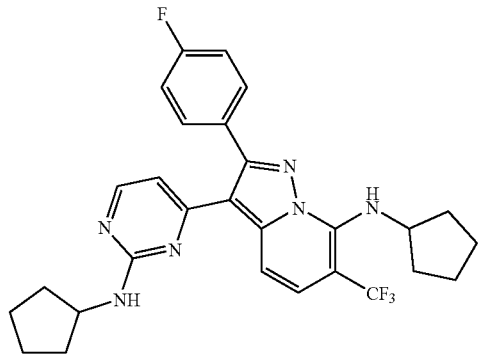

a) N-Cyclopentyl-4-[2-(4-fluorophenyl)-6-(trifluoromethyl)pyrazolo[1,5-a]pyridin-3-yl]-2-pyrimidinamine.

In a similar manner as described in Example 1 from (2E)-3-(dimethylamino)-1-[2-(4-fluorophenyl)-6-(trifluoromethyl)pyrazolo[1,5-a]pyridin-3-yl]-2-propen-1-one (314 mg, 0.83 mmol) and N-cyclopentylguanidine hydrochloride (271 mg, 1.66 mmol) was formed N-cyclopentyl-4-[2-(4-fluorophenyl)-6-(trifluoromethyl)pyrazolo[1,5-a]pyridin-3-yl]-2-pyrimidinamine (204 mg, 56%) as a white solid. $^1$H NMR (CDCl$_3$): δ 8.84 (s, 1 H), 8.51 (d, 1 H), 8.11 (d, 1 H). 7.64 (dd, 2 H), 7.44 (dd, 1 H), 7.17 (t, 2 H), 6.33 (d, 1 H), 5.17 (d, 1 H), 4.34 (m, 1 H), 2.15–2.06 (m, 2 H), 1.84–1.52 (m, 6 H); $^{19}$F NMR (CDCl$_3$): δ −62.70, −112.25; MS m/z 442 (M+1); mp 155–156° C.

b) 4-[7-Chloro-2-(4-fluorophenyl)-6-(trifluoromethyl)pyrazolo[1,5-a]pyridin-3-yl]-N-cyclopentyl-2-pyrimidinamine.

In a similar manner as described in example 1 from N-cyclopentyl-4-[2-(4-fluorophenyl)-6-(trifluoromethyl)pyrazolo[1,5-a]pyridin-3-yl]-2-pyrimidinamine (75 mg, 0.17 mmol) was formed 4-[7-chloro-2-(4-fluorophenyl)-6-(trifluoromethyl)pyrazolo[1,5-a]pyridin-3-yl]-N-cyclopentyl-2-pyrimidinamine (45 mg, 55%). $^1$H NMR (CDCl$_3$): δ 8.42 (d, 1 H), 8.06 (d, 1 H), 7.61 (dd, 2 H), 7.49 (d, 1 H), 7.12 (t, 2 H), 6.27 (d, 1 H), 5.18 (d, 1 H), 4.28 (m, 1 H), 2.07–2.01 (m, 2 H), 1.73–1.49 (m, 6 H); MS m/z 476 (M+1).

c) N-Cyclopentyl-3-[2-(cyclopentylamino)-4-pyrimidinyl]-2-(4-fluorophenyl)-6-(trifluoromethyl)pyrazolo[1,5-a]pyridin-7-amine.

In a similar manner as described in example 1 from 4-[7-chloro-2-(4-fluorophenyl)-6-(trifluoromethyl)pyrazolo[1,5-a]pyridin-3-yl]-N-cyclopentyl-2-pyrimidinamine (45 mg, 0.09 mmol) was formed N-cyclopentyl-3-[2-(cyclopentylamino)-4-pyrimidinyl]-2-(4-fluorophenyl)-6-(trifluoromethyl)pyrazolo[1,5-a]pyridin-7-amine (38 mg, 77%) as an oil. ¹H NMR (CDCl₃): δ 8.11 (d, 1 H), 7.76 (d, 1 H), 7.67 (dd, 2 H), 7.48 (d, 1 H), 7.18 (t, 2 H), 6.54 (d, 1 H), 6.33 (d, 1 H), 5.17 (d, 1 H), 4.57 (m, 1 H), 4.35 (m, 1 H), 2.14–2.06 (m, 4 H), 1.84–1.54 (m, 12 H); ¹⁹F NMR CDCl₃): δ −55.33, −112.73; MS m/z 525 (M+1). This material was taken up in ether and treated with hydrochloric acid in ether to yield a yellow powder which was isolated by filtration as a hydrochloride salt.

EXAMPLE 3

Ethyl 7-(cyclopentylamino)-3-[2-(cyclopentylamino)-4-pyrimidinyl]-2-(4-fluorophenyl)pyrazolo[1,5-a]pyridine-6-carboxylate

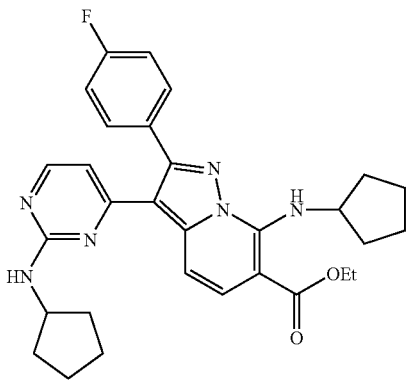

a) 2-(4-Fluorophenyl)-6-(trifluoromethyl)pyrazolo[1,5-a]pyridine-3-carbaldehyde.

To a cold (0° C.) solution of phosphorus oxychloride (8.0 mL, 86 mmol) in N,N-dimethylformamide (160 mL) was added 2-(4-fluorophenyl)-6-(trifluoromethyl)pyrazolo-[1,5-a]pyridine (11.0 g, 39.3 mmol). The reaction mixture was stirred at room temperature for 72 hours, then quenched with ice water. The solid precipitate was collected on a filter to provide 2-(4-fluorophenyl)-6-(trifluoromethyl)pyrazolo[1,5-a]pyridine-3-carbaldehyde (11.4 g, 94%) as a white solid. R$_f$ 0.45 (4:1 hexanes:ethyl acetate); ¹H NMR (400 MHz, CDCl₃) δ 10.15 (s, 1H), 8.92 (s, 1H), 8.53 (d, 1H), 7.80 (m, 2H), 7.70 (d,₁H), 7.27 (t, 2H); ¹⁹F NMR (CDCl₃) δ −62.62, −110.62; MS m/z 307 (M−1).

b) 1-[2-(4-Fluorophenyl)-6-(trifluoromethyl)pyrazolo[1,5-a]pyridin-3-yl]-2-propyn-1-ol.

To a cold (−78° C.) suspension of 2-(4fluorophenyl)-6-(trifluoromethyl)pyrazolo[1,5-a]pyridine-3-carbaldehyde (11.4 g, 37.0 mmol) in tetrahydrofuran (100 mL) was added ethynylmagnesium bromide (111 mL, 0.5 M in tetrahydrofuran, 56 mmol). The reaction mixture was warmed to room temperature and stirred for 14 hours. The reaction mixture was poured into water and adjusted to neutral pH with 1N aqueous hydrochloric acid. The aqueous mixture was extracted with ethyl acetate. The combined extracts were washed with water and brine. The organic layer was dried over magnesium sulfate. Filtration and concentration provided 1-[2-(4-fluorophenyl)-6-(trifluoromethyl)pyrazolo[1,5-a]pyridin-3-yl]-2-propyn-1-ol (11.9 g, 96%) as a tan solid. R$_f$ 0.18 (4:1 hexanes:ethyl acetate); ¹H NMR (300 MHz, CDCl₃) δ 8.81 (s, 1H), 8.15 (d, 1H), 7.75 (m, 2H), 7.35 (d, 1H), 7.19 (t, 2H), 5.76 (s, 1H), 2.71 (d, 1H, 2.60 (d, 1H); MS m/z 335 (M+1).

c) 1-[2-(4-Fluorophenyl)-6-(trifluoromethyl)pyrazolo[1,5-a]pyridin-3-yl]-2-propyn-1-one.

To a cold (0° C.) solution of 1-[2-(4-fluorophenyl)-6-(trifluoromethyl)pyrazolo[1,5-a]pyridin-3-yl]-2-propyn-1-ol (5.00 g. 15.0 mmol) in chloroform (400 mL) was added manganese dioxide (130 g, 1.50 mol). The reaction mixture was stirred at 0° C. for 1.5 hours. The reaction mixture was filtered through a pad of Celite. The filtrate was concentrated in vacuo to provide 1-[2-(4-fluorophenyl)-6-(trifluoromethyl)pyrazolo[1,5-a]pyridin-3-yl]-2-propyn-1-one (3.44 g, 69%) as a clear oil. R$_f$ 0.39 (4:1 hexanes:ethyl acetate); ¹H NMR (400 MHz, CDCl₃) δ 8.90 (s, 1H), 8.61 (d,₁H), 7.72–7.69 (m, 3H), 7.17 (m, 2H), 3.06 (s,₁H); MS m/z 333 (M+1).

d) N-Cyclopentyl-4-[2-(4-fluorophenyl)-6-(trifluoromethyl)pyrazolo[1,5-a]pyridin-3-yl]-2-pyrimidinamine.

To a suspension of N-cyclopentylguanidine hydrochloride (2.20 g, 13.5 mmol) in ethanol (70 mL) was added sodium ethoxide (4.5 mL, 3 M in ethanol, 14 mmol). The mixture was stirred at room temperature for 30 minutes, then cooled to 0° C. To this mixture was added 1-[2-(4-fluorophenyl)-6-(trifluoromethyl)pyrazolo[1,5-a]pyridin-3-yl]-2-propyn-1-one (3.44 g, 10.4 mmol) portionwise. The reaction mixture was stirred at 0° C. for 30 minutes, followed by room temperature for 15 hours. The reaction mixture was diluted with water (400 mL). The solid precipitate was collected on a filter to provide N-cyclopentyl-4-[2-(4-fluorophenyl)-6-(trifluoromethyl)pyrazolo[1,5-a]pyridin-3-yl]-2-pyrimidinamine (4.48 g, 98%) as an orange solid. ¹H NMR (400 MHz, CDCl₃) δ 8.84 (s, 1 H), 8.51 (d, 1 H), 8.11 (d, 1 H), 7.64 (dd, 2 H), 7.44 (dd, 1 H), 7.17 (t, 2 H), 6.33 (d, 1 H), 5.17 (d, 1 H), 4.34 (m, 1 H), 2.15–2.06 (m, 2 H), 1.84–1.52 (m, 6 H); ¹⁹F NMR (CDCl₃): δ −62.70, −112.25 MS m/z 442 (M+1); mp 155–156° C.

e) N-Cyclopentyl-4-[2-(4-fluorophenyl)-6-(triethoxymethyl)pyrazolo[1,5-a]pyridin-3-yl]-2-pyrimidinamine.

To a dry round bottom flask was added sodium metal (1.9 g, 83 mmol). Ethanol (110 mL) was added and allowed to react with sodium at room temperature until completely dissolved. N-Cyclopentyl-4-[2-(4-fluorophenyl)-6-(trifluoromethyl)pyrazolo[1,5-a]pyridin-3-yl]-2-pyrimidinamine (4.48 g, 10.1 mmol) was added and the reaction mixture was stirred at 60° C. for 18 hours. The reaction mixture was cooled and concentrated in vacuo to approximately one-fourth of the original volume. The resulting mixture was diluted with water and extracted with ethyl acetate. The organic layer was washed with water and brine, then dried over magnesium sulfate. Filtration and concentration provided N-cyclopentyl-4-[2-(4-fluorophenyl)-6-(triethoxymethyl)-pyrazolo[1,5-a]pyridin-3-yl]-2-pyrimidinamine (4.86 g, 92%) as an off-white solid. R$_f$ 0.15 (4:1 hexanes:ethyl acetate); ¹H NMR (300 MHz, CDCl₃) δ 8.81 (s, 1H), 8.39 (d, 1H), 8.06 (d, 1H), 7.62 (m, 2H), 7.47 (d, 1 H), 7.14 (t, 2H), 6.32 (d, 1H), 5.12 (d, 1H), 4.35 (m, 1H), 3.43 (q, 6H), 2.08 (m, 2H), 1.80–151 (m, 6H), 1.21 (t, 9H); MS m/z 520 (M+1).

f) 4-[7-Chloro-2-(4-fluorophenyl)-6-(triethoxymethyl)pyrazolo[1,5-a]pyridin-3-yl]-N-cyclopentyl-2-pyrimidinamine.

To a cold (0° C.) solution of diisopropylamine (4.1 mL, 29 mmol) in tetrahydrofuran (25 mL) was added butyllithium (17 mL, 1.6 M in hexanes, 28 mmol) dropwise. The resultant solution was stirred at 0° C. for 10 minutes then cooled to −78° C. The reaction mixture was transferred via syringe to a cold (−78° C.) solution of N-cyclopentyl-4-[2-(4-fluorophenyl)-6-(triethoxymethyl)pyrazolo[1,5-a]pyridin-3-yl]-

2-pyrimidinamine (4.86 g, 9.35 mmol) in tetrahydrofuran (25 mL). The reaction mixture was stirred at −78° C. for 30 minutes. Carbon tetrachloride (3.6 mL, 37 mmol) was added and the resulting mixture was warmed to room temperature and stirred for 2 hours. The reaction mixture was poured onto ice. After the ice had melted, the aqueous mixture was extracted with ethyl acetate. The organic layer was washed with water and brine, then dried over sodium sulfate. Filtration and concentration followed by flash chromatography (4:1 hexanes:ethyl acetate) provided 4-[7-chloro- 2-(4-fluorophenyl)-6-(triethoxymethyl)pyrazolo[1,5-a]pyridin-3-yl]-N-cyclopentyl-2-pyrimidinamine (2.37 g, 46%) as a yellow solid. $R_f$ 0.36 (4:1 hexanes:ethyl acetate); $^1$H NMR (400 MHz, CDCl$_3$) δ 8.36 (d, 1H), 8.08 (d, $_1$H), 7.85 (d, 1H), 7.67 (m, 2H), 7.15 (t, 2H), 6.33 (d, 1H), 5.15 (d, 1H), 4.36 (m, 1H), 3.46 (q, 6H), 2.10 (m, 2H), 1.81–1.53 (m, 6H), 1.26 (t, 9H); MS m/z 554 (M+1).

g) N-Cyclopentyl-3-[2-(cyclopentylamino)-4-pyrimidinyl]-2-(4-fluorophenyl)-6-(triethoxymethyl)pyrazolo[1,5-a]pyridin-7-amine.

A mixture of 4-[7-chloro-2-(4-fluorophenyl)-6-(triethoxymethyl)pyrazolo[1,5-a]pyridin-3-yl]-N-cyclopentyl-2-pyrimidinamine (2.37 g, 4.28 mmol) and cyclopentylamine (10 mL, 100 mmol) was heated in a sealed tube at 80° C. for 16 hours. The reaction mixture was cooled to room temperature and excess cyclopentylamine was removed in vacuo. The crude solid was triturated in water. The solids were collected on a filter to provide N-cyclopentyl-3-[2-(cyclopentylamino)-4-pyrimidinyl]-2-(4-fluorophenyl)-6-(triethoxymethyl)pyrazolo[1,5-a]pyridin-7-amine (2.48 g, 96%). $R_f$ 0.42 (4:1 hexanes:ethyl acetate); $^1$H NMR (300 MHz, CDCl$_3$) δ 8.04 (d, 1H), 7.75 (d, 1H), 7.68–7.60 (m, 3H), 7.12 (t, 2H), 6.36–6.31 (m, 2H), 5.30 (m, 1H), 5.07 (d, 1H), 4.53 (m, 1H), 3.45 (q, 6H), 2.12–1.95 (m, 4H), 1.80–1.45 (m, 12H), 1.25 (t, 9H); MS m/z 603 (M+1).

h) Ethyl 7-(cyclopentylamino)-3-[2-(cyclopentylamino)-4-pyrimidinyl]-2-(4-fluorophenyl[1,5-a]pyridine-6-carboxylate.

To a suspension of N-cyclopentyl-3-[2-(cyclopentylamino)-4-pyrimidinyl]-2-(4-fluorophenyl)-6-(triethoxymethyl)pyrazolo[1,5-a]pyridin-7-amine (2.48 g, 4.11 mmol) in acetone (80 mL) and water (20 mL) was added p-toluenesulfonic acid monohydrate (1.95 g, 10.2 mmol). The reaction mixture was stirred at room temperature for 3 hours, then poured onto ice and neutralized with a solution of saturated aqueous sodium bicarbonate. The aqueous mixture was concentrated in vacuo to remove the acetone. The resulting aqueous mixture was extracted with ethyl acetate. The organic layer was washed with water and brine, then dried over magnesium sulfate. Filtration and concentration followed by flash chromatography (4:1 hexanes:ethyl acetate to 100% ethyl acetate to 4:1 ethyl acetate:methanol) provided ethyl 7-(cyclopentylamino)-3-[2-(cyclopentylamino)-4-pyrimidinyl]-2-(4-fluorophenyl[1,5-a]pyridine-6-carboxylate (1.9 g, 88%) as a light yellow solid. $R_f$ 0.20 (4:1 hexanes:ethyl acetate); $^1$H NMR (300 MHz, CDCl$_3$): δ 9.27 (d, 1H), 8.08 (d, 1H), 7.78 (d, 1H), 7.64 (m, 2H), 7.47 (d, 1H), 7.12 (t, 2H), 6.32 (d, 1H), 5.51 (m, 1H), 5.11 (d, 1H), 4.38–4.28 (m, 3H), 2.13–2.01 (m, 4H), 1.82–1.50 (m, 12H), 1.41 (t, 3H); MS m/z 529 (M+1).

EXAMPLE 4

7-(Cyclopentylamino)-3-[2-(cyclopentylamino)-4-pyrimidinyl]-2-(4-fluorophenyl)pyrazolo[1,5-a]pyridine-6-carboxylic acid

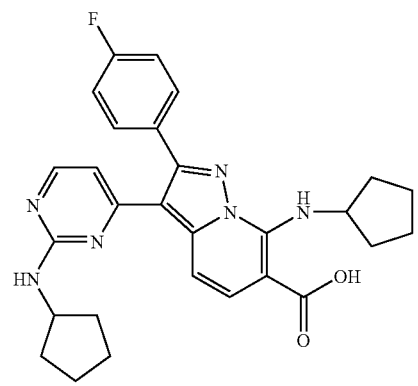

To a solution of ethyl 7-(cyclopentylamino)-3-[2-(cyclopentylamino)-4-pyrimidinyl]-2-(4-fluorophenyl)pyrazolo[1,5-a]pyridine-6-carboxylate (200 mg, 0.378 mmol) in dioxane (5 mL) and water (700 μL) was added lithium hydroxide monohydrate (48 mg, 1.1 mmol). The reaction mixture was heated for 40 hours at 100° C. The reaction mixture was cooled and concentrated in vacuo, then diluted with water. The aqueous mixture was acidified with 1 N aqueous hydrochloric acid. The solid precipitate was collected on a filter to provide 7-(cyclopentylamino)-3-[2-(cyclopentylamino)-4-pyrimidinyl]-2-(4-fluorophenyl)pyrazolo[1,5-a]pyridine-6-carboxylic acid dihydrochloride (125 mg, 58%) as an orange solid. $^1$H NMR (400 MHz, DMSO-d$_6$): δ 13.07 (broad, 1H). 9.46 (d, 1H), 8.07 (d, 1H), 7.78 (d, 1H), 7.66 (m, 2H), 7.34 (t, 2H), 6.28 (broad, 1H), 5.37 (m, 1H), 4.11 (broad, 1H), 1.99 (m, 2H), 1.87 (broad, 2H), 1.74–1.48 (m, 12H); MS m/z 501 (M+1).

EXAMPLE 5

N-Cyclopentyl-3-[2-(cyclopentylamino)-4-pyrimidinyl]-2-(4-fluorophenyl)-6-(1-pyrrolidinylcarbonyl)pyrazolo[1,5-a]pyridin-7-amine

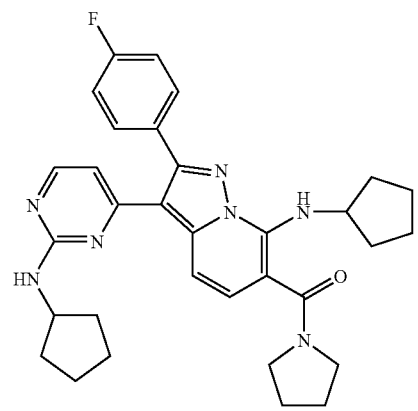

7-(Cyclopentylamino)-3-[2-(cyclopentylamino)-4-pyrimidinyl]-2-(4-fluorophenyl)pyrazolo[1,5-a]pyridine-6-carboxylic acid dihydrochloride (19 mg, 0.033 mmol) was added to a dry flask and cooled to −78° C. Thionyl chloride (14 μL, 0.19 mmol) was added and the reaction mixture was stirred at room temperature for 30 minutes. The reaction mixture was concentrated under a stream of nitrogen then placed under high vacuum. To a solution of the crude residue in dichloromethane (600 μL) was added pyrrolidine (150 μL, 1.80 mmol). The reaction mixture was stirred at room temperature for 10 minutes then partitioned between ethyl acetate and saturated aqueous sodium bicarbonate solution. The aqueous layer was extracted with ethyl acetate. The combined extracts were washed with water and brine, then dried over magnesium sulfate. Filtration and concentration followed by flash chromatography (1:1 hexanes:ethyl acetate to 100% ethyl acetate) provided N-cyclopentyl-3-[2-(cyclopentylamino)-4-pyrimidinyl]-2-(4-fluorophenyl)-6-(1-pyrrolidinylcarbonyl)pyrazolo[1,5-a]pyridin-7-amine (9 mg, 49%) as a clear oil. R$_f$ 0.13 (1:1 hexanes:ethyl acetate); $^1$H NMR (300 MHz, CDCl$_3$) δ 8.04 (d, 1H), 7.72 (d, 1H), 7.62 (m, 2H), 7.26 (d, 1H), 7.14(t, 2H), 6.54(d, 1H), 6.30(d, 1H), 5.11 (d, 1H), 4.31 (m, 1H), 4.19 (m, 1H), 3.66 (broad, 2H), 3.38 (broad, 2H), 2.11–1.88 (m, 8H), 1.80–1.50 (m, 12H); MS m/z 554 (M+1). To a solution of the product in ether was added 1 M HCl in ether. The precipitated solid was isolated to give the corresponding HCl salt.

EXAMPLE 6

7-(Cyclopentylamino)-3-[2-(cyclopentylamino)-4-pyrimidinyl]-2-(4-fluorophenyl)-N,N-dimethylpyrazolo[1,5-a]pyridine-6-carboxamide

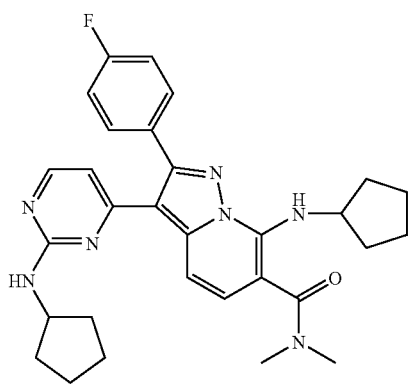

In a similar manner as described in Example 5 from 7-(cyclopentylamino)-3-[2-(cyclopentylamino-4-pyrimidinyl]-2-(4fluorophenyl)pyrazolo[1,5-a]pyridine-6-carboxylic acid dihydrochloride (41 mg, 0.071 mmol) and dimethylamine (500 μL, 2.0 M in tetrahydrofuran, 0.25 mmol) was formed 7-(cyclopentylamino)-3-[2-(cyclopentylamino)-4-pyrimidinyl]-2-(4-fluorophenyl)-N,N-dimethylpyrazolo[1,5-a]pyridine-6-carboxamide (14 mg, 38%) as a clear oil. R$_f$ 0.12 (1:1 hexanes:ethyl acetate); $^1$H NMR (400 MHz, CDCl$_3$): δ 8.04 (d, 1H), 7.73 (d, 1H), 7.63 (m, 2H), 7.19 (d, 1H), 7.15 (t, 2H), 6.51 (d, $_1$H), 6.30 (d, 1H), 5.17 (d, 1H), 4.32 (m, 1H), 4.13 (m, 1H), 3.09 (broad, 6H), 2.11–1.95 (m, 4H), 1.80–1.51 (m, 12H); MS m/z 528 (M+1). To a solution of the product in ether was added 1 M HCl in ether. The precipitated solid was isolated to give the corresponding HCl salt.

EXAMPLE 7

7-(Cyclopentylamino)-3-[2-(cyclopentylamino)-4-pyrimidinyl]-2-(4-fluorophenyl)-N-hydroxypyrazolo[1,5-a]pyridine-6-carboxamide

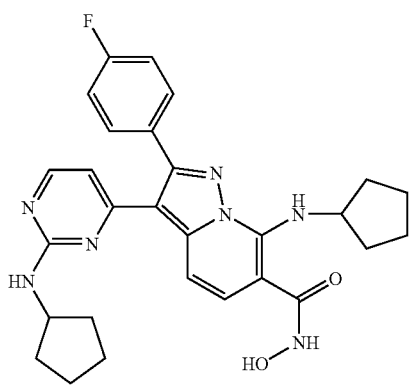

7-(Cyclopentylamino)-3-[2-(cyclopentylamino)-4-pyrimidinyl]-2-(4-fluorophenyl)pyrazolo[1,5-a]pyridine-6-carboxylic acid dihydrochloride (52 mg, 0.091 mmol) was added to a dry flask and cooled to −78° C. Thionyl chloride (38 μL, 0.52 mmol) was added and the reaction mixture was stirred at room temperature for 30 minutes. The reaction mixture was concentrated under a stream of nitrogen then placed under high vacuum. In a separate flask, a suspension of hydroxylamine hydrochloride (29 mg, 0.42 mmol) and potassium carbonate (29 mg, 0.21 mmol) in tetrahydrofuran (600 μL) was stirred at room temperature for 30 minutes. To this suspension was added a solution of the crude acid chloride in dichloromethane (600 μL). The resulting mixture was stirred at room temperature for 16 hours. The reaction mixture was diluted with ethyl acetate and washed with saturated aqueous sodium bicarbonate solution, water, and brine. The organic layer was dried over magnesium sulfate. Filtration and concentration followed by chromatography (100% ethyl acetate to 9:1 ethyl acetate:methanol) provided 7-(cyclopentylamino)-3-[2-(cyclopentylamino)-4-pyrimidinyl]-2-(4-fluorophenyl)-N-hydroxypyrazolo[1,5-a]pyridine-6-carboxamide (12 mg, 26%) as a brownish-yellow solid. R$_f$ 0.42 (19:1 ethyl acetate:methanol); $^1$H NMR (400 MHz, CDCl$_3$): δ 8.05 (broad 2H), 7.60 (m, 2H), 7.50 (broad, 1H), 7.21 (broad, 1H), 7.13 (t, 2H), 6.29 (d, 1H), 5.91 (broad, 1H), 4.92 (broad, 1H), 4.31 (m, 1H), 2.10–1.97 (broad, 4H), 1.82–1.54 (broad, 12H); MS m/z 516 (M+1).

EXAMPLE 8

7-(Cyclopentylamino)-3-[2-(cyclopentylamino)-4-pyrimidinyl]-2-(4-fluorophenyl)-N-[2-(4-morpholinyl)ethyl]pyrazolo[1,5-a]pyridine-6-carboxamide

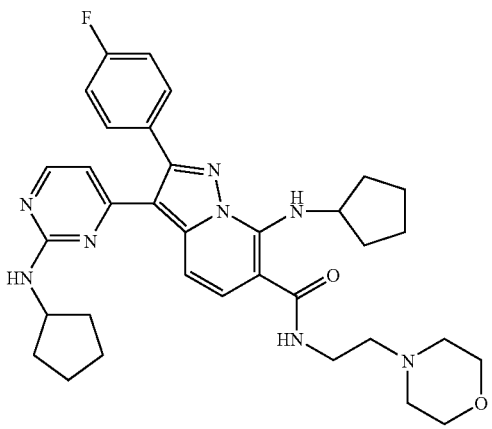

In a similar manner as described in Example 5 from 7-(cyclopentylamino)-3-[2-(cyclopentylamino)-4-pyrimidinyl]-2-(4-fluorophenyl)pyrazolo[1,5-a]pyridine-6-carboxylic acid dihydrochloride (40 mg, 0.070 mmol) and 4-(2-aminoethyl)morpholine (400 μL, 3.0 mmol) was formed 7-(cyclopentylamino)-3-[2-(cyclopentylamino)-4-pyrimidinyl]-2-(4fluorophenyl)-N-[2-(4morpholinyl)ethyl]pyrazolo[1,5-a]pyridine-6-carboxamide (20 mg, 47%) as an orange solid. $R_f$ 0.27 (27:3 ethyl acetate:methanol); $^1$H NMR (400 MHz, CDCl$_3$): δ 8.53 (broad, 1H), 8.07 (d, 1H), 7.65–7.61 (m, 3H), 7.40 (d, 1H), 7.12 (t, 2H), 6.92 (broad, 1H), 6.32 (d, 1H), 5.11 (d, 1H), 5.00 (broad, 1H), 4.30 (m, 1H), 3.74 (t, 4H), 3.56 (m, 2H), 2.63 (t, 2H), 2.53 (broad, 4H), 2.09–1.95 (m, 4H), 1.81–1.49 (m, 12H); MS m/z 613 (M+1).

EXAMPLE 9

7-(Cyclopentylamino)-3-[2-(cyclopentylamino)-4-pyrimidinyl]-2-(4-fluorophenyl)-N-[3-(1H-imidazol-1-yl)propyl]pyrazolo[1,5-a]pyridine-6-carboxamide

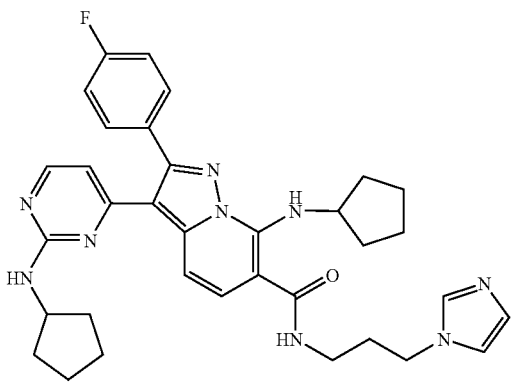

In a similar manner as described in Example 5 from 7-(cyclopentylamino)-3-[2-(cycloperitylamino]-4-pyrimidinyl]-2-(4-fluorophenyl)pyrazolo[1,5-a]pyridine-6-carboxylic acid dihydrochloride (40 mg, 0.070 mmol) and 1-(3-aminopropyl)imidazole (400 μL, 3.4 mmol) was formed 7-(cyclopentylamino)-3-[2-(cyclopentylamino)-4-pyrimidinyl]-2-(4-fluorophenyl)-N-[3-(1H-imidazol-1-yl)propyl]pyrazolo[1,5-a]pyridine-6-carboxamide (19 mg, 43%) as a yellow solid. $R_f$ 0.09 (27:3 ethyl acetate:methanol); $^1$H NMR (400 MHz, CDCl$_3$): δ 8.44 (d, 1H), 8.06 (d, 1H), 7.65–7.60 (m, 4H), 7.37 (d, 1H), 7.14–7.08 (m, 4H), 6.98 (s, 1H), 6.65 (t, 1H), 6.30 (d, 1H), 4.94 (m, 1H), 4.29 (m, 1H), 4.08 (t, 2H), 3.47 (m, 2H), 2.13 (m, 2H), 2.07–1.95 (m, 4H), 1.80–1.47 (m, 12H); MS m/z 608 (M+1).

EXAMPLE 10

7-(Cyclopentylamino)-3-[2-(cyclopentylamino)-4-pyrimidinyl]-2-(4-fluorophenyl)-N-[2-hydroxy-1-(hydroxymethyl)ethyl]pyrazolo[1,5-a]pyridine-6-carboxamide

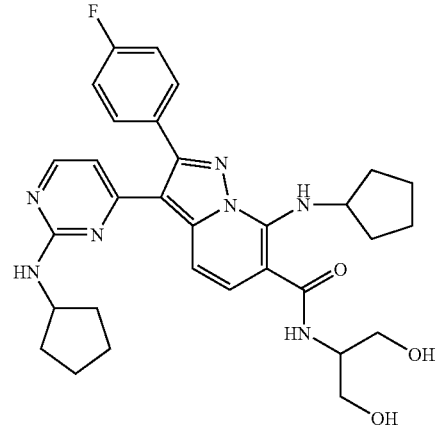

In a similar manner as described in Example 5 from 7-(cyclopentylamino)-3-[2-(cyclopentylamino)-4-pyrimidinyl]-2-(4-fluorophenyl)pyrazolo[1,5-a]pyridine-6-carboxylic acid dihydrochloride (40 mg, 0.070 mmol) and serinol (200 mg, 2.2 mmol) was formed 7-(cyclopentylamino)-3-[2-(cyclopentylamino)-4-pyrimidinyl]-2-(4-fluorophenyl)-N-[2-hydroxy-1-(hydroxymethyl)ethyl]pyrazolo[1,5-a]pyridine-6-carboxamide (8 mg, 20%) as an orange solid. $^1$H NMR (300 MHz, CDCl$_3$): δ 8.47 (broad, 1H), 7.97 (broad, 1H), 7.66–7.10 (m, 8H), 6.24 (d, 1H), 5.00 (broad, 1H), 4.32 (m, 1H), 4.17 (m, 1H). 3.98 (m, 4H), 2.12–1.94 (m, 4H), 1.83–1.54 (m, 12H); MS m/z 572 (M−1).

EXAMPLE 11

[7-(Cyclopentylamino)-3-[2-(cyclopentylamino)-4-pyrimidinyl]-2-(4-fluorophenyl)pyrazolo[1,5-a]pyridin-6-yl]methanol

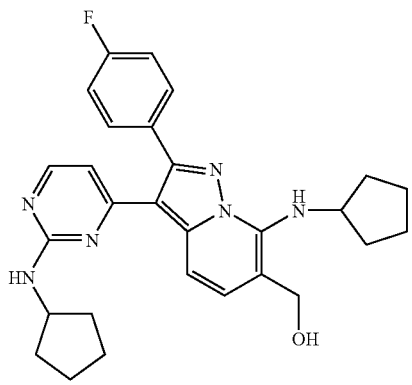

To a cold (−78° C.) solution of ethyl 7-(cyclopentylamino)-3-[2-(cyclopentylamino)-4-pyrimidinyl]-2-(4-fluorophenyl)pyrazolo[1,5-a]pyridine-6-carboxylate (50 mg, 0.095 mmol) in dichloromethane (1 mL) was added diisobutylaluminum hydride (490 μL, 1.0 M in hexanes, 0.49 mmol). The reaction mixture was stirred at −78° C. for 2 hours then poured into a stirring mixture of ether and aqueous Rochelle's salt (sodium potassium tartrate) solution. The resultant mixture was stirred at room temperature for 16 hours. The organic layer was separated and the aqueous layer was extracted with ethyl acetate. The combined organic layers were washed with water and brine. Concentration followed by flash chromatography on silica (29:1 dichloromethane:methanol) provided [7-(cyclopentylamino)-3-[2-(cyclopentylamino)-4-pyrimidinyl]-2-(4-fluorophenyl)pyrazolo-[1,5-a]pyridin-6-yl]methanol (27 mg, 59%) as a green solid. $R_f$ 0.26 (29:1 dichloromethane:methanol); $^1$H NMR (300 MHz, CDCl$_3$): δ 7.99 (d, 1H), 7.70 (d, 1H), 7.61 (m, 2H), 7.23 (d, 1H), 7.13 (t, 2H), 6.29–6.24 (m, 2H), 5.08 (d, 1H), 4.79 (s, 2H), 4.47 (broad, 1H), 4.29 (m, 1H). 2.09–1.99 (m, 4H), 1.85–1.48 (m, 12H); MS m/z 487 (M+1).

EXAMPLE 12

N-Cyclopentyl-4-[5,7-dichloro-2-(4-fluorophenyl)pyrazolo[1,5-a]pyridin-3-yl]-2-pyrimidinamine

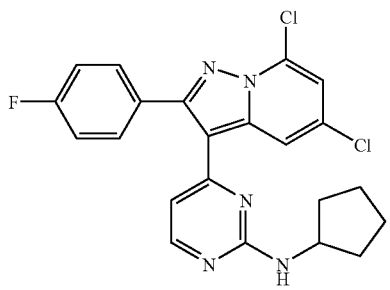

a) 2-(4-Chloro-2-pyridinyl)-1-(4-fluorophenyl)ethanone.

To a cold (0° C.) solution of 4-chloro-2-picoline (5.0 g, 39 mmol) and ethyl 4-fluorobenzoate (6.6 g, 39 mmol) in tetrahydrofuran (100 mL) was added lithium bis(trimethylsilyl)amide (80 mL, 1.0 M in tetrahydrofuran, 80 mmol) dropwise via a pressure equalizing funnel over 30 minutes. Upon complete addition, the cold bath was removed and the resulting solution was stirred at room temperature for 15 hours. The reaction mixture was concentrated under reduced pressure and methanol was added to the reaction, resulting in the formation of a white precipitate. The precipitate was collected by filtration and dried to give 2-(4-chloro-2-pyridinyl)-1-(4-fluorophenyl)ethanone (9.6 g, 99%) as a white solid. $^1$H NMR (DMSO-d$_6$): δ 7.90 (m, 3H), 7.11 (t, 2H), 6.56 (s, 1H), 5.67 (s, 1H), 4.14 (m, 2H); $^{19}$F NMR (DMSO-d$_6$): δ −115.67; MS m/z 250 (M+1).

b) 2-(4-Chloro-2-pyridinyl)-1-(4fluorophenyl)ethanone oxime.

To a solution of 2-(4-chloro-2-pyridinyl)-1-(4-fluorophenyl)ethanone (9.6 g, 38 mmol) in methanol (200 mL) was added hydroxylamine hydrochloride (13.5 g, 190 mmol) followed by the addition of a sodium hydroxide solution (7.8 g, 190 mmol in 50 mL of water). The resulting suspension was heated at reflux for 2 hours and then allowed to cool to room temperature. The mixture was concentrated and water was added to the resulting slurry. A white precipitate formed, which was collected by filtration, washed with water and dried (magnesium sulfate) to give 2-(4-chloro-2-pyridinyl)-1-(4-fluorophenyl)ethanone oxime (8.45 g, 84%) as a white solid. $^1$H NMR (DMSO-d$_6$): δ11.56 (s, 1H), 8.44 (d, 1H), 7.80 (m, 2H), 7.40 (m, 2H), 7.22 (m, 2H), 4.29 (s, 2H); $^{19}$F NMR (DMSO-d$_6$): δ −113.44; MS m/z 265 (M+1).

c) 5-Chloro-2-(4-fluorophenyl)pyrazolo[1,5-a]pyridine.

To a solution of 2-(4-chloro-2-pyridinyl)-1-(4-fluorophenyl)ethanone oxime (8.0 g, 30 mmol) in 1,2-dimethoxyethane (50 mL) at 0° C. was added trifluoroacetic anhydride (6.3 g, 30 mmol), keeping the temperature below 10° C. during the addition. After the addition was complete, the reaction was warmed to room temperature. The solution was then cooled to 4° C. and a solution of triethylamine (8.4 mL, 60 mmol) in 1,2-dimethoxyethane (20 mL) was added over a period of 0.5 hours. The mixture was allowed to warm to room temperature and was stirred for 1.5 hours. To this mixture was added iron(II) chloride (40 mg) and the reaction was heated at 75° C. for 15 hours. The reaction mixture was poured into water (300 mL). The resulting suspension was extracted with ethyl acetate. The combined organics were dried (magnesium sulfate), filtered and concentrated to a solid residue. This residue was purified by flash chromatography (1:1 ethyl acetate-hexane) to give 5-chloro-2-(4-fluorophenyl)pyrazolo[1,5-a]pyridine (4.2 g, 57%) as a white solid. $^1$H NMR (CDCl$_3$): δ 8.36 (d, 1H), 7.93 (q, 2H), 7.49 (d, 1H), 7.15 (t, 2H), 6.70 (dd, 1H), 6.69 (s, 1H). $^{19}$F NMR (CDCl$_3$): δ −113.30; MS m/z 247 (M+1).

d) 5-Chloro-2-(4-fluorophenyl)pyrazolo[1,5-a]pyridine-3-carbaldehyde.

Phosphorous oxychloride (0.6 mL, 6.4 mmol) was added to N,N-dimethylformamide (10 mL) and the resulting mixture stirred at room temperature for 10 minutes. 5-Chloro-2-(4-fluorophenyl)pyrazolo[1,5-a]pyridine (1.0 g, 4.1 mmol) was added and the reaction mixture was stirred at room temperature for 12 hours. The reaction mixture was poured into ice-water and neutralized to pH 7 with aqueous ammonium hydroxide. The resulting slurry was extracted with dichloromethane. The combined organics were washed with brine, dried (magnesium sulfate), filtered and concentrated to give, after recrystallization from acetonitrile, 5-chloro-2-(4-fluorophenyl)pyrazolo[1,5-a]pyridine-3-carbaldehyde (0.95 g, 85%) as a white solid. $^1$H NMR (CDCl$_3$): δ 10.07 (s, 1H), 8.49 (d, 1 H), 8.44 (d, 1H), 7.78 (q, 2H), 7.22 (t, 2H), 7.07 (dd, 1H). MS m/z 275 (M+1).

e) 1-[5-Chloro-2-(4-fluorophenyl)pyrazolo[1,5-a]pyridin-3-yl]-2-butyn-1-one.

To a solution of 5-chloro-2-(4-fluorophenyl)pyrazolo[1,5-a]pyridine-3-carbaldehyde (0.93 g, 3.4 mmol) in tetrahydrofuran (20 mL) at −78° C. was added ethynylmagnesium bromide (16 mL 0.5 M in tetrahydrofuran, 8.0 mmol). The mixture was allowed to warm to room temperature and stirred for 1 hour. Water was added to the reaction and the resulting mixture was extracted with ethyl acetate. The ethyl acetate phase was dried (magnesium sulfate), filtered and concentrated to a solid residue. This residue was dissolved in dichloromethane (50 mL) and manganese dioxide (5 g) was added. This slurry was stirred at room temperature for 2 hours. The manganese dioxide was removed by filtration and the filtrate was concentrated to a solid. This solid was purified by flash chromatography (dichloromethane) to give 1-[5-chloro-2-(4-fluorophenyl)pyrazolo[1,5-a]pyridin-3-yl]-2-butyn-1-one (0.63 g, 62% for two steps) as a white solid. $^1$H NMR (CDCl$_3$): δ 8.52 (d, 1H), 8.47 (d, 1H), 7.69 (q, 2H), 7.18 (t, 2H), 7.07 (dd, 1H), 3.00 (s, 1H). $^{19}$F NMR (CDCl$_3$): δ −111.69; MS m/z 299 (M+1).

f) 4-[5-Chloro-2-(4-fluorophenyl)pyrazolo[1,5-a]pyridin-3-yl]-N-cyclopentyl-2-pyrimidinamine.

To a solution of 1-[5-chloro-2-(4-fluorophenyl)pyrazolo[1,5-a]pyridin-3-yl]-2-butyn-1-one (0.61 g, 2.0 mmol) in N,N-dimethylformamide was added N-cyclopentyl guanidine hydrochloride (0.67 g, 4.1 mmol) followed by potassium carbonate (0.57 g, 4.1 mmol). The resulting mixture was heated at 80° C. for 12 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (1:1 ethyl acetate-hexane) to give, after recrystallization from acetonitrile, 4-[5-chloro-2-(4-fluorophenyl)pyrazolo[1,5-a]pyridin-3-yl]-N-cyclopentyl-2-pyrimidinamine (0.6 g, 74%) as a white solid. $^1$H NMR (CDCl$_3$): δ 8.54 (broad s, 1H), 8.40 (d, 1H), 8.04 (d, 1H), 7.60 (q, 2H), 7.16 (t, 2H), 6.88 (dd, 1H), 6.28 (d, 1H), 5.22 (d, 1H), 4.40 (m, 1H), 1.4–2.2 (m, 8H; $^{19}$F NMR (CDCl$_3$); δ −112.5; MS m/z 408 (M+1).

g) N-Cyclopentyl-4-[5,7-dichloro-2-(4-fluorophenyl)pyrazolo[1,5-a]pyridin-3-yl]-2-pyrimidinamine.

To a solution of 4-[5-chloro-2-(4-fluorophenyl)pyrazolo[1,5-a]pyridin-3-yl]-N-cyclopentyl-2-pyrimidinamine (100 mg, 0.25 mmol) in anhydrous tetrahydrofuran (5 mL) at −78° C. was added n-butyllithium (0.5 mL of 1.6 M solution in hexanes, 0.8 mmol). The resulting reaction mixture was stirred at −78° C. for 10 minutes, followed by addition of carbon tetrachloride (1 mL) and stirring at −78° C. for additional 20 minutes. The reaction was then quenched by the addition of water. The mixture was extracted with ethyl acetate. The ethyl acetate phase was washed with brine, dried (magnesium sulfate), filtered and concentrated in vocuo. The resulting residue was purified by flash chromatography (1:1 ethyl acetate-hexane) to give 50 mg (45%) of N-cyclopentyl-4-[5,7-dichloro-2-(4-fluorophenyl)pyrazolo[1,5-a]pyridin-3-yl]-2-pyrimidinamine as a yellow foam. $^1$H NMR (CDCl$_3$): δ 8.53 (broad s, 1H), 8.06 (d, 1H), 7.63 (m, 2H), 7.15 (t, 2H), 7.05 (d, 1H), 6.27 (d, 1H), 5.17 (d, 1H), 4.35 (m, 1H), 2.0–2.1 (m, 2H), 1.4–1.9 (m, 6H); $^{19}$F NMR (CDCl$_3$): δ 112.2; MS m/z 442 (M+1).

EXAMPLE 13

N-{4-[5-Chloro-7-(cyclopentylamino)-2-(4-fluorophenyl)pyrazolo[1,5-a]pyridin-3-yl]-2-pyrimidinyl}-N-cyclopentylamine

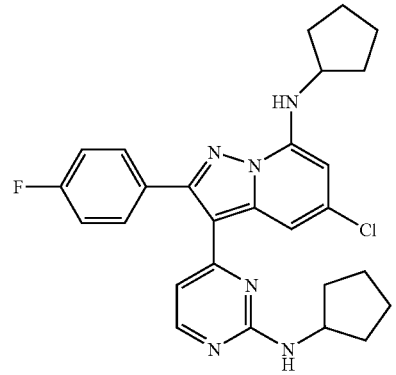

To a solution of N-cyclopentyl-4-[5,7-dichloro-2-(4-fluorophenyl)pyrazolo[1,5-a]pyridin-3-yl]-2-pyrimidinamine (0.04 g, 0.1 mmol) in cyclopentylamine (4 mL) was added racemic-2,2'-bis(diphenylphosphino)-1,1'-binaphthyl (25 mg), cesium carbonate (50 mg) and palladium (II) acetate (5 mg). The resulting mixture was stirred at 80° C. for 24 hours. Water was added and the mixture was extracted with ethyl acetate. The ethyl acetate phase was washed with brine, dried (magnesium sulfate), filtered and concentrated in vacuo. The resulting residue was purified by flash chromatography (3:7 ethyl acetate-hexane) to give 30 mg (68%) of N-{4-[5-chloro-7-(cyclopentylamino)-2-(4-fluorophenyl)pyrazolo[1,5-a]pyridin-3-yl]-2-pyrimidinyl}-N-cyclopentylamine as a yellow foam. $^1$H NMR (CDCl$_3$): δ 8.00 (d, 1H), 7.82 (s, 1H). 7.61 (m, 2H), 7.15 (t, 2H), 6.23 (d, 1H), 6.06 (d, 1H), 6.00 (s, 1H), 5.11 (d, 1H), 4.35 (m, 1H), 3.95 (m, 1H), 2.0–2.1 (m, 4H), 1.5–1.9 (m, 12H); $^{19}$F NMR (CDCl$_3$): δ 113.0; MS m/z 4.91 (M+1).

EXAMPLE 14

$N^5,N^7$-Dicyclopentyl-3-[2-(cyclopentylamino)-4-pyrimidinyl]-2-(4-fluorophenyl)pyrazolo[1,5-a]pyridine-5,7-diamine

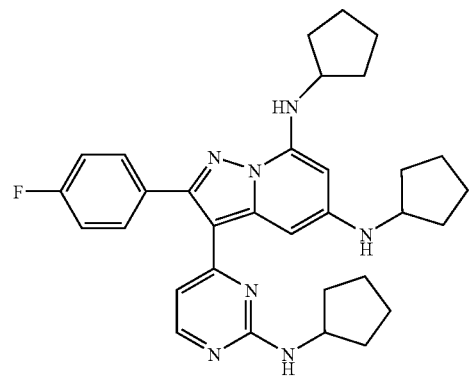

To a solution of N-cyclopentyl-4-[5,7-dichloro-2-(4-fluorophenyl)pyrazolo[1,5-a]pyridin-3-yl]-2-pyrimidinamine (0.09 g, 0.2 mmol) in cyclopentylamine (5 mL) was added racemic-2,2'-bis(diphenylphosphino)-1,1'-binaphthyl (100 mg), cesium carbonate (130 mg) and palladium (II) acetate (20 mg). The resulting mixture was heated in a sealed tube at 130° C. for 8 hours. Water was added and the mixture was extracted with ethyl acetate. The ethyl acetate phase was washed with brine, dried (magnesium sulfate), filtered and concentrated in vacuo. The resulting residue was purified by flash chromatography (1:1 ethyl acetate-hexane) to give 40 mg (37%) of $N^5,N^7$-dicyclopentyl-3-[2-(cyclopentylamino)-4-pyrimidinyl]-2-(4-fluorophenyl)pyrazolo[1,5-a]pyridine-5,7-diamine as a foam. $^1$H NMR (CDCl$_3$): δ 7.90 (d, 1H), 7.58 (m, 2H), 7.10 (t, 2H), 6.93 (d, 1H), 6.15 (d, 1H), 5.78 (d, 1h), 5.35 (d, 1h), 5.05 (m, 1H), 4.40 (m, 1H), 3.9–4.0 (m, 3H), 2.0–2.1 (m, 6H), 1.4–1.9 (m, 18H); $^{19}$F NMR (CDCl$_3$): δ –113.9; MS m/z 540 (M+1).

EXAMPLE 15

5-Chloro-3-[2-(cyclopentylamino)-4-pyrimidinyl]-2-(4-fluorophenyl)-N-isopropylpyrazolo[1,5-a]pyridin-7-amine

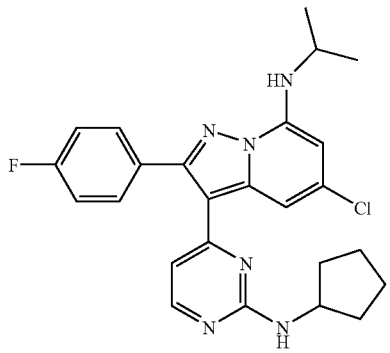

A solution of N-cyclopentyl-4-[5,7-dichloro-2-(4-fluorophenyt)pyrazolo[1,5-a]pyridin-3-yl]-2-pyrimidinamine (0.05 g, 0.11 mmol) in isopropylamine was treated as described for Example 13 to give, after flash chromatography (1:1 ethyl acetate-hexane), 30 mg (58%) of 5-chloro-3-[2-(cyclopentylamino)-4-pyrimidinyl]-2-(4-fluorophenyl)-N-isopropylpyrazolo[1,5-a]pyridin-7-amine as a foam. $^1$H NMR (CDCl$_3$): δ 8.02 (d, 1H), 7.88 (s, 1H), 7.64 (m, 2H), 7.20 (t, 2H), 6.27 (d, 1H), 6.04 (m, 2H), 5.30 (m, 1H), 4.39 (m, 1H), 3.84 (m, 1H), 2.0–2.1 (m, 2H), 1.4–1.9 (m, 6H), 1.42 (d, 6H); $^{19}$F NMR (CDCl$_3$): δ –112.8; MS m/z 465 (M+1).

EXAMPLE 16

3-[2-(Cyclopentylamino)-4-pyrimidinyl]-2-(4-fluorophenyl)-$N^5,N^7$-diisopropylpyrazolo[1,5-a]pyridine-5,7-diamine

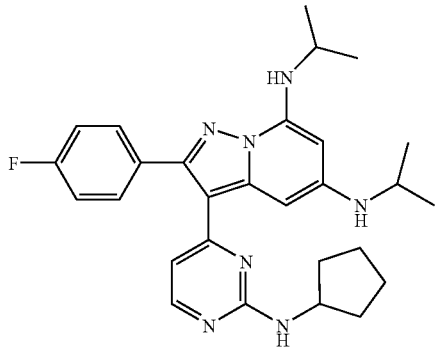

A solution of N-cyclopentyl-4-[5,7-dichloro-2-(4-fluorophenyl)pyrazolo[1,5-a]pyridin-3-yl]-2-pyrimidinamine (0.05 g, 0.11 mmol) in isopropylamine was treated as described for Example 14 to give, after flash chromatography (1:1 ethyl acetate-hexane), 20 mg (37%) of 3-[2-(cyclopentylamino)-4-pyrimidinyl]-2-(4-fluorophenyl)-$N^5$,$N^7$-diisopropylpyrazolo[1,5-a]pyridine-5,7-diamine as a foam. $^1$H NMR (CDCl$_3$): δ 7.90 (d, 1H), 7.62 (m, 2H), 7.16 (t, 2H), 6.98 (s, 1H), 6.19 (d, 1H), 5.75 (d, 1H), 5.37 (s, 1H), 5.20 (s, 1H), 4.45 (m, 1H), 3.80 (m, 3H), 2.2–2.0 (m, 2H), 1.4–1.9 (m, 6H), 1.38 (d, 6H), 1.33 (d, 6H); $^{19}$F NMR (CDCl3): δ –113.7; MS m/z 488 (M+1).

EXAMPLE 17

N-Cyclopentyl-4-[5,7-dichloro-2-(4-methoxyphenyl)pyrazolo[1,5-a]pyridin-3-yl]-2-pyrimidinamine

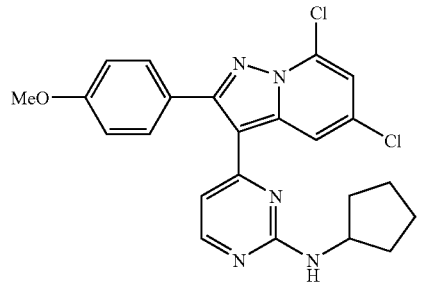

a) 2-(4-Chloro-2-pyridinyl)-1-(4-methoxyphenyl)ethanone.
2-(4-Chloro-2-pyridinyl)-1-(4-methoxyphenyl)ethanone was synthesized from 4-chloro-2-picoline (10 g, 78.4 mmol) and ethyl 4-methoxybenzoate (14.1 g, 78.4 mmol) as described in Example 12 to give the product as a mixture of enol and keto tautomers. MS m/z 262 (M+1).

b) 2-(4-Chloro-2-pyridinyl)-1-(4-methoxyphenyl)ethanone oxime.
2-(4-Chloro-2-pyridinyl)-1-(4-methoxyphenyl)ethanone in methanol (200 mL) was treated with hydroxylamine hydrochloride (27.2 g, 392 mmol) and a sodium hydroxide solution (15.7 g, 392 mmol in 50 mL of water) as described in Example 12 to give 2-(4-chloro-2-pyridinyl)-1-(4-methoxyphenyl)ethanone oxime (11.8 g) as a white solid. $^1$H NMR (CDCl$_3$): δ 8.47 (d, 1H), 7.72 (d, 2H), 7.36 (d, 1H), 7.19 (dd, 1H), 6.91 (d, 2H), 4.43 (s, 2H), 3.84 (s, 3H); MS m/z 277 (M+1).

c) 5-Chloro-2-(4-methoxyphenyl)pyrazolo[1,5-a]pyridine.
5-Chloro-2-(4-methoxyphenyl)pyrazolo[1,5-a]pyridine was synthesized from 2-(4-Chloro-2-pyridinyl)-1-(4methoxyphenyl)ethanone oxime (11.8 g, 42.6 mmol) as described in Example 12 to give 6.64 g (60%) of white needles. $^1$H NMR (CDCl$_3$): δ 8.35 (d, 1H), 7.86 (d, 2H), 7.46 (d, 1H), 6.97 (d, 2H), 6.67 (d, 1H), 6.65 (s, 1H), 3.85 (s, 3H); MS m/z 259 (M+1).

d) 5-Chloro-2-(4-methoxyphenyl)pyrazolo[1,5-a]pyridine-3-carbaldehyde.
5-Chloro-2-(4-methoxyphenyl)pyrazolo[1,5-a]pyridine (1.0 g, 3.86 mmol) was treated with N,N-dimethylformamide (20 mL) and phosphorous oxychloride (0.54 mL, 7.8 mmol) as described in Example 12 to give 5-chloro-2-(4-methoxyphenyl)pyrazolo[1,5-a]pyridine-3-carbaldehyde as a white crystalline solid, (0.9 g, 81%). $^1$H NMR (CDCl$_3$): δ 10.12 (s, 1H), 8.52 (d, 1H), 8.47 (d, 1H), 7.76 (d, 2H), 7.11–7.06 (m, 3H), 3.93(s, 3h); MS m/z 287 (M+1).

e) 1-[5-Chloro-2-(4-methoxyphenyl)pyrazolo[1,5-a]pyridin-3-yl]-2-propyn-1-ol.

5-Chloro-2-(4-methoxyphenyl)pyrazolo[1,5-a]pyridine-3-carbaldehyde (0.90 g, 3.14 mmol) in tetrahydrofuran (50 mL) was treated with ethynylmagnesium bromide (7.5 mL, 0.5 M in tetrahydrofuran, 3.77 mmol) as described in Example 12 to give 1-[5-chloro-2-(4-methoxyphenyl)pyrazolo[1,5-a]pyridin-3-yl]-2-propyn-1-ol (1.05 g, 100%) as a white solid. $^1$H NMR (CDCl$_3$) δ 8.40 (d, 1H), 8.05 (s, 1H), 7.72 (d, 2H), 7.05 (d, 2H), 6.80 (dd, 1H), 5.78 (s, 1H), 3.91 (s, 3H), 2.74 (s, 1H), 2.53 (s, 1H); MS m/z 313 (M+1).

f) 1-[5-Chloro-2-(4-methoxyphenyl)pyrazolo[1,5-a]pyridin-3-yl]-2-propyn-1-one.

1-[5-Chloro-2-(4-methoxyphenyl)pyrazolo[1,5-a]pyridin-3-yl]-2-propyn-1-ol (1.05 g, 3.14 mmol) in chloroform (100 mL) was treated with manganese dioxide (6.82 g, 78.5 mmol) as described in Example 12 to give 1-[5-chloro-2-(4-methoxyphenyl)pyrazolo[1,5-a]pyridin-3-yl]-2-propyn-1-one (0.99 g, 100%) as a pale yellow solid. $^1$H NMR (CDCl$_3$) δ 8.50 (d, 1H), 8.46 (d, 1H), 7.64 (d, 2H), 7.04 (dd, 1H), 6.98 (d, 2H), 3.87 (s, 3H), 2.99 (s, 1H); MS m/z 295 (M+1).

g) 4-[5-Chloro-2-(4-methoxyphenyl)pyrazolo[1,5-a]pyridin-3-yl]-N-cyclopentyl-2-pyrimidinamine.

Sodium ethoxide (0.7 mL (2.09 mmol), 21% in ethanol) and N-cyclopentyl guanidine hydrochloride (0.47 g, 2.88 mmol) were added sequentially to ethanol (30 mL). The resulting solution was stirred at room temperature for 30 minutes. 1-[5-chloro-2-(4-methoxyphenyl)pyrazolo[1,5-a]pyridin-3-yl]-2-propyn-1-one (0.5 g, 1.61 mmol) was added, and the suspension was stirred at room temperature for 2 days. The reaction was quenched by the addition of water. The aqueous phase was extracted by ethyl acetate. The organics were combined, washed with brine and dried over magnesium sulfate. Filtration and concentration gave a solid. This solid was recrystallized from methanol to give 4-[5-chloro-2-(4-methoxyphenyl)pyrazolo[1,5-a]pyridin-3-yl]-N-cyclopentyl-2-pyrimidinamine (0.45 g, 66%) as a pale yellow solid. $^1$H NMR (CDCl3): δ 8.59 (broad s, 1H), 8.42 (d, 1H), 8.05 (d, 1H), 7.59 (d, 2H), 7.03 (d, 2H), 6.91 (dd, 1H), 6.39 (d, 1H), 5.34 (broad s, 1H), 4.42 (m, 1H), 3.92 (s, 3H), 2.17 (m, 2H), 1.86–1.60 (m, 6H); MS m/z 420 (M+1).

h) N-Cyclopentyl-4-[5,7-dichloro-2-(4-methoxyphenyl)pyrazolo[1,5-a]pyridin-3-yl]-2-pyrimidinamine.

4-[5-Chloro-2-(4-methoxyphenyl)pyrazolo[1,5-a]pyridin-3-yl]-N-cyclopentyl-2-pyrimidinamine (0.2 g, 0.48 mmol) was treated with n-butyllithium (0.9 mL of 1.6 M solution in hexane, 1.43 mmol), followed by quenching with carbon tetrachloride (1 mL) as described for Example 12 to give 94 mg (43%) of N-cyclopentyl-4-[5,7-dichloro-2-(4-methoxyphenyl)pyrazolo[1,5-a]pyridin-3-yl]-2-pyrimidinamine as a yellow solid. $^1$H NMR (CDCl$_3$): δ 8.57 (broad s, 1H), 7.98 (s, 1H), 7.55 (d, 2H), 7.05 (s, 1H), 6.98 (d, 2H), 6.35 (d, 1H), 5.60 (broad s, 1H), 4.35 (m, 1H), 3.87 (s, 3H), 2.2–2.0 (m, 2H), 1.4–1.9 (m, 6H); MS m/z 454 (M+1).

EXAMPLE 18

N-{4-[5-Chloro-7-(cyclopentylamino)-2-(4-methoxyphenyl)pyrazolo-[1,5-a]pyridin-3-yl]-2-pyrimidinyl}-N-cyclopentylamine

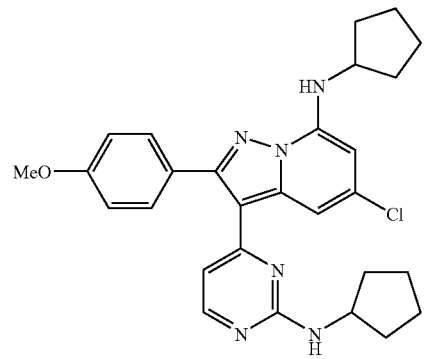

N-{4-[5-Chloro-7-(cyclopentylamino)-2-(4-methoxyphenyl)pyrazolo[1,5-a]pyridin-3-yl]-2-pyrimidinyl}-N-cyclopentylamine. N-Cyclopentyl-4-[5,7-dichloro-2-(4-methoxyphenyl)pyrazolo[1,5-a]pyridin-3-yl]-2-pyrimidinamine (80 mg, 0.18 mmol) in cyclopentylamine was treated as described for Example 13 to give 70 mg (80%) of N-{4-[5-chloro-7-(cyclopentylamino)-2-(4-methoxyphenyl)pyrazolo[1,5-a]pyridin-3-yl]-2-pyrimidinyl}-N-cyclopentylamine as a solid. $^1$H NMR (CDCl$_3$): δ 7.96 (d, 1H), 7.85 (s, 1H), 7.54 (d, 2H), 6.98 (d, 2H), 6.27 (d, 1H), 6.08 (d, 1H), 5.97 (d, 1H), 5.13 (d, 1h), 4.35 (m, 1H), 3.95 (m, 1H), 3.87 (s, 3H), 2.2–2.0 (m, 4H), 1.4–1.9 (m, 12H); MS m/z 503 (M+1).

EXAMPLE 19

5-Chloro-N-cyclopentyl-3-[2-(cyclopentylamino)pyrimidin-4-yl]-2-(3-methylphenyl)pyrazolo[1,5-a]pyridin-7-amine

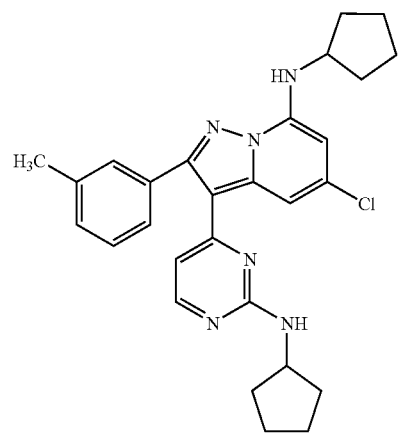

The title compound was prepared in a similar manner as previous examples to give a yellow solid. $^1$H NMR (CDCl$_3$): δ 7.94 (d, 1H), 7.89 (s, 1H), 7.43–7.25 (m, 4H), 6.23 (d, 1H), 6.09 (d, 1H), 6.00 (s, 1H), 5.12 (d, 1H), 4.36 (m, 1H), 3.95 (m, 1H), 2.40 (s, 3H), 2.10 (m, 4H), 1.80–1.53 (m, 12H); MS m/z 487 (M+1).

EXAMPLE 20

5-Chloro-3-[2-(cyclopentylamino)pyrimidin-4-yl]-N-cyclopropyl-2-(3-methylphenyl)pyrazolo[1,5-a]pyridin-7-amine

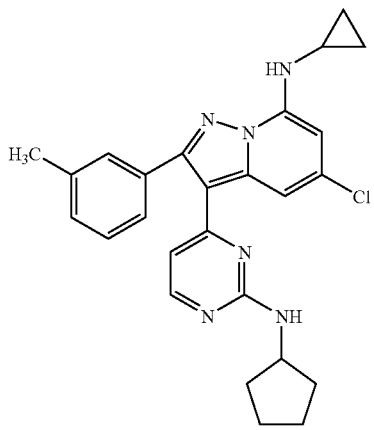

The title compound was prepared in a similar manner as previous examples to give a yellow solid. $^1$H NMR (CDCl$_3$): δ 7.96 (d, 2H), 7.41–7.24 (m, 4H), 6.36 (d, 1H), 6.23 (d, 1H), 5.12 (d, 1H), 4.36 (m, 1H), 2.65 (br, 1H), 2.39 (s, 3H), 2.12 (m, 2H), 1.79–1.53 (m, 6H), 1.25 (s, 1H), 0.92–0.87 (m, 2H), 0.76–0.72 (m, 2H); MS m/z 459 (M+1).

EXAMPLE 21

5-Chloro-N-cyclopentyl-3-[2-(cyclopropylamino)pyrimidin-4-yl]-2-(3-methylphenyl)pyrazolo[1,5-a]pyridin-7-amine

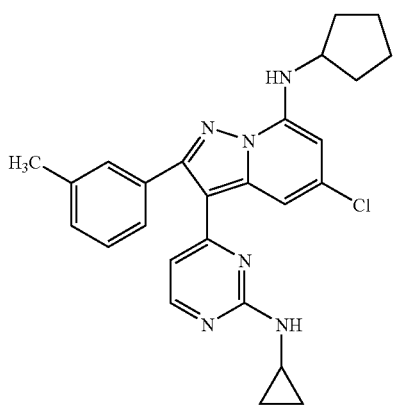

The title compound was prepared in a similar manner as previous examples to give a yellow solid. $^1$H NMR (CDCl$_3$): δ 8.16 (s, 1H), 7.92 (d, 1H), 7.43–7.28 (m, 4H), 6.30 (d, 1H), 6.10 (d, 1H), 6.04 (s, 1H), 3.99–3.94 (m, 1H), 2.88 (br, 1H), 2.42 (s, 3H), 2.17–2.13 (m, 3H), 1.81–1.56 (m, 6H), 0.97–0.92 (m, 2H), 0.71–0.67 (m, 2H); MS m/z 459 (M+1).

EXAMPLE 22

5-Chloro-3-[2-(cyclopentylamino)-4-pyrimidinyl]-N-cyclopropyl-2-(4-fluorophenyl)pyrazolo[1,5-a]pyridin-7-amine

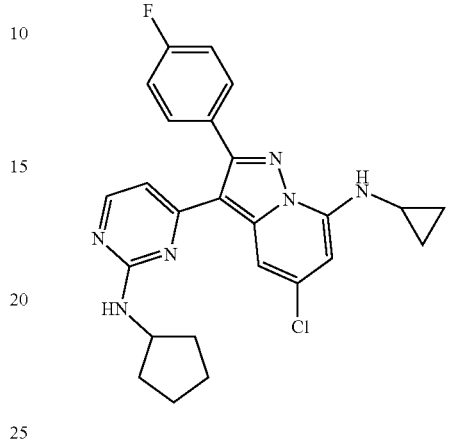

The title compound was prepared in a similar manner as previous examples to give a yellow solid. R$_f$ 0.54 (98:2 dichloromethane:methanol); $^1$H NMR (CDCl$_3$): δ 8.00 (d, 1H), 7.89 (s, 1H), 7.59 (dt, 2H), 7.14 (t, 2H), 6.36 (d, 1H), 6.35 (s, 1H), 6.23 (d, 1H), 5.13 (br, 1H), 4.34 (sextuplet, 1H), 2.71–2.68 (m, 1H), 2.20–2.10 (m, 2H), 1.85–1.55 (m, 6H), 0.98–0.95 (m, 2H), 0.90–0.85 (m, 2H); MS m/z 463 (M+1). Anal. Calcd for C$_{25}$H$_{24}$ClFN$_6$: C, 64.86; H, 5.23; N, 18.15. Found: C, 64.85; H, 5.26; N, 18.20.

EXAMPLE 23

4-[5-Chloro-2-(4-fluorophenyl)-7-(4-methyl-1-piperazinyl)pyrazolo[1,5-a]pyridin-3-yl]-N-cyclopentyl-2-pyrimidinamine

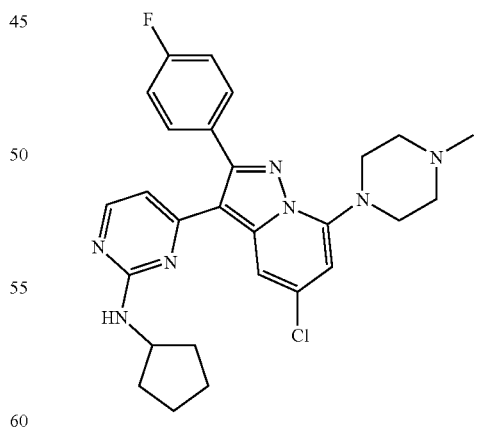

The title compound was prepared in a similar manner as previous examples to give a yellow solid foam. R$_f$ 0.12 (98:2 dichloromethane:methanol); $^1$H NMR (CDCl$_3$): δ 8.16 (s, 1H), 8.03 (d, 1H), 7.64 (dt, 2H), 7.12 (t, 2H), 6.28 (d, 1H), 6.26 (s, 1H), 5.10 (d, 1H), 4.35 (sextuplet, 1H), 3.6 (br, 4H), 2.70 (br, 4H), 2.40 (s, 3H), 2.18–2.08 (m, 2H), 1.80–150 (m, 6H); MS m/z 507 (M+1). Anal. Calcd for $C_{27}H_{29}ClFN_7 \cdot 0.25 H2O$: C, 63.52; H, 5.82; N, 19.21. Found: C, 63.37; H, 5.79; N, 19.12.

EXAMPLE 24

4-[5-Chloro-2-(4-fluorophenyl)-7-(1-piperidinyl)pyrazolo[1,5-a]pyridin-3-yl]-N-cyclopentyl-2-pyrimidinamine

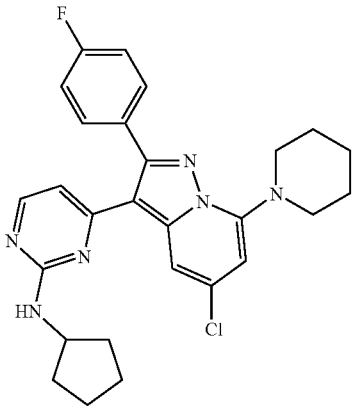

The title compound was prepared in a similar manner as previous examples to give a yellow solid foam. $R_f$ 0.55 (98:2 dichloromethane:methanol); $^1$H NMR (CDCl$_3$): δ 8.13 (br, 1H), 8.03 (d, 1H), 7.64 (dt, 2H), 7.11 (t, 2H), 6.28 (d, $_1$H), 6.26 (d, 1H), 5.20 (d, 1H), 4.36 (sextuplet, 1H), 3.42 (br, 4H), 2.20–2.15 (m, 2H), 1.90–1.50 (m, 12H); MS m/z 492 (M+1). Anal. Calcd for $C_{27}H_{28}ClFN_6 \cdot 0.15 H2O$: C, 65.68; H, 5.78; N, 17.02. Found: C, 65.25; H, 6.09; N. 17.42.

EXAMPLE 25

4-[5-Chloro-2-(4-fluorophenyl)-7-(4-morpholinyl)pyrazolo[1,5-a]pyridin-3-yl]-N-cyclopentyl-2-pyrimidinamine

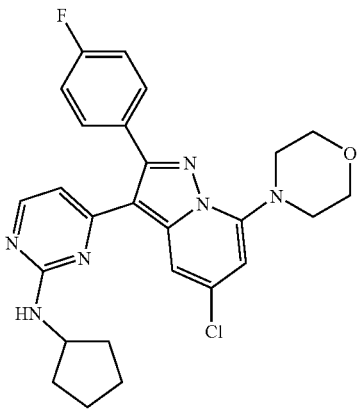

The title compound was prepared in a similar manner as previous examples to give a yellow solid. $R_f$ 0.32 (98:2 dichloromethane:methanol); $^1$H NMR (CDCl$_3$): δ 8.20 (br, 1H), 8.03 (s, 1H), 7.62 (dt, 2H), 7.13 (t, 2H), 6.28 (s, 1H), 6.26 (d, 1H), 5.36 (br, 1H), 4.37 (sextuplet, 1H), 3.99 (br, 4H), 3.58 (br, 4H), 2.18–2.08 (m, 2H), 1.80–1.50 (m, 6H); MS m/z 493 (M+1). Anal. Calcd for $C_{26}H_{26}ClFN_6O \cdot 0.5 H_2O$: C, 62.21; H, 5.42; N, 16.74. Found: C, 62.40; H, 5.35; N, 16.84.

EXAMPLE 26

N-[5-Chloro-3-[2-(cyclopentylamino)pyrimidin-4-yl]-2-(4-fluorophenyl)pyrazolo[1,5-a]pyridin-7-yl]-N'-cyclopentylguanidine hydrochloride

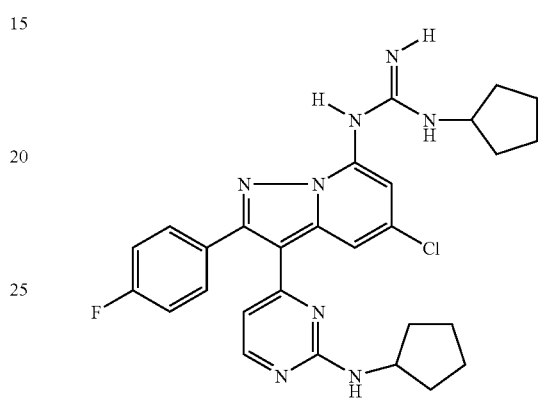

The title compound was prepared in a similar manner as previous examples. $^1$H NMR (MeOH-d$_4$): δ 8.67 (br, 1H), 7.93 (d, 1H), 7.66 (dd, 2H), 7.29 (t, 2H), 7.22 (s, 1H), 6.46 (d, 1H), 4.40–4.15 (br, $_1$H), 4.08–3.98 (br, 1H), 2.18–2.02 (m, 4H), 1.92–1.56 (m, 12H); MS m/z 533 (m+1); $C_{28}H_{30}N_8ClF \cdot HCl$.

EXAMPLE 27

5-Chloro-N-cyclopropyl-3-[2-(cyclopropylamino)pyrimidin-4-yl]-2-(4-fluorophenyl)pyrazolo[1,5-a]pyridin-7-amine

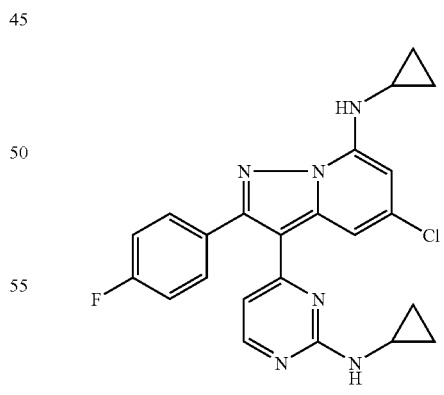

The title compound was prepared in a similar manner as previous examples to give a light yellow solid. $R_f$ 0.45 (8:2; hexane:ethyl acetate); $^1$H NMR (CDCl$_3$): δ 8.12 (br s, 1H), 8.02 (d, $_1$H), 7.58 (dd, 2H), 7.14 (t, 2H), 6.36 (d, 1H), 6.34 (s, 1H), 6.27 (d, 1H), 5.36 (s, 1H), 2.87–2.83 (m, 1H), 2.66–2.63 (m, 1H), 0.96–0.88 (m, 4H), 0.77–0.73 (m, 2H), 0.66–0.63 (m, 2H); MS m/z 435 (M+1); $C_{23}H_{20}N_6ClF$.

EXAMPLE 28

N-cyclopentyl-4-[5,7-dichloro-2-(3-chlorophenyl)pyrazolo[1,5-a]pyridin-3-yl]-2-pyrimidinamine

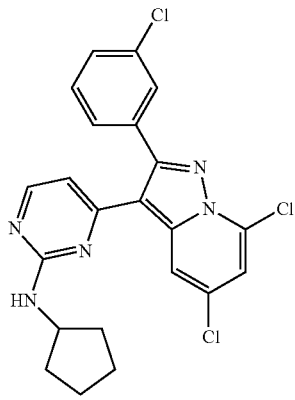

The title compound was prepared in a similar manner as previous examples to give a tan solid. $R_f$ 0.32 (4:1 hexanes; ethyl acetate); $^1$H NMR (CDCl$_3$): δ 8.55 (s, 1H), 8.10 (d, 1H), 7.69 (s, 1H), 7.54–7.37 (m, 3H), 7.05 (s, 1H), 6.31 (d,$_1$H), 5.20 (d, 1H), 4.38 (m, 1H), 2.14 (m, 2H), 1.85–1.55 (m, 6H); MS m/z 458 (M+1).

EXAMPLE 29

N-{4-[5-chloro-2-(3-chlorophenyl)-7-(cyclopentylamino)pyrazolo[1,5-a]pyridin-3-yl]-2-pyrimidinyl}-N-cyclopentylamine

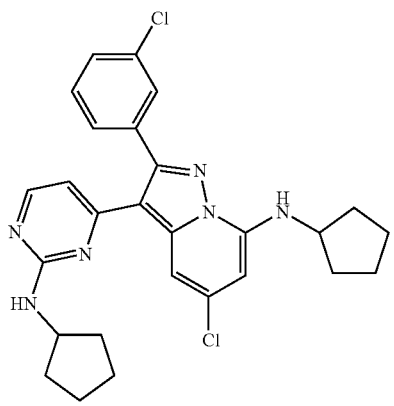

The title compound was prepared in a similar manner as previous examples to give a yellow solid. $R_f$ 0.25 (4:1 hexanes;ethyl acetate); $^1$H NMR (CDCl$_3$): δ 8.04 (d, 1H), 7.82 (s, 1H), 7.71 (s, 1H), 7.54–7.35 (m, 3H), 6.30 (d, 1H), 6.09 (d, 1H), 6.01 (s, 1H), 5.19 (d, 1H), 4.38 (m, 1H), 3.98 (m, 1H), 2.24–2.04 (m, 4H), 1.97–1.46 (m, 12H); MS m/z 507 (M+1).

EXAMPLE 30

N-{4-[5-Chloro-7-(cyclopropylamino)-2-(4-methoxyphenyl)pyrazolo[1,5-a]pyridin-3-yl]-2-pyrimidinyl}-N-cyclopentylamine

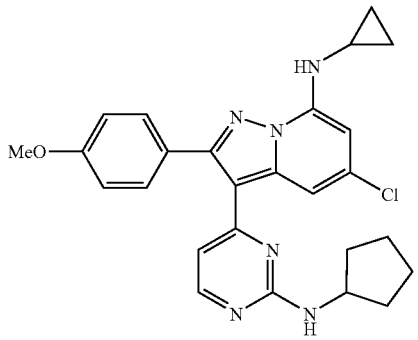

N-Cyclopentyl-4-[5,7-dichloro-2-(4-methoxyphenyl)pyrazolo[1,5-a]pyridin-3-yl]-2-pyrimidinamine (271 mg, 0.60 mmol) in cyclopropylamine (5 mL) was heated at 100° C. for 11 hours in a steel bomb. Cooled to room temperature. Ethyl acetate was added to the reaction mixture. The solution was washed with water and brine, then dried over magnesium sulfate. Filtration and concentration followed by purification with flash chromatography (4:1 hexanes/ethyl acetate) gave N-{4-[5-chloro-7-(cyclopropylamino)-2-(4-methoxyphenyl)pyrazolo[1,5-a]pyridin-3-yl]-2-pyrimidinyl}-N-cyclopentylamine (201 mg, yield 71%) as a yellow foam. $^1$H NMR (CDCl$_3$) δ 8.02 (d, 1H), 7.96 (s, 1H), 7.56 (d, 2H), 7.01 (d, 2H), 6.42 (s, 1H), 6.37 (d, 1H), 6.32 (d, 1H), 5.12 (d, 1H), 4.15 (m, 1H), 3.91 (s, 3H), 2.70 (m, 1H), 2.08 (m, 2H), 1.82–1.59 (m, 6H), 0.95 (m, 2H), 0.80 (m, 2H); MS m/z 475 (M+1).

EXAMPLE 31

4-[5-Chloro-3-[2-(cyclopentylamino)-4-pyrimidinyl]-7-(cyclopropylamino)pyrazolo[1,5-a]pyridin-2-yl]phenol

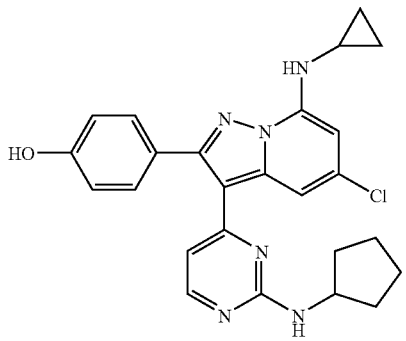

In a similar manner as described above, from N-{4-[5-chloro-7-(cyclopropylamino)-2-(4-methoxyphenyl)pyrazolo[1,5-a]pyridin-3-yl]-2-pyrimidinyl}-N-cyclopentylamine (153 mg, 0.32 mmol) was obtained the title compound (130 mg, 88%) as a yellow solid. $^1$H NMR (CD$_3$OD) δ 8.14 (s, 1H), 7.77 (d, 1H), 7.48 (d, 2H), 6.97 (d, 2H), 6.67 (s, 1H), 6.54 (d, 1H), 4.15 (m, 1H), 2.73 (m, 1H), 2.20 (m, 2H), 1.88–1.78 (m, 6H), 0.98 (m, 2H), 0.77 (m, 2H). MS m/z 461 (M+1).

EXAMPLE 32

5-Chloro-3-[2-(cyclopentylamino)-4-pyrimidinyl]-N-cyclopropyl-2-[4-(cyclopropylmethoxy)phenyl]pyrazolo[1,5-a]pyridin-7-amine

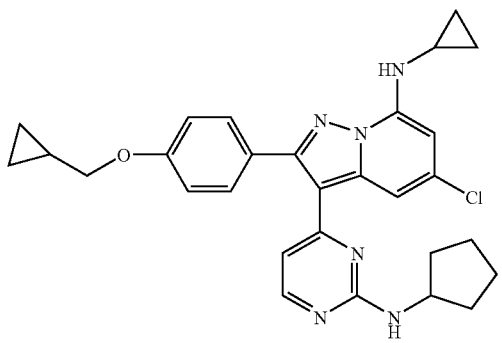

To a solution of 4-[5-chloro-3-[2-(cyclopentylamino)-4-pyrimidinyl]-7-(cyclopropylamino)pyrazolo[1,5-a]pyridin-2-yl]phenol (110 mg, 0.24 mmol) in acetonitrile was added bromomethyl cyclopropane (96 mg, 0.72 mmol) and cesium carbonate (85 mg, 0.26 mmol). The reaction mixture was heated at reflux for 6 hours. After cooling to room temperature, ethyl acetate was added to the reaction mixture. The organic phase was washed with water and brine, then dried over magnesium sulfate. Filtration and concentration, followed by flash chromatography (2:5 hexanes/ethyl acetate), gave 5-chloro-3-[2-(cyclopentylamino)-4-pyrimidinyl]-N-cyclopropyl-2-[4-(cyclopropylmethoxy)phenyl]pyrazolo[1,5-a]pyridin-7-amine (75 mg, 61%) as a yellow solid. $^1$H NMR (CDCl$_3$) δ 7.97 (d, 1H), 7.90 (s, 1H), 7.50 (d, 2H), 6.95 (d, 2H), 6.38 (s, 1H), 6.32 (d, 1H), 6.28 (d, 1H), 5.13 (d, 1H), 4.36 (m, 1H), 3.85 (d, 2H), 2.64 (m, 1H), 2.10 (m, 2H), 1.80–1.66 (m, 4H), 1.55 (m, 2H), 1.30 (m, 1H), 0.88 (m, 2H), 0.74 (m, 2H), 0.66 (m, 2H), 0.39 (m, 2H). MS m/z 515 (M+1).

EXAMPLE 33

4-[5-Chloro-3-[2-(cyclopentylamino)-4-pyrimidinyl]-7-(cyclopentylamino)pyrazolo[1,5-a]pyridin-2-yl]phenol

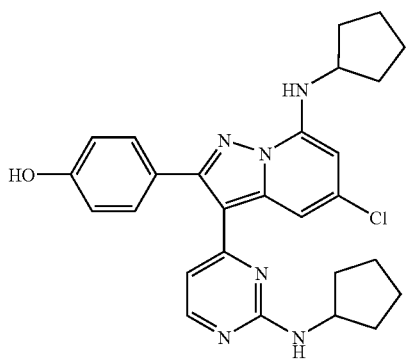

In a similar manner as described above, from N-{4-[5-chloro-7-(cyclopentylamino)-2-(4-methoxyphenyl)pyrazolo[1,5-a]pyridin-3-yl]-2-pyrimidinyl}-N-cyclopentylamine (160 mg, 0.32 mmol) was obtained the title compound (151 mg, 75%) as a yellow solid. $^1$H NMR (CD$_3$OD) δ 7.94–7.91 (m, 2H), 7.44 (d, 2H), 6.93 (d, 2H), 6.33 (d, 1H), 6.18 (d, 1H), 4.35 (m, 1H), 4.08 (m, 1H), 2.16 (m, 2H), 1.87–1.59 (m, 12H). MS m/z 489 (M+1).

EXAMPLE 34

5-Chloro-3-[2-(cyclopentylamino)-4-pyrimidinyl]-N-cyclopentyl-2-[4-(cyclopropylmethoxy)phenyl]pyrazolo[1,5-a]pyridin-7-amine

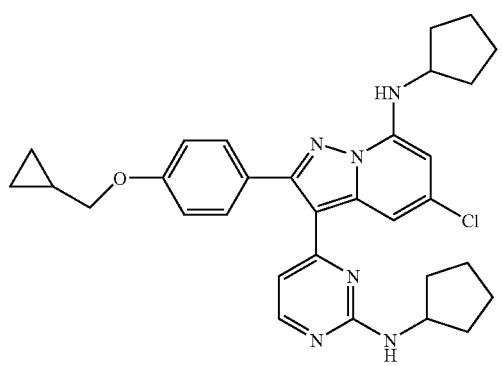

In a similar manner as described above, from 4-[5-chloro-3-[2-(cyclopentylamino)-4-pyrimidinyl]-7-(cyclopentylamino)pyrazolo[1,5-a]pyridin-2-yl]phenol (100 mg, 0.2 mmol) was obtained 5-chloro-3-[2-(cyclopentylamino)-4-pyrimidinyl]-N-cyclopentyl-2-[4-(cyclopropylmethoxy)phenyl]pyrazolo[1,5-a]pyridin-7-amine (87 mg, 78%) as a pale yellow solid. $^1$H NMR (CDCl$_3$) δ 7.96 (d, 1H), 7.85 (s, 1H), 7.53 (d, 2H), 6.97 (d, 2H), 6.27 (d, 1H), 6.08 (d, 1H), 5.98 (d, 1H), 5.08 (d, 1H), 4.35 (m, 1H), 3.96 (m, 1H), 3.86 (d, 2H), 2.13 (m, 4H), 1.80–1.53 (m, 12H), 1.31 (m, 1H), 0.68 (m, 2H), 0.38 (m, 2H). MS m/z 543 (M+1).

EXAMPLE 35

5,7-dichloro-2-(4-methoxyphenyl)-3-[2-(methylthio)pyrimidin-4-yl]pyrazolo[1,5-a]pyridine

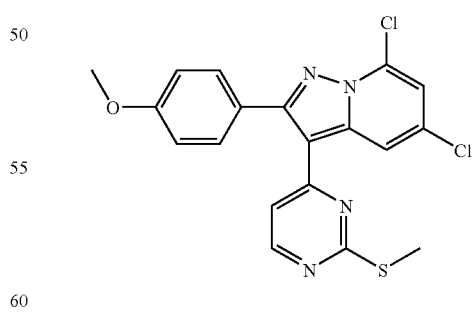

a) 4-{5-Chloro-3-[2-(methylsulfanyl)-4-pyrimidinyl]pyrazolo[1,5-a]pyridin-2-yl}phenyl methyl ether.

The suspension of 2-methyl-2-thiopseudourea (358 mg, 1.29 mmol) and potassium carbonate (178 mg, 1.29 mmol) in ethanol was stirred at room temperature for 10 minutes. 1-[5-Chloro-2-(4-methoxyphenyl)pyrazolo[1,5-a]pyridin-3- yl]-2-propyn-1-one (200 mg, 0.64 mmol) was added. The suspension was stirred at room temperature for 12 hours. Ethyl acetate was added. The ethyl acetate phase was washed with water and brine and dried over magnesium sulfate. Filtration and concentration, followed by chromatography (3:2 hexanes/ethyl acetate), gave 4-{5-chloro-3-[2-(methylsulfanyl)-4-pyrimidinyl]pyrazolo[1,5-a]pyridin-2-yl}phenyl methyl ether (77 mg, 31%) as a white solid. $^1$H NMR (CDCl$_3$) δ 8.49 (d, $_1$H), 8.37 (d, $_1$H), 8.20 (d, 1H), 7.48 (d, 2H), 6.98 (d, 2H), 6.85 (dd, 1H), 6.70 (d, 1H), 3.85 (s, 3H), 2.62 (s, 3H). MS m/z 383 (M+1).

b) 5,7-Dichloro-2-(4-methoxyphenyl)-3-[2-(methylthio)pyrimidin-4-yl]pyrazolo[1,5-a]pyridine.

In a similar manner as described above, from 4-{5-chloro-3-[2-(methylsulfanyl)-4-pyrimidinyl]pyrazolo[1,5-a]pyridin-2-yl}phenyl methyl ether (67 mg, 0.17 mmol) was obtained 5,7-Dichloro-2-(4-methoxyphenyl)-3-[2-(methylthio)pyrimidin-4-yl]pyrazolo[1,5-a]pyridine. (37 mg, 51%) as a yellow solid. $^1$H NMR (CDCl$_3$) δ 8.56 (d, 1H), 8.29 (d, 1H), 7.58 (d, 2H), 7.11 (d, 1H), 7.03 (d, 2H), 6.77 (d, 1H), 3.92 (s, 3H), 2.69 (s, 3H). MS m/z 417 (M+1).

EXAMPLE 36

N-{5-Chloro-2-(4-methoxyphenyl)-3-[2-(methylsulfanyl)-4-pyrimidinyl]pyrazolo[1,5-a]pyridin-7-yl}-N-cyclopentylamine

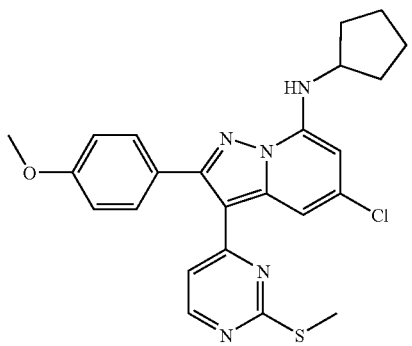

A solution of 5,7-dichloro-2-(4-methoxyphenyl)-3-[2-(methylsulfanyl)-4-pyrimidinyl]pyrazolo[1,5-a]pyridine (148 mg, 0.35 mmol) in cyclopentylamine (5 mL) was heated at 80° C. for 3 hours. After cooling to room temperature, ethyl acetate was added to the reaction mixture. The organic phase was washed with water and brine, then dried over magnesium sulfate. Filtration and concentration followed by chromatography (4:1 hexanes/ethyl acetate) gave N-{5-chloro-2-(4-methoxyphenyl)-3-[2-(methylsulfanyl)-4-pyrimidinyl]pyrazolo[1,5-a]pyridin-7-yl}-N-cyclopentylamine (141 mg, 85%) as a yellow foam. $^1$H NMR (CDCl$_3$) δ 8.15 (d, 1H), 7.84 (d, 1H), 7.51 (d, 2H), 6.99 (d, 2H), 6.65 (d, 1H), 6.09 (d, 1H), 6.02 (d, 1H), 3.96 (m, 1H), 3.88 (s, 3H), 2.63 (s, 3H), 2.15 (m, 2H), 1.81–1.69 (m, 6H). MS m/z 466 (M+1).

EXAMPLE 37

N-{5-Chloro-2-(4-methoxyphenyl)-3-[2-(methylsulfinyl)-4-pyrimidinyl]pyrazolo[1,5-a]pyridin-7-yl}-N-cyclopentylamine

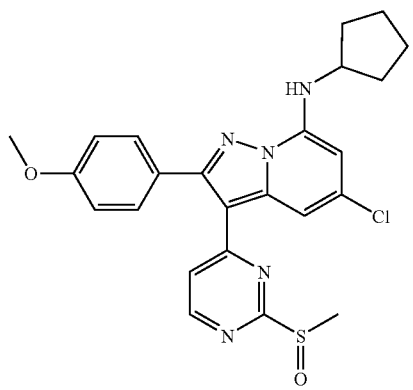

To a solution of N-{5-chloro-2-(4-methoxyphenyl)-3-[2-(methylsulfanyl)-4-pyrimidinyl]pyrazolo[1,5-a]pyridin-7-yl}-N-cyclopentylamine (133 mg, 0.28 mmol) in chloroform (10 mL) was added sodium bicarbonate (24 mg, 0.28 mmol). The reaction mixture was cooled to 0° C. m-Chloroperoxybenzoic acid (57~86%, 86 mg, 0.50 mmol) was added. After stirring at 0° C. for 1.5 hours, the reaction mixture was quenched by addition of aqueous sodium bicarbonate and the resulting mixture extracted with dichloromethane. The organics were combined and washed with water, then dried over magnesium sulfate. Filtration and concentration followed by chromatography (19:1 dichloromethane/methanol) gave N-{5-chloro-2-(4-methoxyphenyl)-3-[2-(methylsulfinyl)-4-pyrimidinyl]pyrazolo[1,5-a]pyridin-7-yl}-N-cyclopentylamine (121 mg, 88%) as a yellow solid. $^1$H NMR (CDCl$_3$) δ 8.43 (d, 1H), 7.93 (d, 1H), 7.51 (d, 2H), 7.00 (d, 2H), 6.98 (d, 1H), 6.11 (d, 1H), 6.08 (d, 1H), 3.96 (m, 1H), 3.88 (s, 3H), 2.99 (s, 3H), 2.13 (m, 2H), 1.82–1.66 (m, 6H). MS m/z 482 (M+1).

EXAMPLE 38

N-{4-[5-Chloro-7-(cyclopentylamino)-2-(4-methoxyphenyl)pyrazolo[1,5-a]pyridin-3-yl]-2-pyrimidinyl}-N-cyclopropylamine

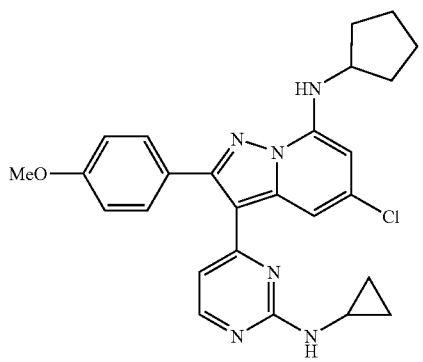

A solution of N-{5-chloro-2-(4-methoxyphenyl)-3-[2-(methylsulfinyl)-4-pyrimidinyl]pyrazolo[1,5-a]pyridin-7-yl}-N-cyclopentylamine (118 mg, 0.24 mmol) in cyclopropylamine (5 mL) was heated at 45° C. in a sealed tube for 5 hours. The reaction mixture was cooled to room temperature and ethyl acetate was added to the reaction mixture. The organic phase was washed with water, brine and dried over magnesium sulfate. Filtration and concentration followed by chromatography (7:3 hexanes/ethyl acetate) gave N-{4-[5-chloro-7-(cyclopentylamino)-2-(4-methoxyphenyl)pyrazolo[1,5-a]pyridin-3-yl]-2-pyrimidinyl}-N-cyclopropylamine (96 mg, 83%) as a yellow solid. $^1$H NMR (CDCl$_3$) δ 8.10 (broad s, 1H), 8.00 (d, 1H), 7.55 (d, 2H), 6.98 (d, 2H), 6.33 (d, 1H), 6.09 (d, 1H), 5.98 (d, 1H), 5.68 (s, 1H), 3.93 (m, 1H), 3.86 (s, 3H), 2.84 (m, 1H), 2.10 (m, 2H), 1.78–1.65 (m, 6H), 0.90 (m, 2H), 0.63 (m, 2H). MS m/z 475 (M+1).

EXAMPLE 39

4-{5-Chloro-7-(cyclopentylamino)-3-[2-(cyclopropylamino)-4-pyrimidinyl]pyrazolo[1,5-a]pyridin-2-yl}phenol

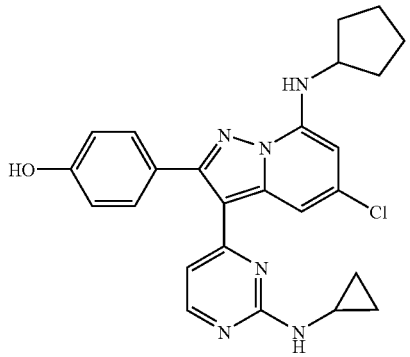

In a similar manner as described before, from N-{4-[5-chloro-7-(cyclopentylamino)-2-(4-methoxyphenyl)pyrazolo[1,5-a]pyridin-3-yl]-2-pyrimidinyl}-N-cyclopropylamine (73 mg, 0.15 mmol) was obtained 4-{5-chloro-7-(cyclopentylamino)-3-[2-(cyclopropylamino)-4-pyrimidinyl]pyrazolo[1,5-a]pyridin-2-yl}phenol (27 mg, 38%) as a yellow foam. $^1$H NMR (CDCl$_3$) δ 8.10 (broad s, 1H), 7.98 (d, 1H), 7.48 (d, 2H), 6.96 (d, 2H), 6.38 (d, 1H), 6.15 (d, 1H), 6.05 (d, 1H), 5.56 (s, 1H), 4.01 (m, 1H), 2.90 (m, 1h), 2.16 (m, 2H), 1.84–1.72 (m, 6H), 0.97 (m, 2H), 0.70 (m, 2H). MS m/z 461 (M+1).

EXAMPLE 40

N-(4-{5-Chloro-7-(cyclopentylamino)-2-[4-(cyclopropyl-methoxy)phenyl]pyrazolo[1,5-a]pyridin-3-yl}-2-pyrimidinyl)-N-cyclopropylamine

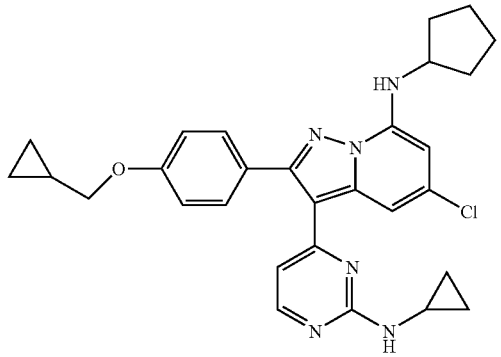

In a similar manner as described above, from 4-{5-chloro-7-(cyclopentylamino)-3-[2-(cyclopropylamino)-4-pyrimidinyl]pyrazolo[1,5-a]pyridin-2-yl}phenol (27 mg, 0.058 mmol) was obtained N-(4-{5-Chloro-7-(cyclopentylamino)-2-[4-(cyclopropyl-methoxy)phenyl]pyrazolo[1,5-a]pyridin-3-yl}-2-pyrimidinyl)-N-cyclopropylamine (21 mg, 70%) as a yellow solid. $^1$H NMR (CDCl$_3$) δ 8.10 (broad s, 1H), 8.00 (d, 1H), 7.53 (d, 2H), 6.98 (d, 2H), 6.34 (d, 1H), 6.08 (d, 1H), 5.99 (d, 1H), 5.39 (s, 1H), 3.95 (m, 1H), 3.86 (d, 2H), 2.86 (m, 1H), 2.14 (m, 2H), 1.80–1.67 (m, 6H), 1.31 (m, 1H), 0.93 (m, 2H), 0.66 (m, 4H), 0.40 (m, 2H). MS m/z 515 (M+1).

EXAMPLE 41

7-Chloro-N-cyclopentyl-3-[2-(cyclopentylamino)pyrimidin-4-yl]-2-(4-fluorophenyl)pyrazolo[1,5-a]pyridin-5-amine

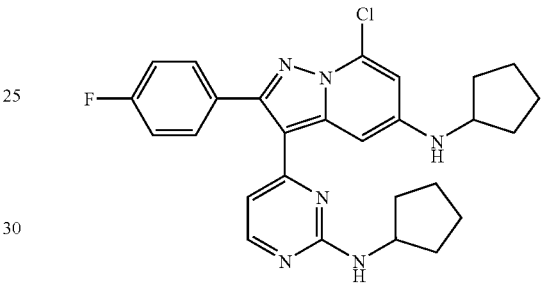

a) 2-(4-Chloro-2-pyridinyl)-1-(4-fluorophenyl)ethanone.

To a cold (0° C.) solution of 4-chloro-2-picoline (5.0 g, 39 mmol) and ethyl 4-fluorobenzoate (6.6 g, 39 mmol) in tetrahydrofuran (100 mL) was added lithium bis(trimethylsilyl)amide (80 mL, 1.0 M in tetrahydrofuran, 80 mmol) dropwise via a pressure equalizing funnel over 30 minutes. Upon complete addition, the cold bath was removed and the resulting solution was stirred at room temperature for 15 hours. The reaction mixture was concentrated under reduced pressure and methanol was added to the reaction, resulting in the formation of a white precipitate. The precipitate was collected by filtration and dried to give 2-(4-chloro-2-pyridinyl)-1-(4-fluorophenyl)ethanone (9.6 g, 99%) as a white solid. $^1$H-NMR (DMSO-d$_6$): δ 7.90 (m, 3H), 7.11 (t, 2H), 6.56 (s, 1H), 5.67 (s, 1H), 4.14 (m, 2H); $^{19}$F-NMR (DMSO-d$_6$): δ −115.67; MS m/z 250 (M+1).

b) 2-(4-Chloro-2-pyridinyl)-1-(4-fluorophenyl)ethanone oxime.

To a solution of 2-(4-chloro-2-pyridinyl)-1-(4-fluorophenyl)ethanone (9.6 g, 38 mmol) in methanol (200 mL) was added hydroxylamine hydrochloride (13.5 g, 190 mmol) followed by the addition of a sodium hydroxide solution (7.8 g, 190 mmol in 50 mL of water). The resulting suspension was heated at reflux for 2 hours and then allowed to cool to room temperature. The mixture was concentrated and water was added to the resulting slurry. A white precipitate formed, which was collected by filtration, washed with water and dried (magnesium sulfate) to give 2-(4-chloro-2-pyridinyl)-1-(4-fluorophenyl)ethanone oxime (8.45 g, 84%) as a white solid. $^1$H-NMR (DMSO-d$_6$): δ 11.56 (s, 1H), 8.44 (d, 1H), 7.80 (m, 2H), 7.40 (m, 2H), 7.22 (m, 2H), 4.29 (s, 2H); $^{19}$F-NMR (DMSO-d$_6$): δ −113.44; MS m/z 265 (M+1).

c) 5-Chloro-2-(4-fluorophenyl)pyrazolo[1,5-a]pyridine.

To a solution of 2-(4-chloro-2-pyridinyl)-1-(4-fluorophenyl)ethanone oxime (8.0 g, 30 mmol) in 1,2-dimethoxyethane (50 mL) at 0° C. was added trifluoroacetic anhydride (6.3 g, 30 mmol), keeping the temperature below 10° C. during the addition. After the addition was complete, the reaction was warmed to room temperature. The solution was then cooled to 4° C. and a solution of triethylamine (8.4 mL, 60 mmol) in 1,2-dimethoxyethane (20 mL) was added over a period of 0.5 hours. The mixture was allowed to warm to room temperature and was stirred for 1.5 hours. To this mixture was added iron(II) chloride (40 mg) and the reaction was heated at 75° C. for 15 hours. The reaction mixture was poured into water (300 mL). The resulting suspension was extracted with ethyl acetate. The combined organics were dried (magnesium sulfate), filtered and concentrated to a solid residue. This residue was purified by flash chromatography (1:1 ethyl acetate-hexane) to give 5-chloro-2-(4-fluorophenyl)-pyrazolo[1,5-a]pyridine (4.2 g, 57%) as a white solid. $^1$H-NMR (CDCl$_3$): δ 8.36 (d, 1H), 7.93 (q, 2H), 7.49 (d, 1H), 7.15 (t, 2H), 6.70 (dd, 1H), 6.69 (s, 1H); $^{19}$F-NMR (CDCl$_3$): δ −113.30; MS m/z 247 (M+1).

d) 5-Chloro-2-(4-fluorophenyl)pyrazolo[1,5-a]pyridine-3-carbaldehyde. Phosphorous oxychloride (0.6 mL, 6.4 mmol) was added to N,N-dimethylformamide (10 mL) and the resulting mixture stirred at room temperature for 10 minutes. 5-Chloro-2-(4-fluorophenyl)pyrazolo[1,5-a]pyridine (1.0 g, 4.1 mmol) was added and the reaction mixture was stirred at room temperature for 12 hours. The reaction mixture was poured into ice-water and neutralized to pH 7 with aqueous ammonium hydroxide. The resulting slurry was extracted with dichloromethane (3×40 mL). The combined organics were washed with brine, dried (magnesium sulfate), filtered and concentrated to give, after recrystallization from acetonitrile, 5-chloro-2-(4-fluorophenyl)pyrazolo [1,5-a]pyridine-3-carbaldehyde (0.95 g, 85%) as a white solid. $^1$H-NMR (CDCl$_3$): δ10.07 (s, 1H), 8.49 (d, 1H), 8.44 (d, 1H), 7.78 (q. 2H), 7.22 (t, 2H), 7.07 (dd, 1H); MS m/z 275 (M+1).

e) 1-[5-Chloro-2-(4-fluorophenyl)pyrazolo[1,5-a]pyridin-3-yl]-2-butyn-1-one.

To a solution of 5-chloro-2-(4-fluorophenyl)pyrazolo[1,5-a]pyridine-3-carbaldehyde (0.93 g, 3.4 mmol) in tetrahydrofuran (20 mL) at −78° C. was added ethynylmagnesium bromide (16 mL, 0.5 M in tetrahydrofuran, 8.0 mmol). The mixture was allowed to warm to room temperature and stirred for 1 hour. Water was added to the reaction and the resulting mixture was extracted with ethyl acetate. The ethyl acetate phase was dried (magnesium sulfate), filtered and concentrated to a solid residue. This residue was dissolved in dichloromethane (50 mL) and manganese dioxide (5 g) was added. This slurry was stirred at room temperature for 2 hours. The manganese dioxide was removed by filtration and the filtrate was concentrated to a solid. This solid was purified by flash chromatography (dichloromethane) to give 1-[5-chloro-2-(4-fluorophenyl)pyrazolo[1,5-a]pyridin-3-yl]-2-butyn-1-one (0.63 g, 62% for two steps) as a white solid. $^1$H-NMR (CDCl$_3$): δ 8.52 (d, 1H), 8.47 (d, 1H), 7.69 (q, 2H), 7.18 (t, 2H), 7.07 (dd, 1H), 3.00 (s, 1H); $^{19}$F-NMR (CDCl$_3$): δ −111.69; MS m/z 299 (M1).

f) 4-[5-Chloro-2-(4-fluorophenyl)pyrazolo[1,5-a]pyridin-3-yl]-N-cyclopentyl-2-pyrimidinamine.

To a solution of 1-[5-chloro-2-(4-fluorophenyl)pyrazolo [1,5-a]pyridin-3-yl]-2-butyn-1-one (0.61 g, 2.0 mmol) in N,N-dimethylformamide was added cyclopentyl guanidine hydrochloride (0.67 g, 4.1 mmol) followed by anhydrous potassium carbonate (0.57 g, 4.1 mmol). The resulting mixture was heated at 80° C. for 12 hours. Upon cooling to room temperature, water was added. The mixture was extracted with ethyl acetate. The ethyl acetate phase was washed with brine, dried (magnesium sulfate), filtered and concentrated in vacuo. The resulting residue was purified by flash chromatography (1:1 ethyl acetate-hexane) to give, after recrystallization from acetonitrile, 4-[5-chloro-2-(4-fluorophenyl)pyrazolo[1,5-a]pyridin-3-yl]-N-cyclopentyl-2-pyrimidinamine (0.6 g, 74%) as a white solid. $^1$H-NMR (CDCl$_3$): δ8.54 (broad s, 1H), 8.40 (d, 1H), 8.04 (d, 1H), 7.60 (q, 2H), 7.16 (t, 2H), 6.88 (dd, 1H), 6.28 (d, 1H), 5.22 (d, 1H), 4.40 (m, 1H), 1.4–2.2 (m, 8H); $^{19}$F-NMR (CDCl$_3$): δ −112.5; MS m/z 408 (M+1).

g) N-Cyclopentyl-3-[2-(cyclopentylamino)-4-pyrimidinyl]-2-(4-fluorophenyl)-pyrazolo[1,5-a]pyridin-5-amine.

To a solution of 4-[5-chloro-2-(4-fluorophenyl)pyrazolo [1,5-a]pyridin-3-yl]-N-cyclopentyl-2-pyrimidinamine (0.1 g, 0.25 mmol) in cyclopentylamine (5 mL) was added racemic-2,2'-bis(diphenylphosphino)-1,1'-binaphthyl (46 mg, 0.08 mmol), cesium carbonate (120 mg, 0.38 mmol) and palladium (II) acetate (11 mg, 0.05 mmol). The resulting mixture was stirred at 80° C. for 24 hours, at which time the reaction was judged complete by thin layer chromatography. The solution was cooled to room temperature and ethyl acetate and water were added to the reaction mixture. The phases were separated, and the aqueous phase again extracted with ethyl acetate. The combined organics were dried (magnesium sulfate), filtered and concentrated. The resulting residue was purified by flash chromatography (1:1 hexanes-ethyl acetate) to give N-cyclopentyl-3-[2-(cyclopentylamino)-4-pyrimidinyl]-2-(4-fluorophenyl)pyrazolo[1,5-a] pyridin-5-amine (78 mg, 70%) as a white solid. $^1$H-NMR (CDCl$_3$): δ 8.16 (d, 1H), 7.95 (d, 1H), 7.58 (q, 2H), 7.38 (d, 1H), 7.12 (t, 2H), 6.24 (dd, 1H), 6.20 (d, 1H), 5.05 (d, 1H), 4.40 (m, 1H), 4.13 (m, 1H), 3.89 (m, 1H), 1.5–2.2 (m, 16H);$^{19}$F-NMR (CDCl$_3$): δ −113.7; MS m/z 457 (M+1).

h) 7-Chloro-N-cyclopentyl-3-[2-(cyclopentylamino)pyrimidin-4-yl]-2-(4-fluorophenyl)pyrazolo[1,5-a]pyridin-5-amine.

To a solution of N-cyclopentyl-3-[2-(cyclopentylamino)-4-pyrimidinyl]-2-(4-fluorophenyl)pyrazolo[1,5-a]pyridin-5-amine (120 mg, 0.26 mmol) in tetrahydrofuran (5 mL) at −78 ° C. was added n-butyllithium (0.8 mL, 1.3 mmol of 1.6 M solution in hexanes). The resulting reaction was stirred at −78° C. for 10 minutes, then carbon tetrachloride (1 mL) was added. The reaction mixture was allowed to warm to room temperature and then quenched by the addition of water. The phase were separated and the organic phase dried over magnesium sulfate, filtered and concentrated. The resulting residue was purified by flash chromatography (1:1 hexanes-ethyl acetate) to give 7-chloro-N-cyclopentyl-3-[2-(cyclopentylamino)pyrimidin-4-yl]-2-(4-fluorophenyl)pyrazolo[1,5-a]pyridin-5-amine (12 mg) as a foam. $^1$H-NMR (CDCl$_3$): δ 7.97 (d, 1H), 7.62 (q, 2H), 7.44 (d, 1H), 7.15 (t, 2H), 6.48 (d, 1H), 6.22 (d, 1H), 5.30 (broad s, 1H), 4.44 (m, 1H), 4.18 (m, 1H), 3.94 (m, 1H), 1.4–2.1 (16H);$^{19}$F-NMR (CDCl$_3$): δ −113.24; MS m/z 492 (M+1).

EXAMPLE 42

4,6-Dibromo-N-cyclopentyl-3-[2-(cyclopentylamino)pyrimid in-4-yl]-2-(4-fluorophenyl)pyrazolo[1,5-a]pyridin-7-amine

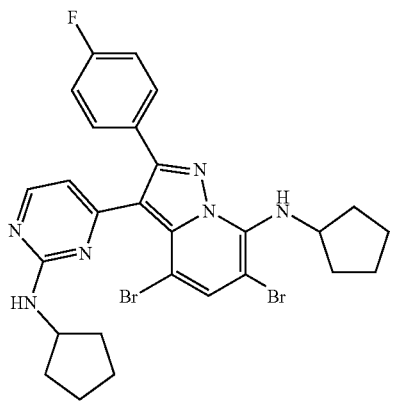

The title compound was prepared in a similar manner as previous examples. $^1$H NMR (CDCl$_3$): δ 8.17 (s, 1 H), 7.56–7.50 (m, 2 H), 7.50 (s, 1 H), 7.04 (t, 2 H), 6.55 (d, 1 H), 6.10 (d, 1 H), 5.70 (broad, 1 H), 4.88 (m, 1 H), 4.28 (m, 1 H), 2.07–1.43 (m, 16 H); MS m/z 613 (M+1). This material was treated with anhydrous hydrogen chloride in ether to provide the corresponding HCl salt as a solid.

EXAMPLE 43

4,6-Dibromo-3-[5-bromo-2-(cyclopentylamino)pyrimidin-4-yl]-N-cyclopentyl-2-(4-fluorophenyl)pyrazolo[1,5-a]pyridin-7-amine

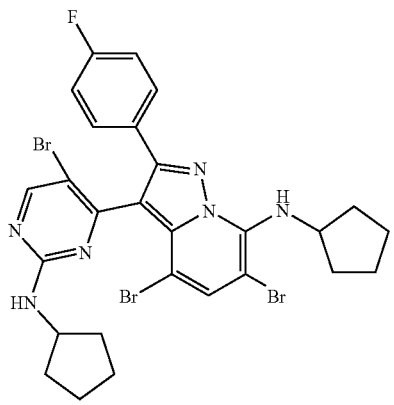

The title compound was prepared in a similar manner as previous examples to give a white foam. $^1$H NMR (CDCl$_3$): δ 8.34 (s, 1 H), 7.57 (dd, 2 H), 7.45 (s, 1 H), 7.03 (t, 2 H), 6.08 (d, 1 H), 5.17 (m, 1 H), 4.89 (m, 1 H), 4.20 (m, 1 H), 2.09–1.37 (m, 16 H); MS m/z 691 (M+1).

EXAMPLE 44

6-Chloro-N-cyclopentyl-3-[2-(cyclopentylamino)pyrimidin-4-yl]-2-(4-fluorophenyl)pyrazolo[1,5-a]pyridin-7-amine

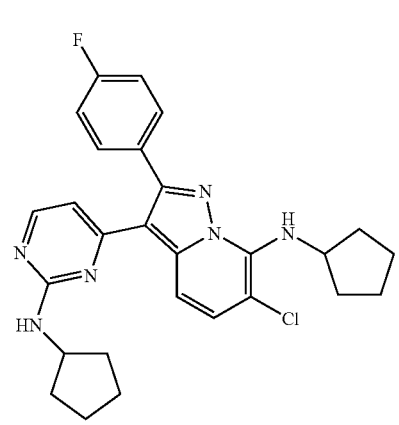

The title compound was prepared in a similar manner as previous examples to give a white foam. $^1$H NMR (CDCl$_3$): δ 8.07 (d, 1 H), 7.76 (d, 1 H), 7.66 (dd, 2 H), 7.30 (d, 1 H), 7.17 (t, 2 H), 6.32 (d, 1 H), 6.13 (d, 1 H), 5.14 (m, 1 H), 4.86 (m, 1 HO, 4.35 (m, 1 H), 2.13–1.54 (m, 16 H); $^{19}$F NMR (CDCl$_3$): δ −113.09; MS m/z 491 (M+1).

EXAMPLE 45

N-Cyclopentyl-3-[2-(cyclopentylamino)-4-pyrimidinyl]-2-(4-fluorophenyl)-5-methoxypyrazolo[1,5-a]pyridin-7-amine

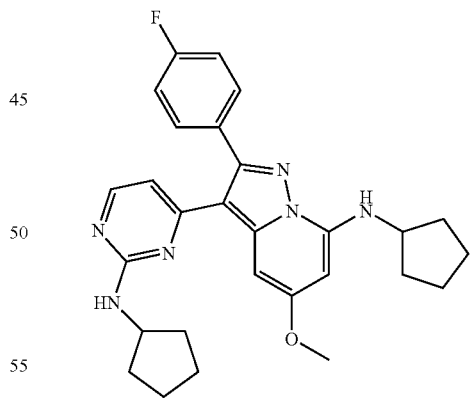

The title compound was prepared in a similar manner as previous examples to give a yellow solid. R$_f$ 0.51 (39:1 dichloromethane:methanol); $^1$H NMR (CDCl$_3$): δ 7.98 (d, 1H), 7.60 (m, 2H), 7.28 (s, 1H), 7.15 (t, 2H), 6.20 (d, 1H), 5.91 (d, 1H), 5.72 (s, 1H), 5.05 (d, 1H), 4.42 (m, 1H), 3.99–3.88 (m, 4H), 2.21–2.03 (m, 4H), 1.90–1.50 (m, 12H); MS m/z 487 (M+1); Anal. Calcd for C$_{28}$H$_{31}$FN$_6$O.025C$_4$H$_8$O$_2$: C, 68.48; H, 6.54; N, 16.52. Found: C, 68.82; H, 6.64; N, 16.23; mp 167–169° C.

EXAMPLE 46

N-Cyclopentyl-3-[2-(cyclopentylamino)-4-pyrimidinyl]-2-(4-fluorophenyl)-5-(2-methoxyethoxy)pyrazolo[1,5-a]pyridin-7-amine

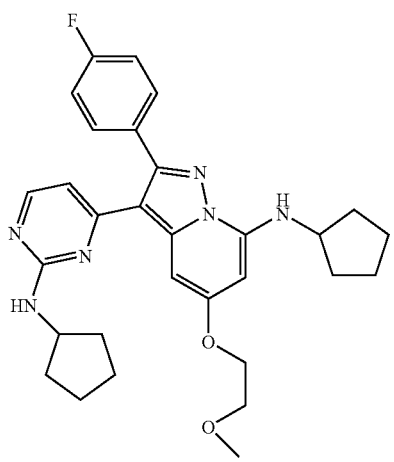

The title compound was prepared in a similar manner as previous examples to give an orange solid. $R_f$ 0.17 (7:3 hexanes:ethyl acetate); $^1$H NMR (CDCl$_3$): δ 7.99 (d, 1H), 7.60 (m, 2H), 7.25 (5, 1H), 7.16 (t, 2H), 6.20 (d, 1H), 5.90 (d, 1H), 5.80 (s, 1H), 5.12 (d, 1H), 4.40 (m, $_1$H), 4.22 (m, 2H), 3.92 (m, 1H), 3.80 (m, 2H), 3.49 (s, 3H), 2.20–2.02 (m, 4H), 1.90–1.50 (m, 12H); MS m/z 531 (M+1).

EXAMPLE 47

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV Infection.

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 μM primers, 180 μM dTTP, 20 μM dUTP-digoxigenin (Boehringer Mannheim 1558706), 200 μM each of dATP, dCTP, and dGTP, 1×PCR Buffer II (Perkin Elmer), 2.5 mM MgCl$_2$, 0.025 units/μL of AmpliTaq Gold polymerase (Perkin Elmer), and 5 ng of gel-purified HSV DNA per 100 μL. Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL 15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration:3M GuSCN, 50 mM EDTA, 100 μg/ml salmon sperm DNA, 5× Denhardt's solution, 0.25×APE, and 5 ng of the digoxigenin-labeled detection probe). APE is 1.5 M NH$_4$-acetate, 0.15 M NH$_4$H$_2$ phosphate, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with with 300 μL/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

(e) Results.

The following results were obtained for HSV-1.

| Example No. | IC$_{50}$ (μM) |
|---|---|
| 1 | 5.3 |
| 2 | 3.3 |
| 3 | 6.3 |
| 4 | 0.5 |
| 5 | 4.1 |
| 6 | 4.0 |
| 7 | 1.0 |
| 8 | 5.0 |
| 9 | 0.5 |
| 10 | 4.2 |

-continued

| Example No. | IC$_{50}$ (µM) |
|---|---|
| 11 | 0.97 |
| 12 | 7.0 |
| 13 | 0.17 |
| 14 | 0.24 |
| 15 | 1.45 |
| 16 | 0.55 |
| 17 | 5.2 |
| 18 | 0.25 |
| 19 | 0.2 |
| 20 | 0.5 |
| 21 | 0.6 |
| 22 | 0.2 |
| 23 | 0.5 |
| 24 | 0.12 |
| 25 | 0.19 |
| 26 | 0.26 |
| 27 | 1.6 |
| 28 | 3.5 |
| 29 | 0.35 |
| 30 | 0.33 |
| 31 | 1.50 |
| 32 | 0.8 |
| 33 | 0.8 |
| 34 | 0.12 |
| 35 | >40 |
| 36 | 22 |
| 37 | 6 |
| 38 | 0.34 |
| 39 | 2.0 |
| 40 | 1.3 |
| 41 | 1.3 |
| 42 | 20 |
| 43 | >40 |
| 44 | 0.9 |
| 45 | 0.15 |
| 46 | 0.13 |

The results demonstrate that the compounds of the present invention are useful for the treatment and prophylaxis of herpes viral infections.

The invention claimed is:

1. A compound of formula (I):

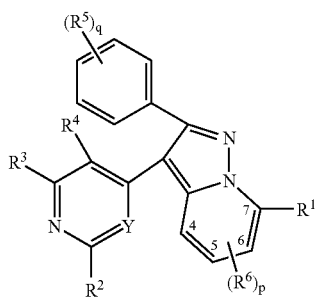

wherein:
R$^1$ is selected from the group consisting of halo, Ay, Het, —NR$^7$R$^8$, —NR$^7$Ay, —NHHet, —NHR$^{10}$Ay and —NHR$^{10}$Het;

each R$^7$ and R$^8$ are the same or different and are independently selected from the group consisting of H, alkyl, alkenyl, cycloalkyl, cycloalkenyl, —OR$^9$, —C(O)R$^9$, —CO$_2$R$^9$, —C(O)NR$^9$R$^{11}$, —C(S)NR$^9$R$^{11}$, —C(NH)NR$^9$R$^{11}$, —SO$_2$R$^{10}$, —SO$_2$NR$^9$R$^{11}$, —R$^{10}$cycloalkyl, —R$^{10}$OR$^9$, —CH(R$^{10}$OR$^9$)$_2$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^{10}$, —R$^{10}$SO$_2$NR$^9$R$^{11}$, —R$^{10}$SO$^2$NHCOR$^9$, —R$^{10}$NR$^9$R$^{11}$, —R$^{10}$NHCOR$^9$, —R$^{10}$NHSO$_2$R$^9$ and —R$^{10}$NHC(NH)NR$^9$R$^{11}$ and;

each R$^9$ and R$^{11}$ are the same or different and are independently selected from the group consisting of H, alkyl, cycloalkyl, —R$^{10}$cycloalkyl, —R$^{10}$OH, —R$^{10}$(OR$^{10}$)$_w$ where w is 1–10, and —R$^{10}$NR$^{10}$R$^{10}$;

each R$^{10}$ is the same or different and is independently selected from the group consisting of alkyl, alkenyl, alkynyl, cycloalkyl and cycloalkenyl;

Ay is aryl;

Het is a 5- or 6-membered heterocyclic or heteroaryl group;

n is 0, 1 or 2;

R$^2$ is selected from the group consisting of halo, alkyl, alkenyl, cycloalkyl, cycloalkenyl, Ay, Het, —OR$^7$, —OAy, —OHet, —OR$^{10}$Het, —S(O)$_n$R$^9$, —S(O)$_n$Ay, —S(O)$_n$Het, —S(O)$_n$NR$^7$R$^8$, —NR$^7$R$^8$, —NHHet, —NHR$^{10}$Ay, —NHR$^{10}$Het, —R$^{10}$NR$^7$R$^8$ and —R$^{10}$NR$^7$Ay;

Y is CH;

R$^3$ and R$^4$ are the same or different and are each independently selected from the group consisting of H, halo, alkyl, alkenyl, cycloalkyl, Ay, Het, —OR$^7$, —OAy, —C(O)R$^7$, C(O)Ay, —CO$_2$R$^7$, —CO$_2$Ay, —SO$_2$NHR$^9$, —NR$^7$R$^8$, —NR$^7$Ay, —NHHet, —NHR$^{10}$Het —R$^{10}$OR$^7$, —R$^{10}$OAy, —R$^{10}$NR$^7$R$^8$ and —R$^{10}$NR$^7$Ay;

q is 0, 1, 2, 3, 4 or 5;

each R$^5$ is the same or different and is independently selected from the group consisting of halo, alkyl, alkenyl, alkynyl, cycloalkyl, cycloalkenyl, Ay, Het, —OR$^7$, —OAy, —OHet, —C(O)R$^9$, —C(O)Ay, —C(O)Het, —CO$_2$R$^9$, —C(O)NR$^7$R$^8$, —C(O)NR$^7$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$OR$^9$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent R$^5$ groups together with the atoms to which they are bonded form a C$_{5-6}$ cycloalkyl or aryl;

p is 1, 2 or 3; and each R$^6$ is the same or different and is independently selected from the group consisting of halo, alkyl, alkenyl, alkynyl, cycloalkyl, cycloalkenyl, Ay, Het, —OR$^7$, —OAy, —OHet, —OR$^{10}$Ay, —OR$^{10}$Het, —C(O)R$^9$, —C(O)Ay, —C(O)Het, —CO$_2$R$^9$, —C(O)NR$^7$R$^8$, —C(O)NR$^7$Ay, —C(O)NHR$^{10}$Ay, —C(O)NHR$^{10}$Het, —C(S)NR$^9$R$^{11}$, —C(NH)NR$^7$R$^8$, —C(NH)NR$^7$Ay, —S(O)$_n$R$^9$, —S(O)$_n$Ay, —S(O)$_n$Het, —S(O)$_2$NR$^7$R$^8$, —S(O)$_2$NR$^7$Ay, —NR$^7$R$^8$, —NR$^7$Ay, —NHHet, —NHR$^{10}$Ay, —NHR$^{10}$Het, —R$^{10}$cycloalkyl, —R$^{10}$Ay, —R$^{10}$Het, —R$^{10}$OR$^9$, —R$^{10}$—O—C(O)R$^9$, —R$^{10}$—O—C(O)Ay, —R$^{10}$—O—C(O)Het, —R$^{10}$—O—S(O)$_n$R$^9$, —R$^{10}$C(O)R$^9$, —R$^{10}$CO$_2$R$^9$, —R$^{10}$C(O)NR$^9$R$^{11}$, —R$^{10}$C(S)NR$^9$R$^{11}$, —R$^{10}$C(NH)NR$^9$R$^{11}$, —R$^{10}$SO$_2$R$^9$, —R$^{10}$SO$_2$NR$^9$R$^{11}$, —R$^{10}$SO$_2$NHCOR$^9$, —R$^{10}$NR$^7$R$^8$, —R$^{10}$NR$^7$Ay, —R$^{10}$NHC(NH)NR$^9$R$^{11}$, cyano, nitro and azido; or two adjacent $R^6$ groups together with the atoms to which they are bonded form a $C_{5-6}$ cycloalkyl or a 5- or 6-membered heterocyclic group containing 1 or 2 heteroatoms; or $R^6$ is in the 6 position and $R^6$ and $R^1$ together with the atoms to which they are bonded form a $C_{5-6}$ cycloalkyl or a 5- or 6-membered heterocyclic group containing 1 or 2 heteroatoms;

wherein when Y is CH, $R^3$ is not —$NR^7Ay$;

or a pharmaceutically acceptable salt or solvate thereof.

2. The compound according to claim 1 wherein $R^1$ is selected from the group consisting of halo, Ay, Het, —$NR^7R^8$, —NHHet, —$NHR^{10}Ay$ and —$NHR^{10}Het$.

3. The compound according to claim 1 wherein $R^1$ is selected from the group consisting of Het and —$NR^7R^8$.

4. The compound according to claim 1 wherein $R^2$ is selected from the group consisting of $R^2$ is selected from the group consisting of Het, —$OR^7$, —OAy, —OHet, —$OR^{10}Het$, —$S(O)_nR^9$, —$S(O)_nAy$, —$NR^7R^8$, —NHHet and —$NHR^{10}Het$.

5. The compound according to claim 1 wherein $R^2$ is selected from the group consisting of Het, —$NR^7R^8$ and —NHHet.

6. The compound according to claim 1 wherein $R^3$ and $R^4$ are the same or different and are each independently selected from the group consisting of H, halo, alkyl, Ay, —$OR^7$, —$CO_2R^7$, —$NR^7R^8$, —$R^{10}OR^7$ and —$R^{10}NR^7R^8$.

7. The compound according to claim 1 wherein $R^3$ and $R^4$ are each H.

8. The compound according to claim 1 wherein q is 0, 1 or 2.

9. The compound according to claim 1 wherein each $R^5$ is the same or different and is independently selected from the group consisting of halo, alkyl, alkenyl, Ay, Het, —$OR^7$, —OAy, —$CO_2R^9$, —$C(O)NR^7R^8$, —$C(O)NR^7Ay$, —$S(O)_2NR^7R^8$, —$NR^7R^8$, —$NR^7Ay$, —$NHR^{10}Ay$, cyano, nitro and azido.

10. The compound according to claim 1, wherein each $R^5$ is the same or different and is independently selected from the group consisting of halo, alkyl, —$OR^7$, —$NR^7R^8$ and cyano.

11. The compound according to claim 1 wherein p is 1 or 2.

12. The compound according to claim 1 wherein p is 1.

13. The compound according to claim 1 wherein each $R^6$ is the same or different and is independently selected from the group consisting of halo, alkyl, Ay, Het, —$OR^7$, —OAy, —OHet, —C(O)Het, —$CO_2R^9$, —$C(O)NR^7R^8$, —$C(O)NR^7Ay$, —$C(O)NHR^{10}Het$, —$NR^7R^8$, —$NR^7Ay$, —NHHet, —$NHR^{10}Ay$, —$NHR^{10}Het$, —$R^{10}OR^9$ and cyano.

14. The compound according to claim 1, wherein each $R^6$ is the same or different and is independently selected from the group consisting of halo, alkyl, —$C(O)NR^7R^8$, —$NR^7R^8$, —$NR^7Ay$, —NHHet, —$NHR^{10}Ay$, and —$NHR^{10}Het$.

15. A process for preparing the compound according to claim 1, said process comprising the steps of:

a) reacting a compound of formula (XXII):

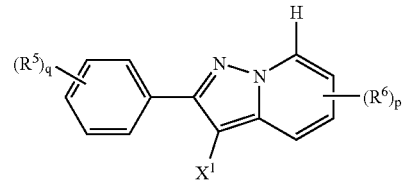

XXII wherein $X^1$ is selected from the group consisting of chloro, bromo and iodo;

with a compound of formula (XXIV):

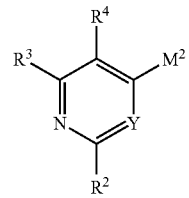

XXIV wherein $M^2$ is selected from the group consisting of —$B(OH)_2$, —$B(ORa)_2$, —$B(Ra)_2$, —$Sn(Ra)_3$, Zn-halide, ZnRa, and Mg-halide where Ra is alkyl or cycloalkyl and halide is halo;

to prepare a compound of formula (IX):

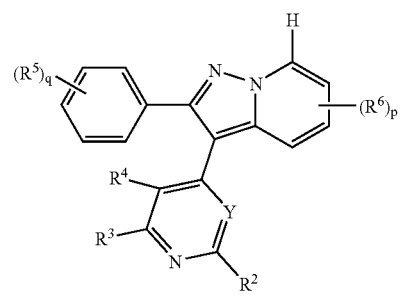

IX b) halogenating the compound of formula (IX) to prepare a compound of formula (I-A):

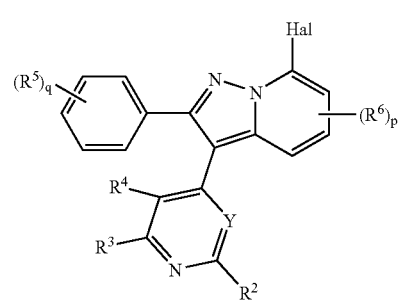

I-A where Hal is halo; and c) optionally either:
1) replacing the C-7 halogen of the compound of formula (I-A) with an amine nucleophile selected from the group consisting of —NR$^7$R$^8$, —NR$^7$Ay, —NHHet, —NHR$^{10}$Ay and —NHR$^{10}$Het; or
2) coupling the compound of formula (I-A) with a metal compound selected from the group consisting of Ay-M$^3$ and Het-M$^3$ wherein M$^3$ is —B(OH)$_2$, —B(ORa)$_2$, —B(Ra)$_2$, —Sn(Ra)$_3$, Zn-halide, Zn—Ra or Mg-halide where Ra is alkyl or cycloalkyl and halide is halo, to prepare a compound of formula (I-B):

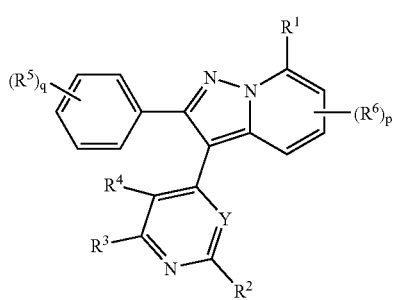

I-B wherein R$^1$ is selected from the group consisting of Ay, Het, —NR$^7$R$^8$, —NR$^7$Ay, —NHHet, —NHR$^{10}$Ay and —NHR$^{10}$Het.

16. The process according to claim 15 further comprising the step of converting the compound of formula (I) to a pharmaceutically acceptable salt or solvate thereof.

17. The process according to claim 15 further comprising the step of converting a compound of formula (I) or a pharmaceutically acceptable salt or solvate thereof to another compound of formula (I) or a pharmaceutically acceptable salt or solvate thereof.

18. A pharmaceutical composition comprising a compound according to claim 1.

19. The pharmaceutical composition according to claim 18 further comprising a pharmaceutically acceptable carrier or diluent.

20. The pharmaceutical composition according to claim 18 further comprising an antiviral agent selected from the group consisting of aciclovir and valaciclovir.

21. A method for the treatment of a herpes simplex virus 1 or herpes simplex virus 2 infection in an animal, said method comprising administering to an animal a therapeutically effective amount of a compound according to claim 1.

22. A method for the treatment of a condition or disease associated with a herpes viral infection selected from herpes simplex virus 1 and herpes simplex virus 2 in an animal, comprising administering to the animal a therapeutically effective amount of the compound of formula (I) according to claim 1.

* * * * *

UNITED STATES PATENT AND TRADEMARK OFFICE
CERTIFICATE OF CORRECTION

| | | |
|---|---|---|
| PATENT NO. | : 7,030,134 B2 | Page 1 of 1 |
| APPLICATION NO. | : 11/095212 | |
| DATED | : April 18, 2006 | |
| INVENTOR(S) | : Gudmundsson et al. | |

It is certified that error appears in the above-identified patent and that said Letters Patent is hereby corrected as shown below:

Title Page
Reads:
Item (56) Foreign Patent Documents
" WO 0 364 204 A1 10/1989 "

Should read:
Item (56) Foreign Patent Documents
-- EP 0 364 204 A1 --

Signed and Sealed this

Twenty-second Day of May, 2007

JON W. DUDAS
*Director of the United States Patent and Trademark Office*